US011014871B2

(12) United States Patent
Alami et al.

(10) Patent No.: US 11,014,871 B2
(45) Date of Patent: May 25, 2021

(54) "MULTI-TARGET" COMPOUNDS WITH INHIBITORY ACTIVITY TOWARDS HISTONE DEACETYLASES AND TUBULIN POLYMERISATION, FOR USE IN THE TREATMENT OF CANCER

(71) Applicants: UNIVERSITE PARIS-SUD, Orsay (FR); CENTRE NATIONAL DE LA RECHERCHE SCIENTIFIQUE (CNRS), Paris (FR)

(72) Inventors: Mouâd Alami, Bussy Saint Georges (FR); Abdallah Hamze, Massy (FR); Jean-Daniel Brion, Saint Leu la Foret (FR); Jérôme Bignon, Le Val Saint Germain (FR); Joëlle Dubois, Gometz-la-Ville (FR)

(73) Assignees: CENTRE NATIONAL DE LA RECHERCHE SCIENTIFIQUE (CNRS), Paris (FR); UNIVERSITE PARIS-SUD, Orsay (FR)

( * ) Notice: Subject to any disclaimer, the term of this patent is extended or adjusted under 35 U.S.C. 154(b) by 0 days.

(21) Appl. No.: 16/068,097

(22) PCT Filed: Jan. 5, 2017

(86) PCT No.: PCT/FR2017/050032
§ 371 (c)(1),
(2) Date: Jul. 3, 2018

(87) PCT Pub. No.: WO2017/118822
PCT Pub. Date: Jul. 13, 2017

(65) Prior Publication Data
US 2019/0023645 A1 Jan. 24, 2019

(30) Foreign Application Priority Data
Jan. 5, 2016 (FR) ...................... 1650043

(51) Int. Cl.
| *C07C 69/734* | (2006.01) |
| *C07C 235/64* | (2006.01) |
| *C07D 209/42* | (2006.01) |
| *C07D 213/65* | (2006.01) |
| *A61K 45/06* | (2006.01) |
| *C07D 239/74* | (2006.01) |
| *C07C 235/38* | (2006.01) |
| *C07D 215/14* | (2006.01) |
| *C07C 259/06* | (2006.01) |
| *C07D 213/81* | (2006.01) |
| *C07C 259/10* | (2006.01) |
| *C07D 209/86* | (2006.01) |
| *A61K 47/68* | (2017.01) |
| *A61P 35/00* | (2006.01) |
| *A61K 31/165* | (2006.01) |
| *A61K 31/166* | (2006.01) |
| *A61K 31/167* | (2006.01) |
| *A61K 31/192* | (2006.01) |
| *A61K 31/216* | (2006.01) |
| *A61K 31/404* | (2006.01) |

(Continued)

(52) U.S. Cl.
CPC .......... *C07C 69/734* (2013.01); *A61K 31/165* (2013.01); *A61K 31/166* (2013.01); *A61K 31/167* (2013.01); *A61K 31/192* (2013.01); *A61K 31/216* (2013.01); *A61K 31/404* (2013.01); *A61K 31/44* (2013.01); *A61K 45/06* (2013.01); *A61K 47/6803* (2017.08); *A61P 35/00* (2018.01); *C07C 59/68* (2013.01); *C07C 235/34* (2013.01); *C07C 235/38* (2013.01); *C07C 235/60* (2013.01); *C07C 235/64* (2013.01); *C07C 259/06* (2013.01); *C07C 259/10* (2013.01); *C07D 209/18* (2013.01); *C07D 209/42* (2013.01); *C07D 209/86* (2013.01); *C07D 213/65* (2013.01); *C07D 213/81* (2013.01); *C07D 215/14* (2013.01); *C07D 239/74* (2013.01)

(58) Field of Classification Search
None
See application file for complete search history.

(56) References Cited

U.S. PATENT DOCUMENTS

| 8,273,768 | B2 * | 9/2012 | Alami | .................. C07C 43/215 514/314 |
| 2010/0129471 | A1 * | 5/2010 | Alami | .................. C07C 43/215 424/649 |

FOREIGN PATENT DOCUMENTS

| WO | WO-2007/131364 A1 | 11/2007 |
| WO | WO-2008/122620 A1 | 10/2008 |
| WO | WO-2013/026942 A1 | 2/2013 |

OTHER PUBLICATIONS

Mahapatra et al., "Anti-cancer chalcones: Structural and molecular target perspectives", European Journal of Medicinal Chemistry, vol. 98, May 14, 2015, pp. 69-114.

(Continued)

Primary Examiner — Joseph R Kosack
(74) Attorney, Agent, or Firm — Foley & Lardner LLP; Sunit Talapatra

(57) ABSTRACT

The present invention relates to the design of novel molecules, referred to as "multi-target" molecules, having a double pharmacophore and acting both as inhibitors of histone deacetylases (HDACs) and as inhibitors of tubulin polymerisation. The invention also describes the method for synthesising the "multi-target" molecules and their use in the treatment of cancer, a pharmaceutical composition comprising at least one "multi-target" molecule, and the use of such compositions in the treatment of cancer.

13 Claims, 4 Drawing Sheets

(51) Int. Cl.
*A61K 31/44* (2006.01)
*C07C 59/68* (2006.01)
*C07C 235/34* (2006.01)
*C07C 235/60* (2006.01)
*C07D 209/18* (2006.01)

(56) References Cited

OTHER PUBLICATIONS

French Preliminary Search Report issued in corresponding French Application No. 1650043, dated Sep. 7, 2016.
International Search Report issued in corresponding International Patent Application No. PCT/FR2017/050032, dated Sep. 29, 2017.
Mahal et al., "Biological evaluation of 4,5-diarylimidazoles with hydroxamic acid appendages as novel dual mode anticancer agents", Cancer Chemotherapy and Pharmacology, Springer Verlag, Berlin, vol. 75, No. 4, Jan. 25, 2015, pp. 671-700.
Zhang et al., "Design, synthesis and biological evaluation of colchicine derivatives as novel tubulin and histone deacetylase dual inhibitors", European Journal of Medicinal Chemistry, vol. 95, Mar. 18, 2015, pp. 127-135.
Zhang et al., "The discovery of colchicine-SAHA hybrids as a new class of antitumor agents", Bioorganic & Medicinal Chemistry, vol. 21, No. 11, Mar. 31, 2013, pp. 3240-3244.

* cited by examiner

"MULTI-TARGET" COMPOUNDS WITH INHIBITORY ACTIVITY TOWARDS HISTONE DEACETYLASES AND TUBULIN POLYMERISATION, FOR USE IN THE TREATMENT OF CANCER

CROSS-REFERENCE TO RELATED APPLICATIONS

This application is the National Phase of International Patent Application No. PCT/FR2017/050032 filed Jan. 5, 2017, which claims priority to French Patent Application No. 1650043, filed Jan. 5, 2016. The contents of these applications are herein incorporated by reference in their entirety.

FIELD OF THE INVENTION

The present invention relates to the design of novel molecules, referred to as "multi-target" molecules, having a double pharmacophore and acting both as inhibitors of histone deacetylases (HDACs) and as antivascular agents.

The invention also relates to the process for synthesising the "multi-target" molecules and to their use in the treatment of cancer.

STATE OF THE ART

Cancer is a leading cause of death worldwide, accounting for 7.6 million deaths in 2008. Cancer deaths worldwide are expected to continue to increase, reaching nearly 13 million deaths in 2030. There are over 100 different types of cancer; the five most deadly cancers are lung cancer, colon cancer, liver cancer, prostate cancer and breast cancer. Cancer is a complex pathology characterised by the presence of a malignant tumour (or several malignant tumours) formed from the transformation by mutation or genetic instability (cytogenetic abnormalities) of an initially normal cell.

Tumour cell transformation notably entails a loss of cell cycle control, insensitivity to apoptosis, abnormal DNA repair.

Among the therapies used, so-called conventional chemotherapy involving cytotoxic agents, alone or combined with surgery, radiotherapy, is a leading approach. However, treatments are frequently accompanied by adverse effects, due to a lack of selectivity towards tumour cells. In addition, multidrug resistance, the main mechanism by which many cancers evade treatment, is an important factor in the failure of many chemotherapies.

Consequently, such approaches must constantly evolve in order to remove these main barriers.

Recent advances in cancer treatment are linked to the arrival of "targeted therapies" aiming specifically certain mechanisms involved in cell regulation and growth. This more rational approach has significantly changed the way patients are managed. The active principles used are generally better tolerated and do not cause the side effects specific to conventional chemotherapies (hair loss, nausea, vomiting). However, these active principles can cause toxicities such as increased blood pressure, headaches, proteinuria, allergic reactions, or digestive disorders.

Targeted treatments include several families of antitumour drugs: monoclonal antibodies, tyrosine kinase receptor inhibitors, and angiogenesis inhibitors. Despite all the interest in these targeted therapies, treatments aimed at a single target have shown limited results, due to the great biological diversity of cancers and the emergence of resistance phenomena. The combination of several active principles (or multidrug therapy) having different mechanisms of action and targeting the most critical impairments of this disease seems to be one solution provided that the toxicity of each active principle taken separately is not cumulative.

Development paths now focus on the use of dual molecules that inhibit or modulate several targets simultaneously. This multi-target drug discovery (MTDD) approach is attracting interest from the pharmaceutical industry.

Tyrosine kinase inhibitors (TKIs) are a good example of this MTDD concept capable of blocking the signalling of VEGFR, PDGFR and other membrane and/or cytoplasmic kinases.

For example, imatinib, a TKI targeting the BCR-Abl enzyme in chronic myeloid leukaemia, had to quickly address the problem of relapse. Many patients have developed resistance to imatinib, mainly due to activation of alternative receptor tyrosine kinase pathways. Recently, the FDA approved the use of sorafenib, a multikinase inhibitor that has shown antitumour activity in patients with advanced renal cell carcinoma and hepatocellular carcinoma. The multiple molecular targets of sorafenib (serine/threonine kinase "Raf" and receptor tyrosine kinases "VEGFR-2, VEGFR-3, and PDGFR-β") may explain its broad preclinical and clinical activities.

Therefore, in the field of drug discovery, different scenarios have emerged, such as a novel generation of antitumour drugs capable of simultaneously inhibiting several biological pathways, thus constituting a major advance in this therapy.

For example, application WO 2007/131364 relates to novel hybrid molecules having two pharmacophores, one being calcitriol and the other comprising an alkyl or alkenyl chain having a hydroxamic acid terminal group, both acting synergistically as vitamin D receptor agonists and as HDAC inhibitors.

Much research has also focused on the natural molecule, combretastatin A-4 (CA-4). CA-4 is a stilbene of Z-configuration substituted by two aromatic rings: 3,4,5-trimethoxyphenyl (ring A) and 3-hydroxy-4-methoxyphenyl (ring B).

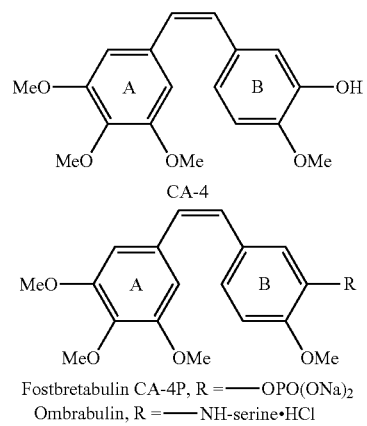

CA-4 proves to be highly cytotoxic ($IC_{50}$=1-2 nM) to many human cancer lines and to lines resistant to conventional therapies. Furthermore, CA-4 inhibits the polymerisation of tubulin into microtubules by interacting at the colchicine binding site. CA-4 is also known to target the vascular system of solid tumours thereby stopping blood flow, causing rapid necrosis.

A water-soluble phosphate prodrug of CA-4, fosbretabulin, is currently in phase III clinical development in the treatment of thyroid cancer, in phase II clinical development in small-cell lung cancers, and in treatments of cisplatin-resistant ovarian cancers. Similarly, the hydrochloride of the amine analogue of CA-4, ombrabulin, is used clinically in the treatment of advanced soft tissue sarcomas.

Although the mechanism of action of fosbretabulin and ombrabulin has not yet been fully elucidated, studies show that these vascular disrupting agents (VDAs) target tubulin at the colchicine site. They inhibit the polymerisation of endothelial cell tubulin by preventing the formation of microtubules causing a morphological change in endothelial cells that become rounder and detach from the vessel walls, causing thrombosis. The result is a cessation of blood flow, resulting in rapid necrosis, particularly marked in the central region of tumours, which is generally resistant to conventional therapies. Despite the appeal of these antivascular agents in antitumour chemotherapy, their administration is frequently accompanied by deleterious adverse effects linked to neuro- and cardiotoxicity in many patients, prohibiting the treatment in patients suffering from arrhythmias, uncontrolled hypertension or infarction, but also in asymptomatic patients.

Unlike conventional antimitotic agents (Vinca alkaloids, taxanes and colchicine), fosbretabulin and ombrabulin exert their antivascular action at doses well below the maximum tolerated dose and therefore have a wider therapeutic window. However, VDAs induce in monotherapy a central necrosis associated in the periphery with the persistence of a ring of viable cancer cells at the origin of tumour reactivation. These results justify the very promising clinical trials combining a VDA with a conventional chemotherapeutic agent for a synergistic effect. However, if fosbretabulin and ombrabulin are used clinically, they are nevertheless burdened with a major disadvantage, namely chemical instability attributable to isomerisation of the Z double bond leading to the inactive E isomer, thus requiring storage at low temperature and away from light.

A means of circumventing the recurrent problem of instability of the Z double bond of CA-4 was developed in application WO 2008/122620. Isocombretastatin A-4 (isoCA-4) and isoaminocombretastatin A-4 (isoNH$_2$CA-4) have been identified as two leading compounds whose biological profile (cytotoxicity, inhibition of tubulin polymerisation, induction of apoptosis, etc.) is exactly identical to that of the natural molecule, without however presenting the risk of isomerisation of the double bond. These molecules are particularly stable and do not metabolise in the presence of hepatocytes. Use of the two water-soluble prodrugs isoCA-4 and isoNH$_2$CA-4 induced, in nude mice xenografted by the human colon tumour cell line LS174T, a significant reduction in vascular density around the tumour comparable to that observed for ombrabulin, taken as control.

In terms of tumour efficacy, a synergistic effect of isoCA-4 in combination with gemcitabine has also been shown in a multifunctional nanoparticle formulation (*ACS Nano* 2014, 8, 2018). The antitumour efficacy of these isoCA-4/SQ-gem nanomedicines containing two antitumour active principles having different mechanisms of action was evaluated in vivo in a human tumour xenograft nude mice model (LS-174T). It was shown that at a dose of 21 μmol/kg and compared with different controls, the isoCA-4/SQ-gem nanoparticle led to nearly complete tumour regression (93%) in the mice and showed no toxicity to the animals after several weeks.

On the other hand, the human epigenome, which corresponds to all the modifications involved in gene regulation, is, unlike genetic inheritance, variable and controls the regions of DNA that are active. The human genome is wound around an axis constituted by histones, which are modified by enzymes with groups such as acetyl and methyl. Both the modifications and the histone wrapping determine which genes (DNA fragments) are active and which are not.

Histone acetylation is an integral part of regulation of gene transcription and is tightly controlled in normal cells. Two key enzymes play a major role in this acetylation phenomenon: histone acetyltransferases (HATs) and histone deacetylases (HDACs). Changes in the behaviour of these two types of epigenetic enzymes, HAT and HDAC, appear to play a role in the development of many cancers by inducing activation of an inappropriate group of genes. Readjusting the HDAC/HAT balance is a proven antitumour strategy and has led to the development of a family of drugs called HDAC inhibitors (HDACi), which currently top the list of antitumour medications.

In general, abnormal acetylation is linked to chromatin condensation and to repression of transcription, whereas hyperacetylation decompacts chromatin and activates transcription.

Inhibiting histone deacetylase (HDAC) activity induces hyperacetylation, changes in gene expression and, ultimately, differentiation, cell cycle arrest and tumour cell death. HDACi can regress blood cancers such as leukaemias and lymphomas, but also solid tumours such as prostate, colon and kidney tumours. For example, vorinostat or SAHA (ATU in France), an HDAC inhibitor, is indicated for the treatment of refractory cutaneous T-cell lymphoma.

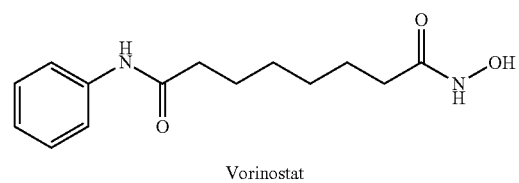 [SMILES: O=C(CCCCCCC(=O)Nc1ccccc1)NO]

Vorinostat

Therefore, much research has been done in the development of antitumour agents used in combination to obtain optimal results. HDAC inhibitor activity can be synergistic or additive with different antitumour agents in both hematologic and solid malignancies. The compounds of the present invention have shown activity both as HDAC inhibitors and as antivascular agents. The targeted molecules will comprise on the one hand a 1,1'-diarylethylene or 1,1'-arylheteroarylethylene or 1,1'-diheteroarylethylene unit, responsible for inhibiting the polymerisation of tubulin into microtubules, and on the other hand, on said unit, a grafted functionality responsible for inhibiting histone deacetylases (HDACs).

These two pharmacophores will be linked by a stable covalent bond that is not "cleavable" in vitro. These compounds have nanomolar cytotoxic activities on various human cancer lines also including lines resistant to usual treatments.

DISCLOSURE OF THE INVENTION

The present invention relates to novel compounds having the following formula (I):

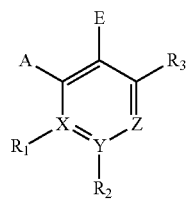

wherein:
$R_2$ and $R_3$ are different and one of $R_2$ and $R_3$ represents a group $A_1$ having the following general formula:

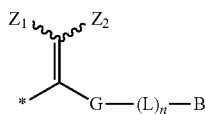

wherein:
B represents a zinc chelating group;
n represents an integer selected from 0 or 1;
L represents:
—$(CH_2)_r$—;
—CH=CH—$(CH_2)_r$—;
—CH=CH—CH=CH—$(CH_2)_r$—;
—C=C—CH=CH—$(CH_2)_r$—;
—C≡C—$(CH_2)_r$—;
—C≡C—CH=CH—$(CH_2)_r$—;
where r is an integer from 0 to 6, preferably from 0 to 4;
$Z_1$ represents a hydrogen atom, a halogen atom;
$Z_2$ represents an atom selected from a hydrogen, a halogen, a group selected from a nitrile, and a group B, provided that if $Z_2$=B then group -$(L)_n$-B is absent from G;
the bonds ⌇ mean that the double bond bearing $Z_1$, respectively, $Z_2$ is of E or Z stereochemistry;
* is the carbon atom bearing $R_2$ or $R_3$;
G represents a phenyl or a heteroaryl:
When G is a phenyl, it is substituted by a group $R_{20}$ selected from OMe and SMe in the para position, relative to the position of the double bond bearing $Z_1$ and $Z_2$;
When G is a heteroaryl, it is selected from pyridines, indoles, 1-methylindoles, indolines, carbazoles, benzothiophenes and benzofurans;
the other among $R_2$ and $R_3$ represents:
an OMe group, when X=Y=Z is a carbon atom;
when one of X, Y, Z is a nitrogen atom;
a hydrogen atom;
a halogen atom;
a hydroxyl group;
a nitrile group;
a group —$COYR_{10}$ with Y denoting O or N and $R_{10}$ denoting H or a ($C_1$ to $C_6$)alkyl group, a ($C_2$ to $C_4$)alkenyl group, a ($C_2$ to $C_4$)alkynyl group;
a group —$SO_2NR_{10}R_{11}$ with $R_{10}$, $R_{11}$ each independently denoting H or a ($C_1$ to $C_6$)alkyl group, a ($C_2$ to $C_4$)alkenyl group, a ($C_2$ to $C_4$)alkynyl group;
a group —$NHSO_2R_{12}$ with $R_{12}$ denoting a ($C_1$ to $C_6$)alkyl group, a ($C_2$ to $C_4$)alkenyl group, a ($C_2$ to $C_4$)alkynyl group, an aryl group, a heteroaryl group;
a ($C_1$ to $C_6$)alkyl group;
a ($C_2$ to $C_4$)alkenyl group;
a ($C_2$ to $C_4$)alkynyl group;
a ($C_1$ to $C_6$)alkoxy group; or
a group —$NR_{13}R_{14}$ with $R_{13}$ and $R_{14}$ independently representing a hydrogen or a ($C_1$ to $C_6$)alkyl group;
X, Y and Z independently represent a carbon or nitrogen atom provided that if X and Z represent a nitrogen atom, Y represents a carbon atom;
E represents:
a hydrogen atom, an —OMe group, when X=Y=Z=carbon and $R_2$=$A_1$,
a hydrogen atom, a halogen atom, when X=Y=Z=carbon and $R_3$=$A_1$,
a hydrogen atom, a halogen atom, a nitrile group, when one of X, Y or Z=nitrogen;
A represents:
an —OMe group, when X=Y=Z=carbon;
a hydrogen atom, a halogen atom, a nitrile group, when one of X, Y or Z=nitrogen;
$R_1$ represents:
a hydrogen atom, an —OMe group, when X=Y=Z=carbon and $R_3$=$A_1$,
a hydrogen atom, a halogen atom, when X=Y=Z=carbon and $R_2$=$A_1$,
a hydrogen atom, a halogen atom, a nitrile group, when one of X, Y or Z=nitrogen;
or else,
A and E together are part of a fused aromatic ring having the following formula:

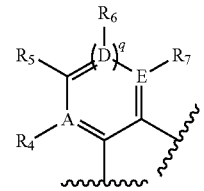

Then A, E, D represent:
a carbon or nitrogen atom;
$R_1$, $R_4$, $R_5$, $R_6$, $R_7$, if present, independently represent:
a hydrogen atom;
a halogen atom;
a hydroxyl group;
a ($C_1$ to $C_6$)alkyl group;
a ($C_2$ to $C_4$)alkenyl group;
a ($C_2$ to $C_4$)alkynyl group;
a ($C_1$ to $C_6$)alkoxy group; or
a group —$NR_{13}R_{14}$ with $R_{13}$ and $R_{14}$ independently representing a hydrogen or a ($C_1$ to $C_6$)alkyl group;
q represents an integer between 0 and 2;
and at least one of A, D, E, X, Y and Z represents a nitrogen atom provided that if X and Z represent a nitrogen atom, Y represents a carbon atom;
as well as the pharmaceutically acceptable salts, stereoisomers and antigen conjugation prodrugs thereof, with the exception of the compound having the following formula:

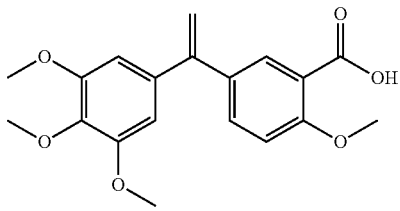

DESCRIPTION OF THE FIGURES

FIG. 1 shows the percentage inhibition of control values (M) at a test concentration of $1.0^{-5}$ M.

FIG. 2 shows the percentage of control values as a function of the logarithm of the concentration (M) of compound 2.

FIG. 3 shows the percentage of control values as a function of the logarithm of the concentration (M) of compound 2.

FIG. 4 shows the percentage inhibition of control values (M) at a test concentration of $1.0^{-5}$ M.

FIG. 5 shows the percentage of control values as a function of the logarithm of the concentration (M) of compound 3.

FIG. 6 shows the percentage inhibition of control values (M) at a test concentration of $1.0^{-5}$ M.

FIG. 7 shows the percentage inhibition of control values (M) at a test concentration of $1.0^{-5}$ M.

FIG. 8 shows the percentage inhibition of control values (M) at a test concentration of $1.0^{-5}$ M.

DEFINITIONS

Figure 1:
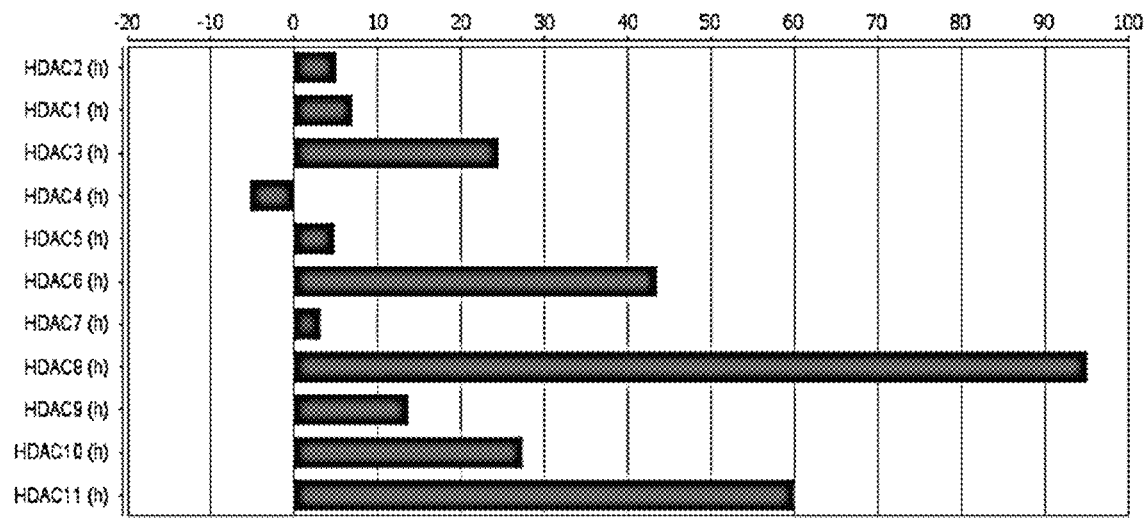
FIG. 1 describes the inhibitory potential of molecule 2 with respect to HDACs 1 to 11, with more particularly selective activity for HDAC8 and HDAC11. More particularly.

The term "halogen", as used in the description of the present invention, means fluorine, chlorine, bromine and iodine atoms. Advantageously, it will be fluorine, bromine and chlorine, and more advantageously fluorine or chlorine. The term "($C_1$ to $C_6$)alkyl", as used in the description of the present invention, means any linear or branched saturated hydrocarbon group having 1 to 6 carbon atoms, in particular methyl, ethyl, n-propyl, isopropyl, n-butyl, iso-butyl, sec-butyl, tert-butyl, pentyl and hexyl groups. The term "($C_2$ to $C_4$)alkenyl", as used in the description of the present invention, means any linear or branched hydrocarbon group having 2 to 4 carbon atoms and at least one double bond, such as a vinyl (ethenyl) group.

The term "($C_2$ to $C_4$)alkynyl", as used in the description of the present invention, means any linear or branched hydrocarbon group having 2 to 4 carbon atoms and at least one triple bond, such as an ethynyl or propynyl group. The term "($C_1$ to $C_6$)alkoxy", as used in the description of the present invention, means any —O-alkyl group, alkyl being as defined above. Examples of alkoxy groups include methoxy, ethoxy, propoxy, n-butoxy, iso-butoxy and tert-butoxy groups.

The term "(het)Aryl", as used in the description of the present invention, means an aryl or heteroaryl. The term "aryl", as used in the description of the present invention, means one or more aromatic rings having 5 to 10 carbon atoms, which may be fused. In particular, the aryl groups may be monocyclic or bicyclic groups, such as phenyl or naphthyl.

Advantageously, the aryl group is a phenyl. The term "heteroaryl", as used in the description of the present invention, means an aromatic group having 5 to 10 ring atoms. Ring atoms include carbon atoms and one or more heteroatoms, such as sulphur, nitrogen or oxygen atoms, for example. The heteroaryl of the present invention may consist of one or two fused rings. Preferably, the heteroaryl group will be an indolyl, benzothiophenyl, benzofuranyl or benzoimidazolyl group. The term nitrile, as used in the description of the present invention, means a —CN group. The formula "—COYR'", as used in the description of the present invention, means an acid or an ester when Y is O, an amide when Y is N. The formula "—SO$_2$NR'R''" or "—NHSO$_2$R'", as used in the description of the present invention, means a sulphonamide. The expression "pharmaceutically acceptable", as used in the description of the present invention, means that which is useful in the preparation of a pharmaceutical composition, which is generally safe, non-toxic and neither biologically nor otherwise undesirable and which is acceptable for veterinary and/or human pharmaceutical use. The expression "pharmaceutically acceptable salts", as used in the description of the present invention, means salts of a compound which are pharmaceutically acceptable, as defined herein, and which possess the desired pharmacological activity of the parent compound. Such salts include:

(1) hydrates and solvates, (2) acid addition salts formed with inorganic acids such as hydrochloric acid, hydrobromic acid, sulphuric acid, nitric acid, phosphoric acid and the like; or formed with organic acids such as acetic acid, benzenesulphonic acid, benzoic acid, camphosulphonic acid, citric acid, ethanesulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and the like.

Advantageously, it is hydrochloric acid; or (3) salts formed when an acidic proton present in the parent compound is either replaced by a metal ion, for example an alkali metal ion, an alkaline earth metal ion; or coordinates with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide. Advantageously, the acidic proton is displaced by a Na$^+$ ion, notably by using sodium hydroxide. Acid addition salts are formed in particular with an amine function or with a pyridine. Base addition salts are formed in particular with a carboxylic acid (—COOH), phosphate (—OP(O)(OH)$_2$) or sulphate (—OSO$_3$H) function.

The term "stereoisomers", as used in the description of the present invention, means diastereoisomers or enantiomers. These are therefore configurational isomers. Stereoisomers that are not mirror images of each other are thus referred to as "diastereomers", and stereoisomers that are non-superimposable mirror images of each other are referred to as "enantiomers", also called "optical isomers". A carbon atom linked to four non-identical substituents is called a "chiral centre". When a molecule has such a chiral centre, it is referred to as chiral and has two enantiomeric forms. When a molecule has several chiral centres, then it will have several diastereoisomeric and enantiomeric forms. An equimolar mixture of two enantiomers is called a racemic mixture.

The expression "compounds of the present invention" or "compounds having formula (I)", as used in the present description, means compounds having formula (I), but also more precise formulas (II), and (III), as defined in detail below.

DETAILED DESCRIPTION OF THE INVENTION

The inventors have demonstrated that the compounds of the present invention have activity both as HDAC inhibitors and as antivascular agents. The targeted molecules will comprise on the one hand a 1,1'-diarylethylene or 1,1'-arylheteroarylethylene or 1,1'-diheteroarylethylene unit, responsible for inhibiting the polymerisation of tubulin into microtubules, and on the other hand, on said unit, a grafted functionality responsible for inhibiting histone deacetylases (HDACs).

These two pharmacophores will be linked by a covalent bond that is not sensitive to hydrolysis. These compounds possess nanomolar cytotoxic activities on various human cancer lines also including lines resistant to usual treatments.

Compounds of the Present Invention

The invention relates to the compounds having the following formula (I):

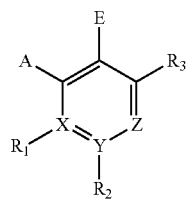

(I)

wherein:
R$_2$ and R$_3$ are different and one of R$_2$ and R$_3$ represents a group A$_1$ having the following general formula:

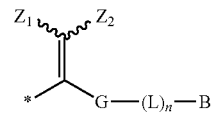

wherein:
B represents a zinc chelating group;
n represents an integer selected from 0 or 1;
L represents:
—(CH$_2$)$_r$—;
—CH=CH—(CH$_2$)$_r$—;
—CH=CH—CH=CH—(CH$_2$)$_r$—;
—C=C—CH=CH—(CH$_2$)$_r$—;
—C≡C—(CH$_2$)$_r$—;
—C≡C—CH=CH—(CH$_2$)$_r$—;
where r is an integer from 0 to 6, preferably from 0 to 4;
Z$_1$ represents a hydrogen atom, a halogen atom;
Z$_2$ represents an atom selected from a hydrogen, a halogen, a group selected from a nitrile, and a group B, provided that if Z$_2$=B then group -(L)$_n$-B is absent from G;
the bonds ⌇ mean that the double bond bearing Z$_1$, respectively, Z$_2$ is of E or Z stereochemistry;
* is the carbon atom bearing R$_2$ or R$_3$;
G represents a phenyl or a heteroaryl:
When G is a phenyl, it is substituted in the para position by a group R$_{20}$ selected from OMe and SMe, relative to the position of the double bond bearing Z$_1$ and Z$_2$;
When G is a heteroaryl, it is selected from pyridines, indoles, 1-methylindoles, indolines, carbazoles, benzothiophenes and benzofurans;
the other among R$_2$ and R$_3$ represents:
an OMe group, when X=Y=Z is a carbon atom;
when one of X, Y, Z is a nitrogen atom;
a hydrogen atom;
a halogen atom selected from fluorine, chlorine and bromine, preferably a chlorine atom;
a hydroxyl group;
a nitrile group;
a group —COYR$_{10}$ with Y denoting O or N and R$_{10}$ denoting H or a (C$_1$ to C$_6$)alkyl group, a (C$_2$ to C$_4$)alkenyl group, a (C$_2$ to C$_4$)alkynyl group;
a group —SO$_2$NR$_{10}$R$_{11}$ with R$_{10}$, R$_{11}$ each independently denoting H or a (C$_1$ to C$_6$)alkyl group, a (C$_2$ to C$_4$)alkenyl group, a (C$_2$ to C$_4$)alkynyl group;
a group —NHSO$_2$R$_{12}$ with R$_{12}$ denoting a (C$_1$ to C$_6$)alkyl group, a (C$_2$ to C$_4$)alkenyl group, a (C$_2$ to C$_4$)alkynyl group, an aryl group, a heteroaryl group;
a (C$_1$ to C$_6$)alkyl group;
a (C$_2$ to C$_4$)alkenyl group;
a (C$_2$ to C$_4$)alkynyl group;
a (C$_1$ to C$_6$)alkoxy group; or
a group —NR$_{13}$R$_{14}$ with R$_{13}$ and R$_{14}$ independently representing a hydrogen or a (C$_1$ to C$_6$)alkyl group;
X, Y and Z independently represent a carbon or nitrogen atom provided that if X and Z represent a nitrogen atom, Y represents a carbon atom;
E represents:
a hydrogen atom, an —OMe group, when X=Y=Z=carbon and R$_2$=A$_1$, a hydrogen atom, a halogen atom, when X═Y═Z═carbon and $R_3$═$A_1$,
a hydrogen atom, a halogen atom, a nitrile group, when one of X, Y or Z═nitrogen;

A represents:
an —OMe group, when X═Y═Z═carbon;
a hydrogen atom, a halogen atom, a nitrile group, when one of X, Y or Z═nitrogen;

$R_1$ represents:
a hydrogen atom, an —OMe group, when X═Y═Z═carbon and $R_3$═$A_1$,
a hydrogen atom, a halogen atom, when X═Y═Z═carbon and $R_2$═$A_1$,
a hydrogen atom, a halogen atom, a nitrile group, when one of X, Y or Z═nitrogen;

or else,
A and E together are part of a fused aromatic ring having the following formula:

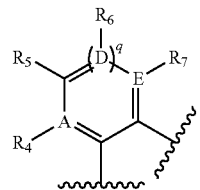

Then A, E, D represent:
a carbon or nitrogen atom;
$R_1$, $R_4$, $R_5$, $R_6$, $R_7$, if present, independently represent:
a hydrogen atom;
a halogen atom selected from fluorine, chlorine and bromine, preferably a chlorine;
a hydroxyl group;
a ($C_1$ to $C_6$)alkyl group;
a ($C_2$ to $C_4$)alkenyl group;
a ($C_2$ to $C_4$)alkynyl group;
a ($C_1$ to $C_6$)alkoxy group; or
a group —$NR_{13}R_{14}$ with $R_{14}$ and $R_{14}$ independently representing a hydrogen or a ($C_1$ to $C_6$)alkyl group;
q represents an integer between 0 and 2;
and at least one of A, D, E, X, Y and Z represents a nitrogen atom provided that if X and Z represent a nitrogen atom, Y represents a carbon atom;
as well as the pharmaceutically acceptable salts, stereoisomers and antigen conjugation prodrugs thereof,
with the exception of the compound having the following formula:

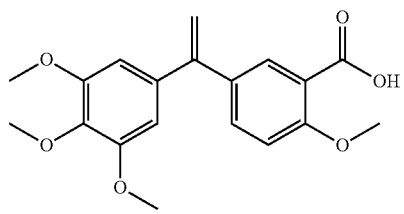 [SMILES: C=C(c1cc(OC)c(OC)c(OC)c1)c1ccc(OC)c(C(=O)O)c1]

The expression "$R_1$ $R_4$, $R_5$, $R_6$, $R_7$, if present", as used in the description of the present invention, means that groups $R_1$ $R_4$, $R_5$, $R_6$, $R_7$ will be present if the valence of the atom to which the group is, or would be, linked allows it. Persons skilled in the art will easily be able to determine if such a group is present.

In an embodiment, $R_1$ $R_4$, $R_5$, $R_6$, $R_7$ are identical and each represents a hydrogen atom.

In certain embodiments, when one of $R_2$ and $R_3$ represents a group $A_1$, then the other among $R_2$ and $R_3$ represents a hydrogen atom.

In other embodiments, when one of $R_2$ and $R_3$ represents a group $A_1$, then the other among $R_2$ and $R_3$ represents a chlorine atom.

In an embodiment, G is a phenyl.

In another embodiment, G represents a pyridine. In another embodiment, G represents an indole. In an additional embodiment, G represents a carbazole.

The zinc chelating groups B are advantageously selected from the list comprising the units having the following general formulas:

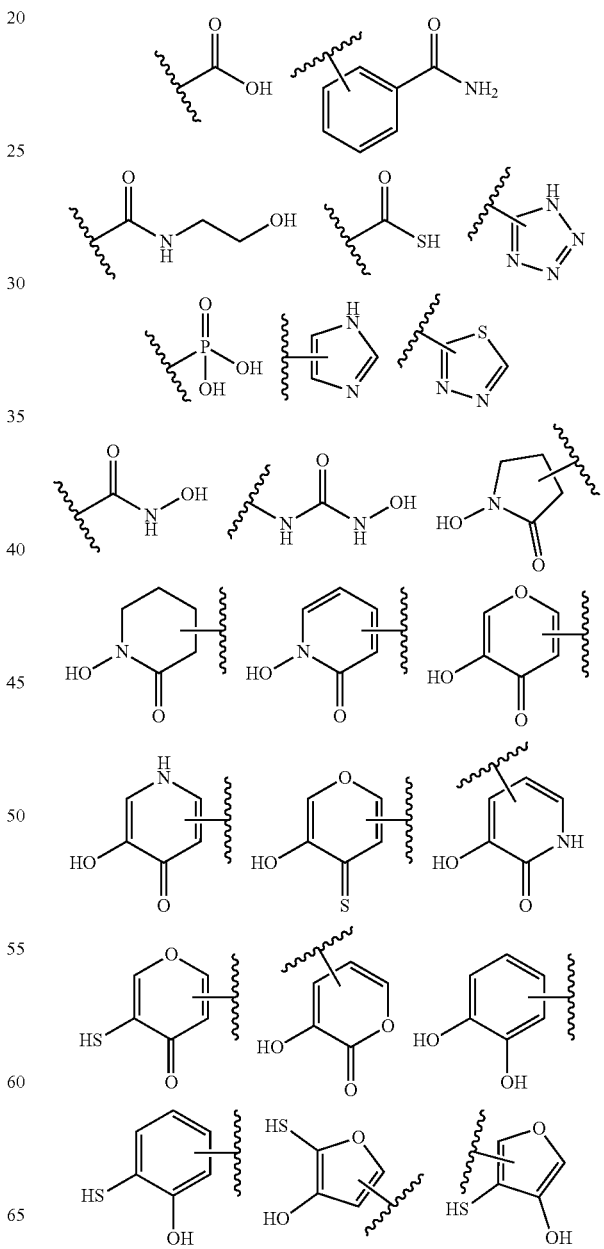

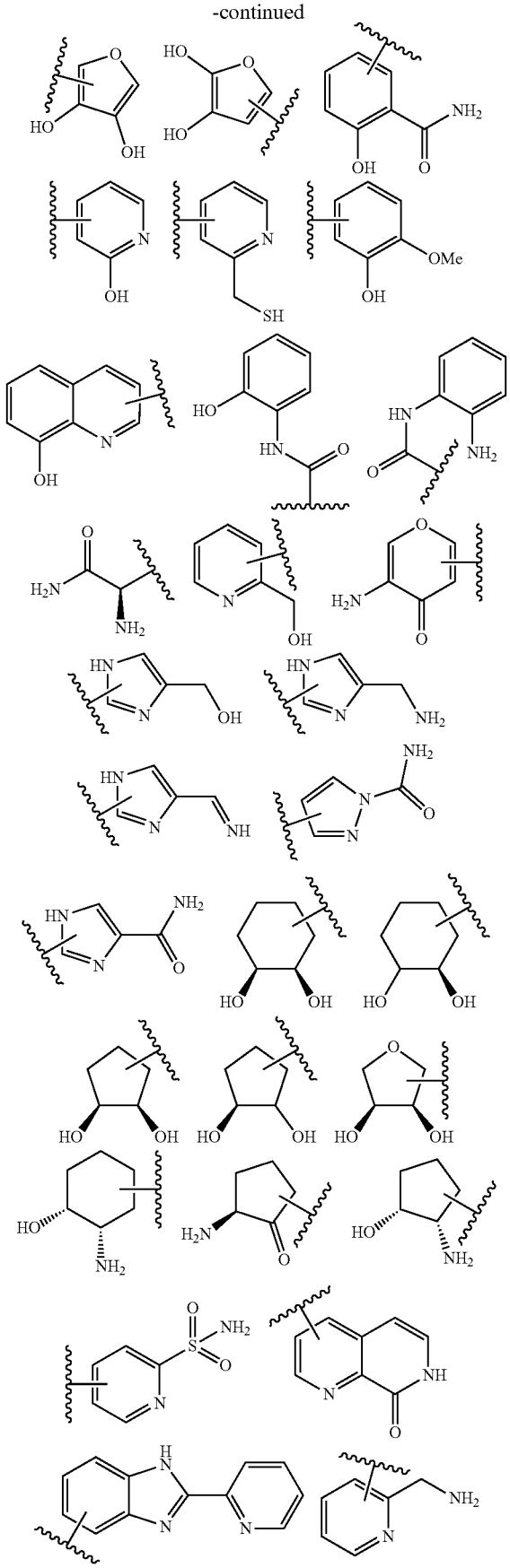
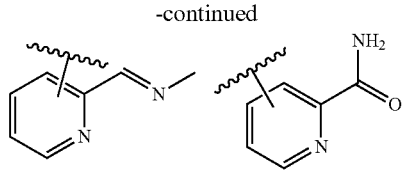
Preferably, the zinc chelating groups B are selected from the list comprising the units having the following general formulas:
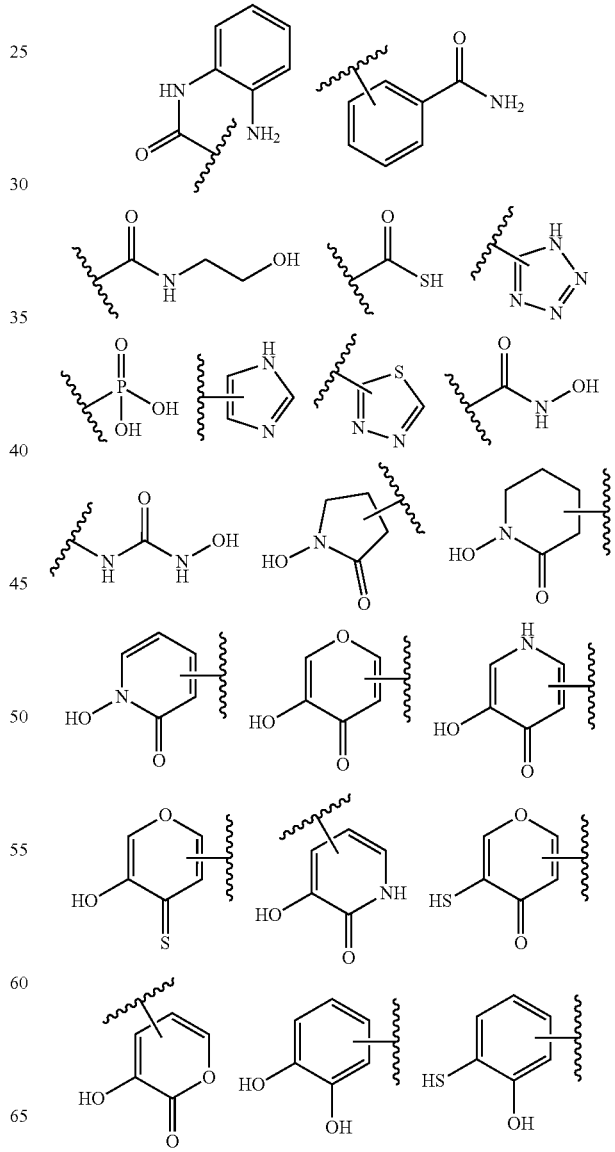

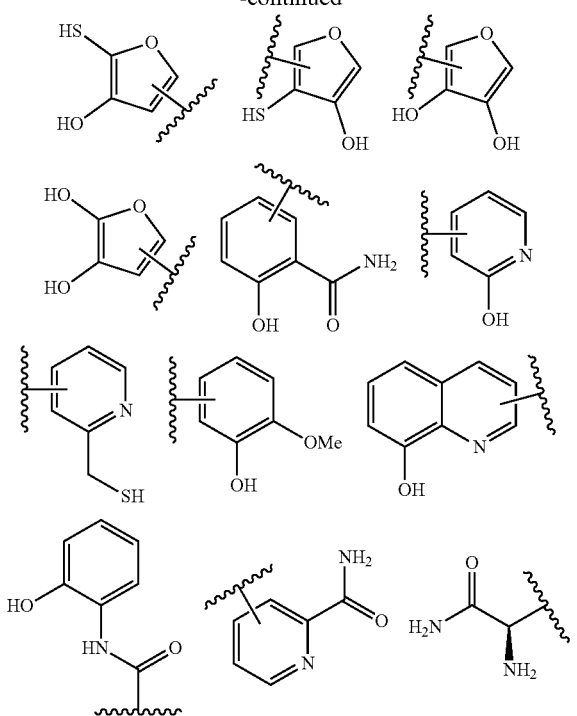
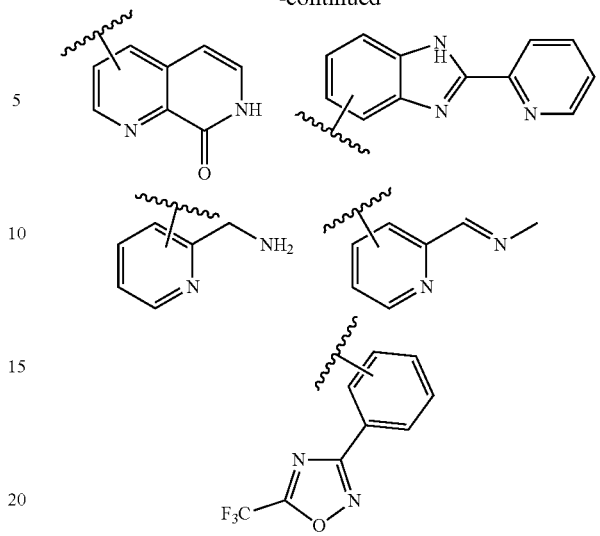

The zinc chelating group B more advantageously represents a group selected from an amide having the following general formula:

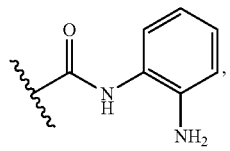

a hydroxamic acid, a carboxylic acid, a benzamide, an n-hydroxyethylformamide, a mercaptoketone, a tetrazole, a phosphonic acid, an imidazole, and a thiadiazole, preferably a hydroxamic acid, a benzamide, an n-hydroxyethylformamide, a mercaptoketone, a tetrazole, a phosphonic acid, an imidazole, a thiadiazole and

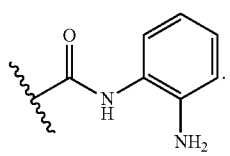 [SMILES: *C(=O)Nc1ccccc1N]

More particularly, group B is selected from an amide having the following general formula:

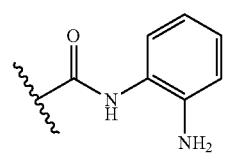

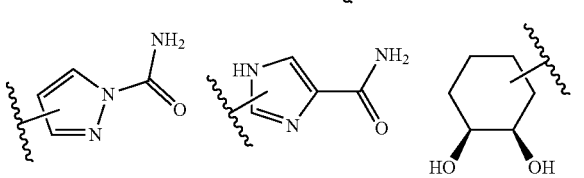
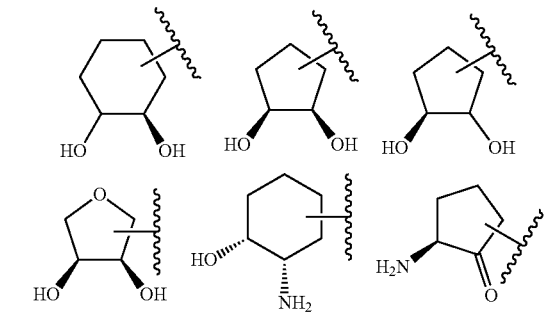
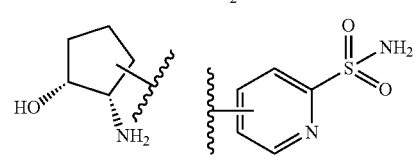

and a hydroxamic acid, more preferentially B is a hydroxamic acid group.

In a variant embodiment, n=0 and group B is then directly linked to group G.

In another variant, n=1 and L is then selected from the list as defined above.

The invention more particularly relates to the compound having the following general formula

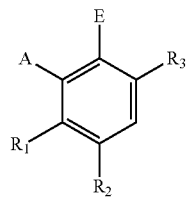

(II)

where $R_1$, $R_2$, $R_3$, A and E are as defined either above or in the particular variants and embodiments defined below.

The compound of the present invention advantageously has the following general formula:

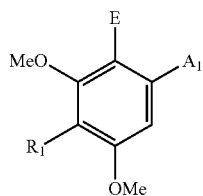

(II-a)

Where $R_1$, E, and group $A_1$ are as defined either above or in the particular variants and embodiments defined below.

In an embodiment, the compound of formula (II-a) is characterised in that $R_1$ represents an —OMe group, and E represents a hydrogen atom. In another embodiment, the compound of formula (II-a) is characterised in that $R_1$ represents an —OMe group and E represents a halogen atom, said halogen atom is selected from a bromine, chlorine, fluorine atom, more advantageously E is a chlorine atom.

In a variant embodiment, the compound having the general formula (II-a) is characterised in that $R_1$ and E are identical and each represents a hydrogen atom. In another variant, the compound having the general formula (II-a) is characterised in that $R_1$ represents a hydrogen atom and E represents a chlorine atom.

The invention also relates to the compound having the following general formula:

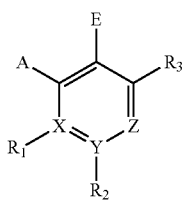

(III)

wherein:
X, Y, Z each independently represent a nitrogen atom or a carbon atom, and; A, E, $R_1$, $R_2$ and $R_3$ are as defined either above or in the particular variants and embodiments defined below.

The invention more particularly relates to the compound having the following general formula

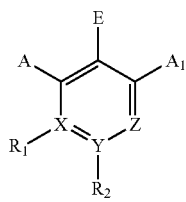

(III-a)

where
X, Y and Z independently represent a carbon or nitrogen atom provided that if X and Z represent a nitrogen atom, Y represents a carbon atom and;
$R_2$ and $R_3$ are as defined either above or in the particular variants and embodiments defined below.
E represents a hydrogen atom, a halogen atom selected from fluorine, bromine, chlorine, or a nitrile group;
A represents a hydrogen atom, a halogen atom selected from fluorine, bromine, chlorine, a nitrile group;
$R_1$ represents a hydrogen atom, a halogen atom selected from fluorine, bromine, chlorine, a nitrile group.

In an embodiment, the composition advantageously has the following general formula:

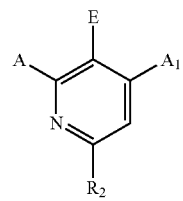

(III-a1)

where $A_1$ is as defined either above or in the particular variants and embodiments defined below, and A, E, $R_2$ are as defined above for the compound having formula (III-a).

In a variant embodiment, the compound having formula (III-a1) is characterised in that A, E and $R_2$ are identical and each represents a hydrogen atom.

In an additional variant embodiment, the compound having the general formula (III-a1) is characterised in that $R_2$ represents a methyl group, and A, E are identical and each represents a hydrogen atom.

In another variant embodiment, the compound having the general formula (III-a1) is characterised in that $R_2$ represents a nitrile group, and A, E are identical and each represents a hydrogen atom.

In another variant embodiment, the compound having the general formula (III-a1) is characterised in that $R_2$ represents a chlorine atom and A, E are identical and each represents a hydrogen atom.

In an additional variant, the compound having the general formula (III-a1) is characterised in that $R_2$ represents an —OMe group and A, E are identical and each represents a hydrogen atom.

In another particular embodiment, the composition advantageously has the following general formula:

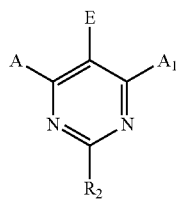

(III-a2)

where $A_1$ is as defined either above or in the particular variants and embodiments defined below, and A, E, $R_2$ are as defined above for the compound having formula (III-a).

In another variant embodiment, the compound having formula (III-a2) is characterised in that A, E and $R_2$ are identical and each represents a hydrogen atom.

In an additional variant embodiment, the compound having the general formula (III-a2) is characterised in that $R_2$ represents a methyl group, and A, E are identical and each represents a hydrogen atom.

In another variant embodiment, the compound having the general formula (III-a2) is characterised in that $R_2$ represents a nitrile group, and A, E are identical and each represents a hydrogen atom.

In another variant embodiment, the compound having the general formula (III-a2) is characterised in that $R_2$ represents a chlorine atom and A, E are identical and each represents a hydrogen atom.

In an additional variant, the compound having the general formula (III-a2) is characterised in that $R_2$ represents an —OMe group and A, E are identical and each represents a hydrogen atom.

The invention also relates to the compound having the following general formula:

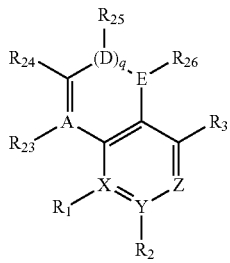

(III-b)

where at least one of A, D, E, X, Y and Z represents a nitrogen atom, provided that if X and Z represent a nitrogen atom, Y represents a carbon atom and;

q, $R_2$, $R_3$ and $R_1$, $R_4$, $R_5$, $R_6$, $R_7$, if present, are as defined either above or in the variants and embodiments defined below.

In a preferred embodiment, the compound of the present invention has the general formula (III-b), where $R_3=A_1$.

In an embodiment, the composition advantageously has the following general formula:

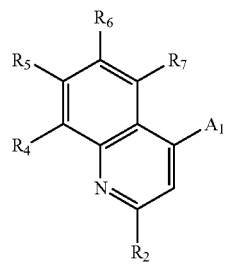

(III-b1)

where $A_1$, and $R_2$, $R_4$, $R_5$, $R_6$, $R_7$, are as defined above for the compound having the general formula (III-b).

In another embodiment, the compound having the general formula (III-b1) is characterised in that $R_2$, $R_4$, $R_5$, $R_6$, $R_7$ are identical and each represents a hydrogen atom.

In an additional variant embodiment, the compound having the general formula (III-b1) is characterised in that $R_2$ represents a methyl group, and $R_4$, $R_5$, $R_6$, $R_7$ are identical and each represents a hydrogen atom.

In another variant embodiment, the compound having the general formula (III-b1) is characterised in that $R_2$ represents a nitrile group, and $R_4$, $R_5$, $R_6$, $R_7$ are identical and each represents a hydrogen atom.

In another variant embodiment, the compound having the general formula (III-b1) is characterised in that $R_2$ represents a chlorine atom and $R_4$, $R_5$, $R_6$, $R_7$ are identical and each represents a hydrogen atom.

In an additional variant, the compound having the general formula (III-b1) is characterised in that $R_2$ represents an —OMe group and $R_4$, $R_5$, $R_6$, $R_7$ are identical and each represents a hydrogen atom.

In another embodiment, the composition advantageously has the following general formula:

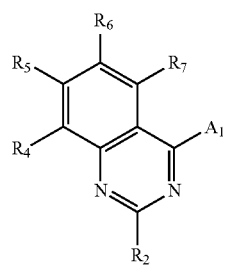

(III-b2)

where $A_1$, and $R_2$, $R_4$, $R_5$, $R_6$, $R_7$, are as defined above for the compound having the general formula (III-b).

In a particular embodiment, the compound having the general formula (III-b2) is characterised in that $R_2$, $R_4$, $R_5$, $R_6$, $R_7$ are identical and each represents a hydrogen atom.

In an additional variant embodiment, the compound having the general formula (III-b2) is characterised in that $R_2$ represents a methyl group, and $R_4$, $R_5$, $R_6$, $R_7$ are identical and each represents a hydrogen atom.

In another variant embodiment, the compound having the general formula (III-b2) is characterised in that $R_2$ represents a nitrile group, and $R_4$, $R_5$, $R_6$, $R_7$ are identical and each represents a hydrogen atom.

In another variant embodiment, the compound having the general formula (III-b2) is characterised in that $R_2$ represents a chlorine atom and $R_4$, $R_5$, $R_6$, $R_7$ are identical and each represents a hydrogen atom.

In an additional variant, the compound having the general formula (III-b2) is characterised in that $R_2$ represents an —OMe group and $R_4$, $R_5$, $R_6$, $R_7$ are identical and each represents a hydrogen atom.

In a preferred embodiment and regardless of the previous embodiment, the compounds of the present invention are characterised in that group $A_1$ is advantageously selected from the following groups having the general formulas:

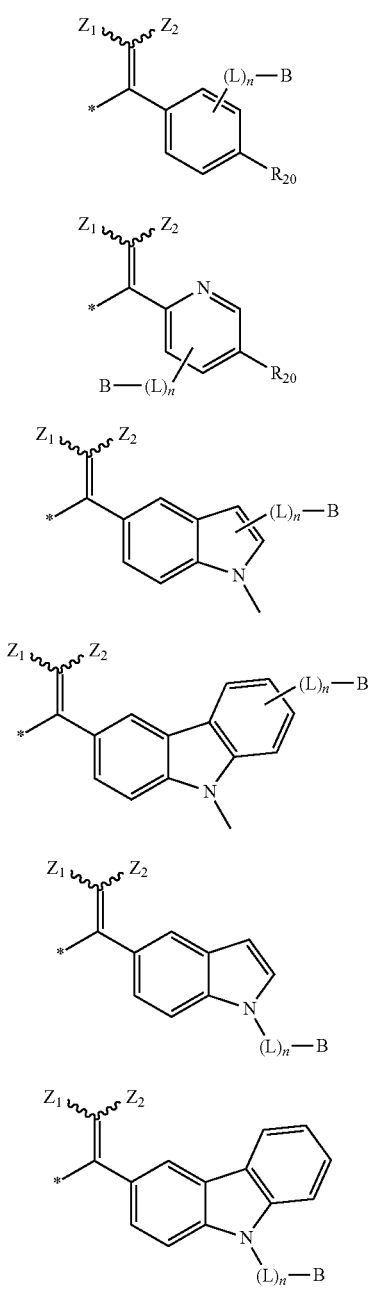

$Z_1$ and $Z_2$ each independently represent a hydrogen atom, a halogen atom selected from fluorine, chlorine and bromine, preferably fluorine, or a nitrile group;

$R_{20}$, B, L and n are as defined above, and;

the bonds ⌇ mean that the double bond bearing $Z_1$, respectively, $Z_2$ is of E or Z stereochemistry;

* is the carbon atom bearing $R_2$ or $R_3$.

Advantageously, $Z_1$ and $Z_2$ are identical and represent a hydrogen atom or a halogen atom selected from fluorine, chlorine, and bromine, preferably fluorine. More particularly, $Z_1$ and $Z_2$ are identical and each represents a hydrogen atom or a fluorine atom.

In a variant of the invention, $Z_1$ and $Z_2$ are different and independently represent a hydrogen atom and a nitrile group, and the compound of the present invention is in the form of a mixture of E or Z stereoisomers.

In an embodiment, for groups $A_1$-5 and $A_1$-6, n=1 and L advantageously represents —(CH$_2$), where r is an integer from 0 to 6, preferably 0 to 4.

In a variant embodiment, for groups $A_1$-1 to $A_1$-4, n=0. In another variant embodiment, for groups $A_1$-1 to $A_1$-4, n=1.

In another embodiment and regardless of the previous embodiment, the compounds of the invention are characterised in that group $A_1$ is selected from the groups having the following general formulas:

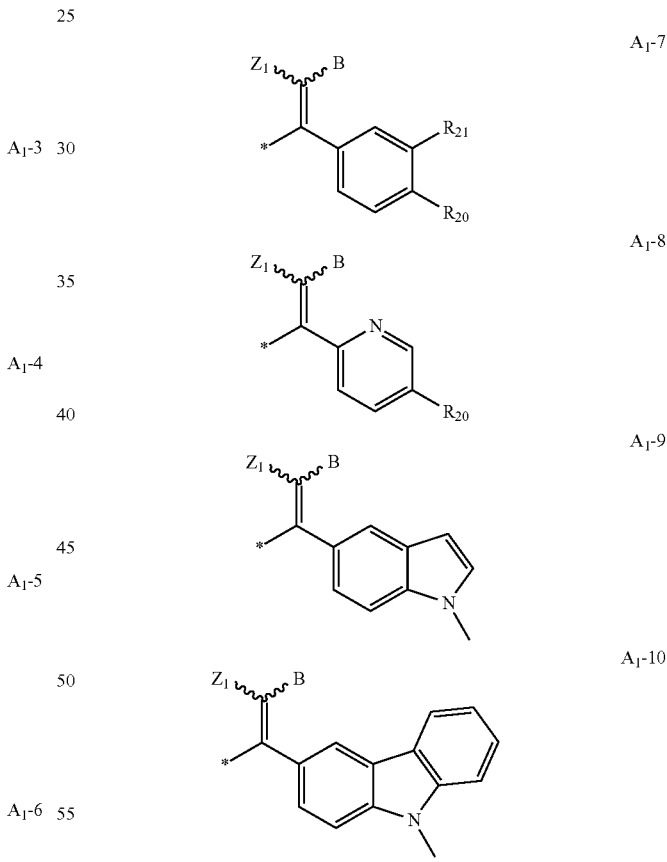

$Z_1$ represents a hydrogen atom, a halogen atom selected from fluorine, chlorine and bromine, preferably fluorine, or a nitrile group;

$R_{20}$, B, are as defined above;

$R_{21}$ represents a hydrogen atom, a group selected from —OH, —NH$_2$, F, N$_3$, —C≡CH, —C≡C(CH$_2$)$_m$OH, where m is an integer between 0 and 5, (E)-CH=CH=CH$_2$OH, (E)-CH=CHCOOR, where R is a hydrogen atom or a (C$_1$ to C$_4$)alkyl group, and;

the bonds ⌇ mean that the double bond bearing $Z_1$, respectively, $Z_2$ is of E or Z stereochemistry;

\* is the carbon atom bearing $R_2$ or $R_3$.

Regardless of group $A_1$ defined above, B represents more particularly a group selected from a hydroxamic acid and an amide having the following general formula:

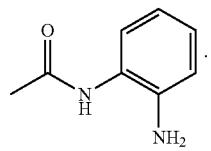

The compounds of the present invention are preferably selected from the following group:

1
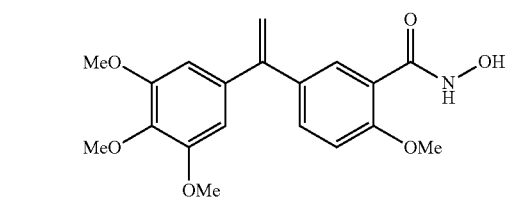

2
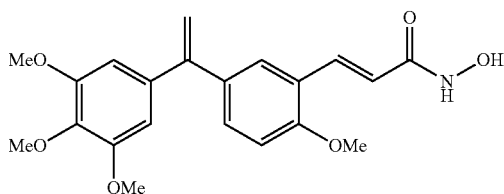

3
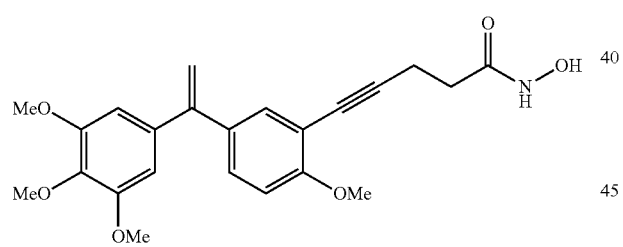

4
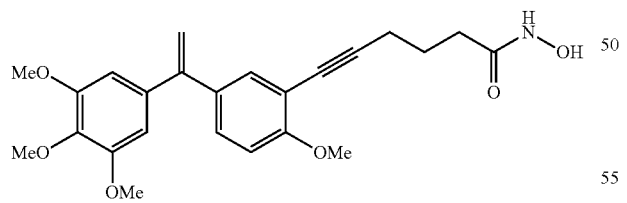

5
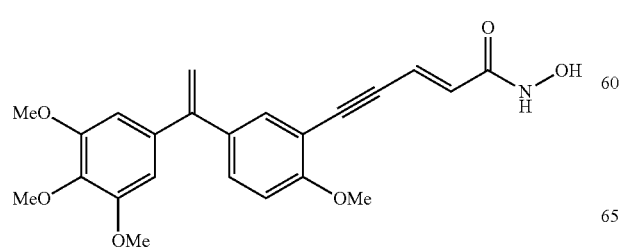

6
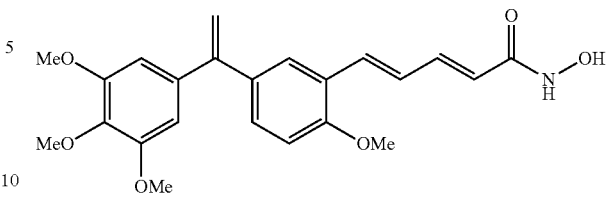

7

8
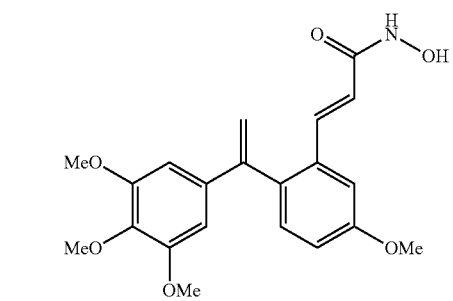

9
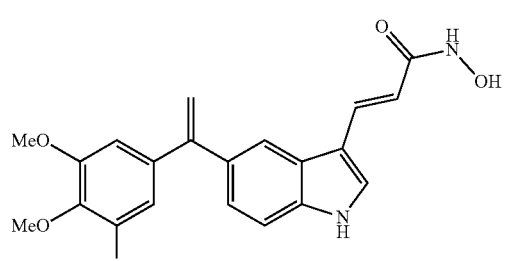

10
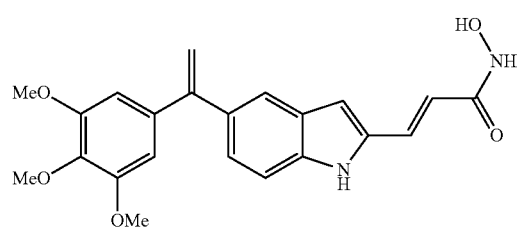

11
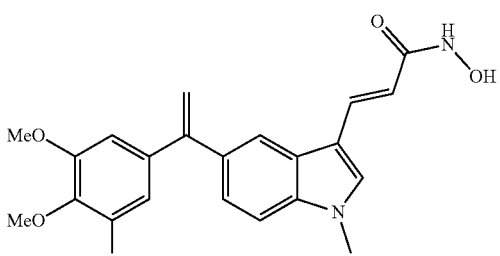

-continued
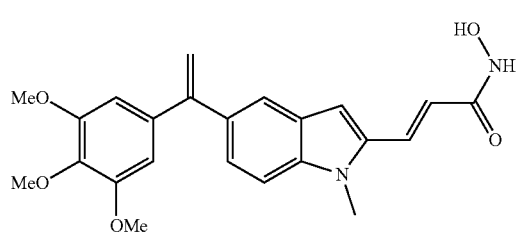
12
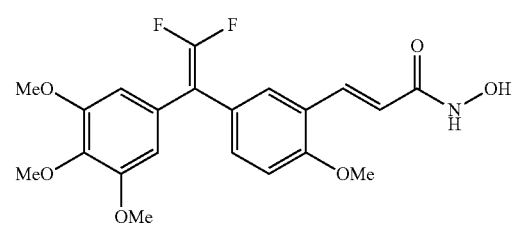
13
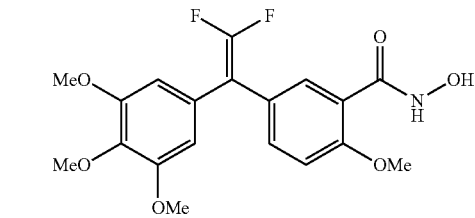
14
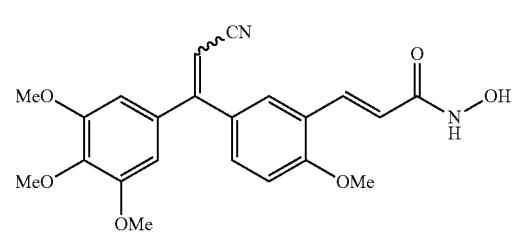
15
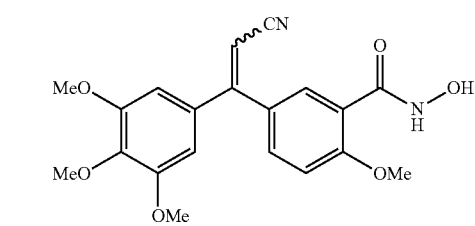
16
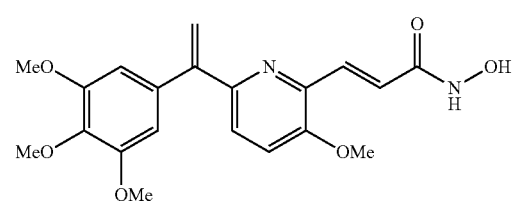
17
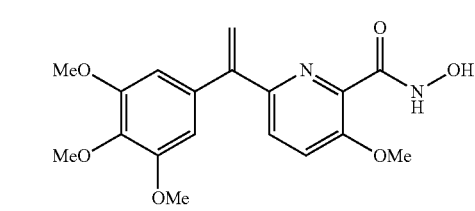
18
-continued
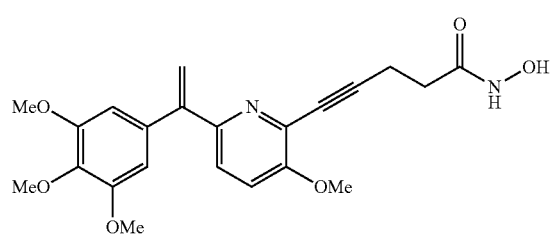
19
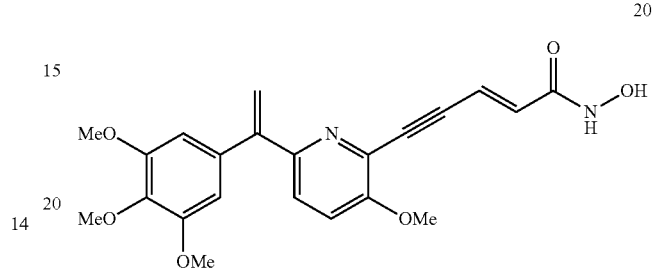
20
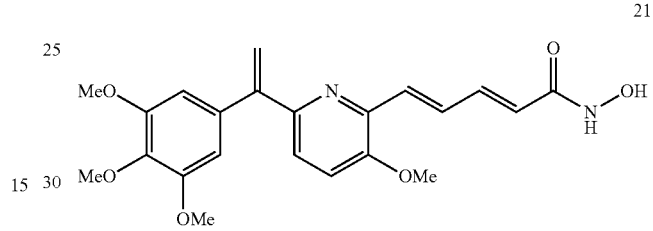
21
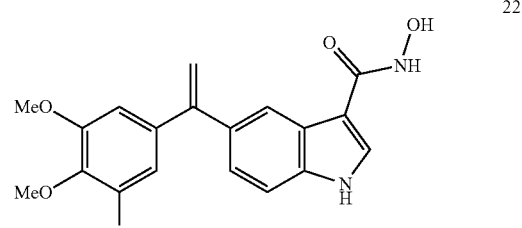
22
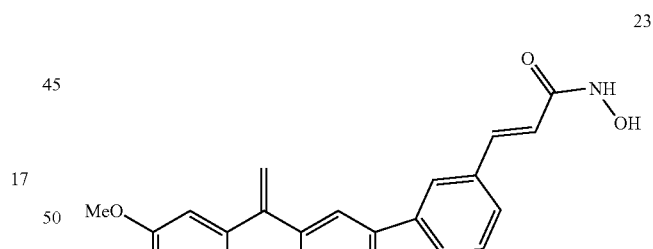
23
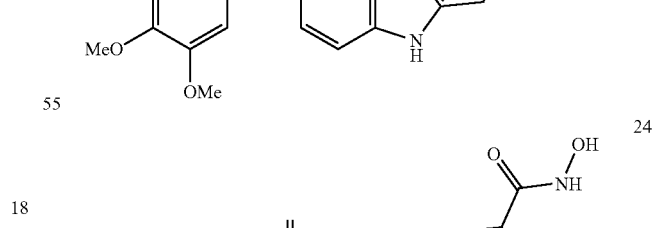
24

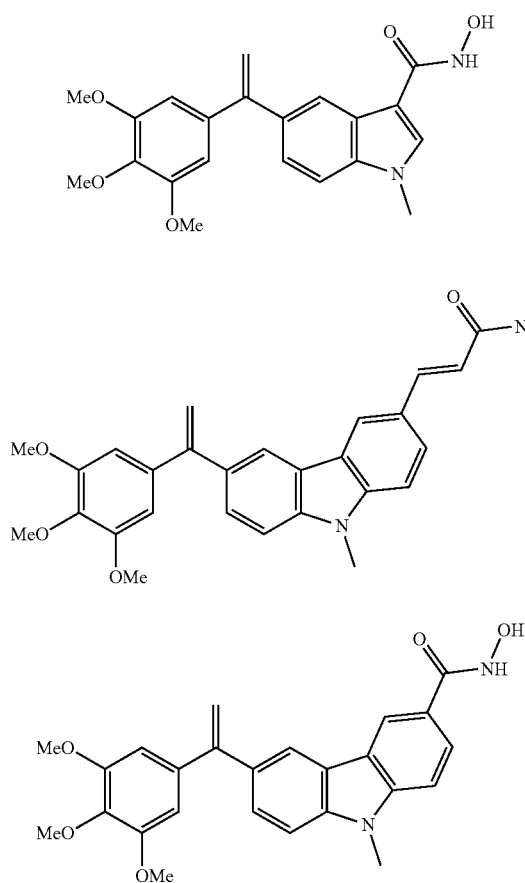
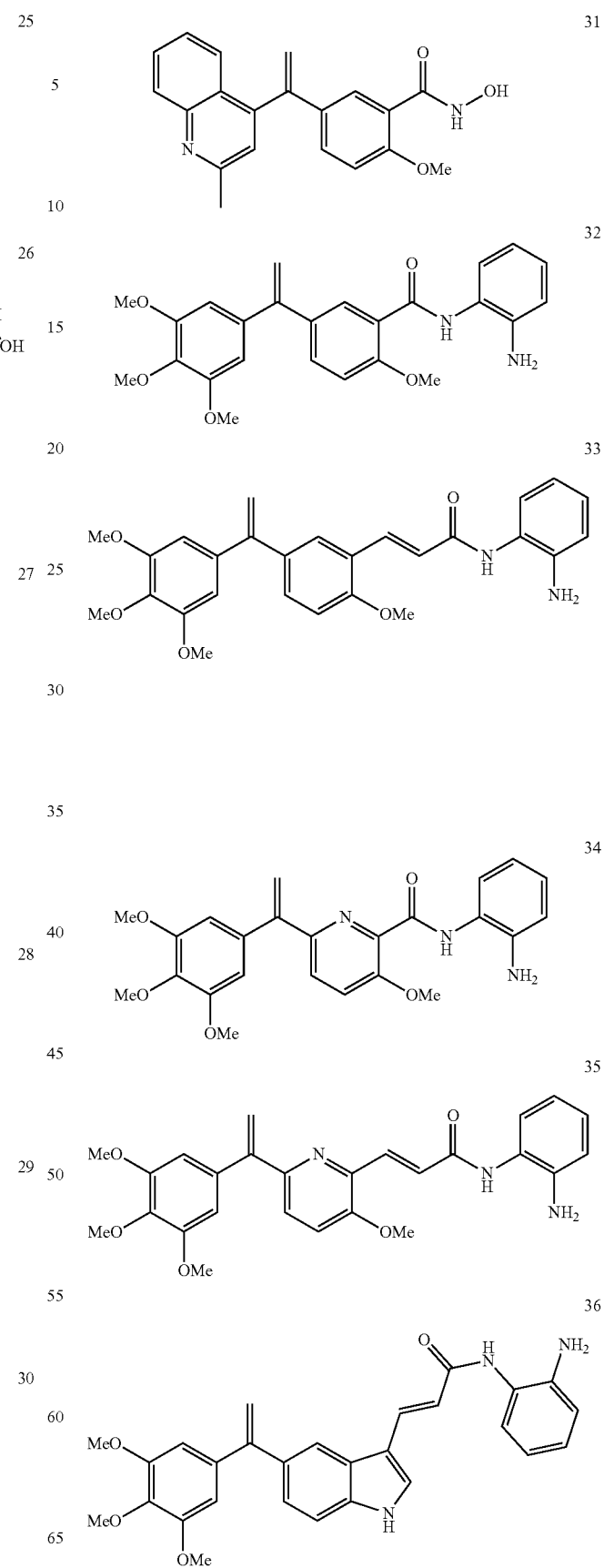

37
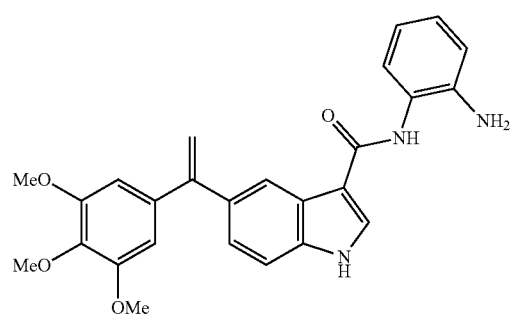
38
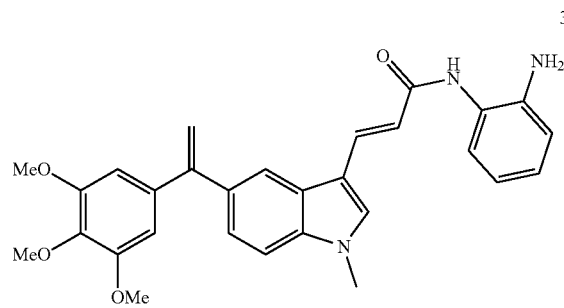
39
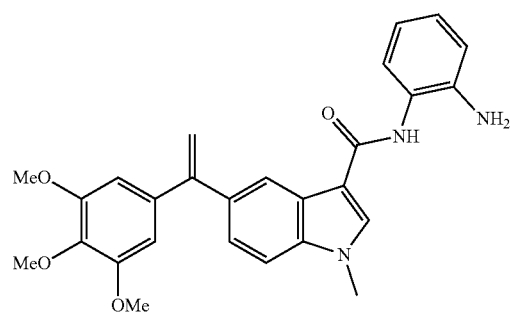
40
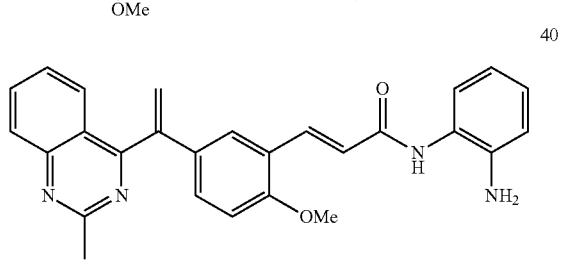
41
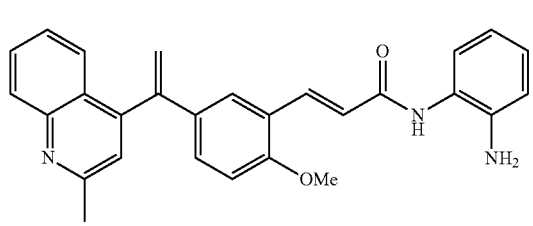
42
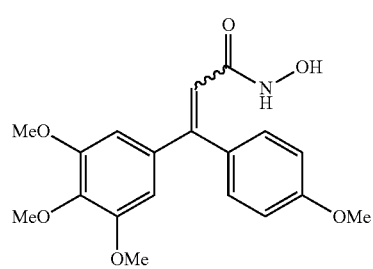
43
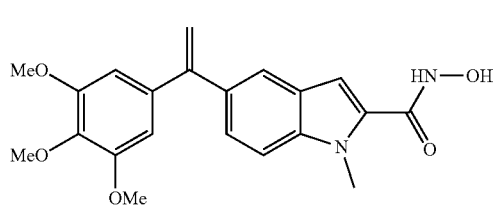
44
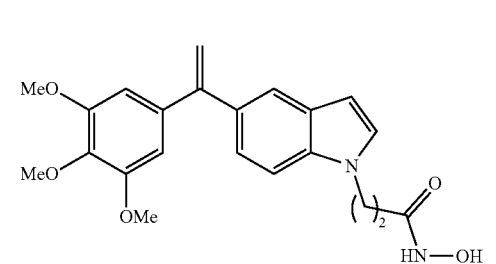
Advantageously, the compounds of the invention are selected from the following group:
1
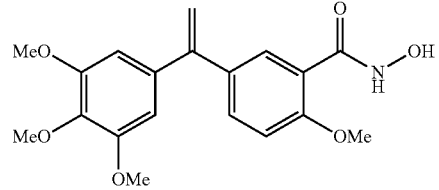
2
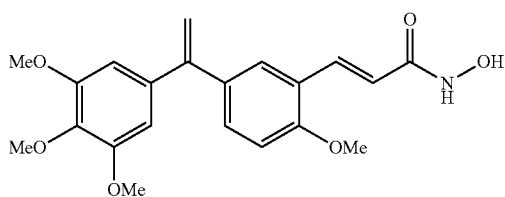
3
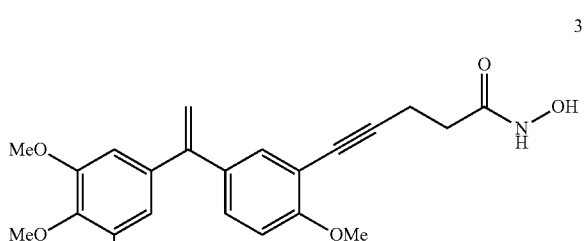
4
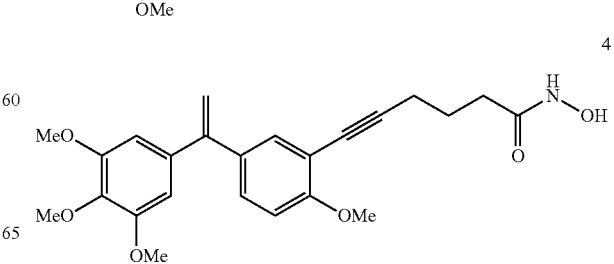

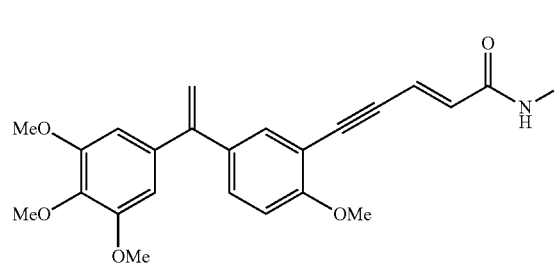

5

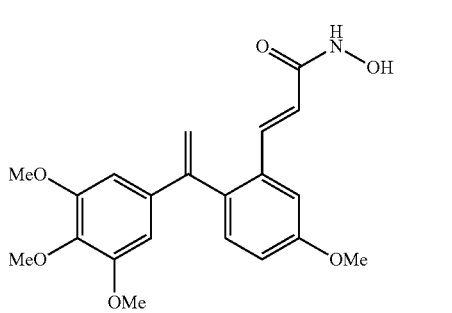

8

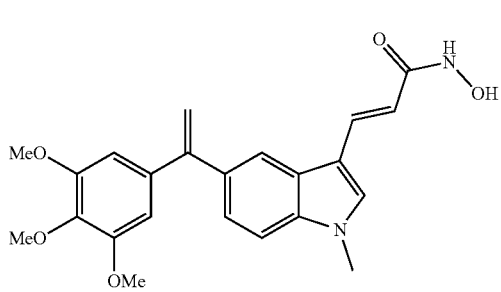

11

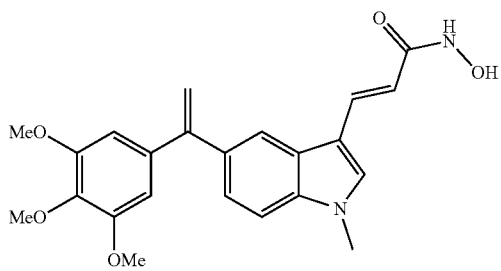

12

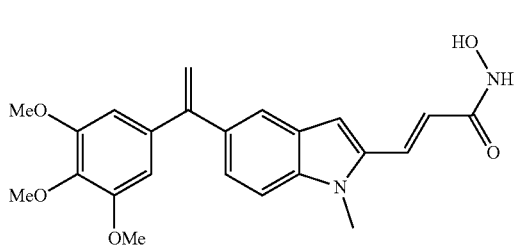

17

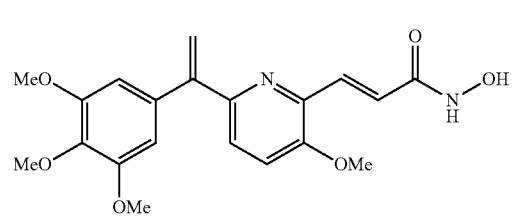

25

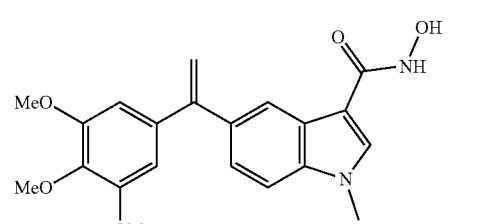

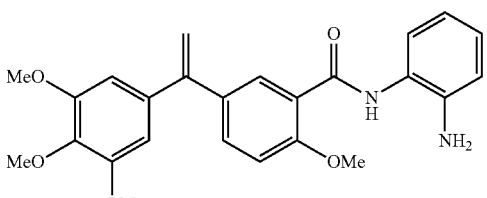

32

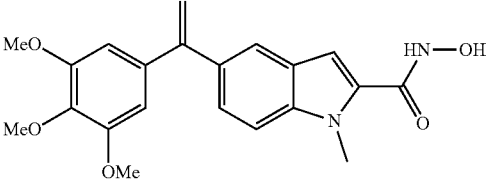

43

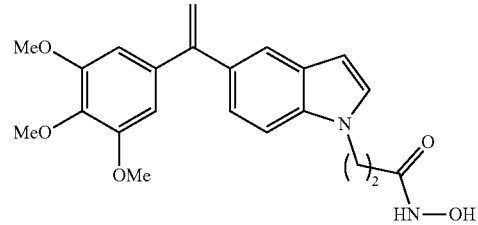

44

Process for Synthesising the Compounds of the Present Invention

The invention also relates to the processes for synthesising the compounds of the present invention. The synthesis processes are short, comprising advantageously 4 steps. These processes are compatible with industrial requirements.

The coupling of an easily accessible tosylhydrazone with a halogenated derivative leads to compounds of the invention with excellent yields, advantageously without having to resort to protection-deprotection steps.

The compounds of the invention can be prepared according to processes known to persons skilled in the art, from products which are available commercially or are prepared according to methods known to persons skilled in the art.

Compounds having formulas (II), (III-a) and (III-b1) can be prepared by a process comprising the following successive steps:

1 Reaction of the compound having the following general formula:

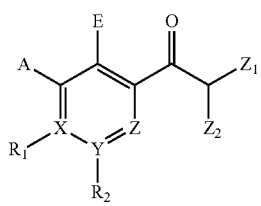

with tosylhydrazine to give the tosylhydrazone having the following general formula:

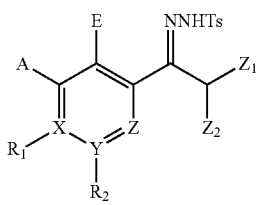

where $Z_1$, $Z_2$, X, Y, Z, A, E, $R_1$, $R_2$, are as defined above;

2 Metal-catalysed coupling of the tosylhydrazone obtained in the preceding step with a compound having the general formula I-G-Hal to obtain the compound having the following general formula:

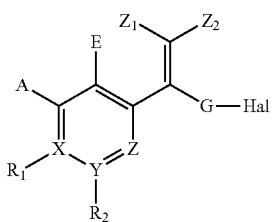

the metal-catalysed coupling being advantageously carried out with palladium, and Hal represents a halogen selected from a bromine atom or a chlorine atom, where G is as defined above;

3 Metal-catalysed coupling carried out on the compound obtained in the preceding step followed by a treatment allowing the introduction of group -(L)$_n$-B and obtaining the compound having the following general formula:

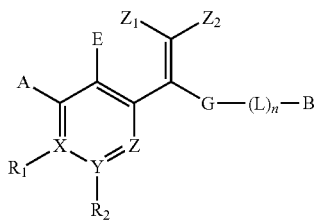

advantageously the metal-catalysed coupling is carried out with palladium or copper, and where L, n and B are as defined above.

Compounds of the present invention, for which $Z_2$=B, can be prepared by a process comprising the following successive steps:

a. Reaction of the compound having the following general formula:

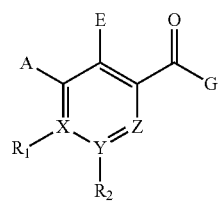

with a phosphonate having the following general formula:

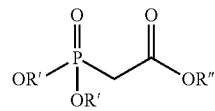

where R' and R" independently represent a ($C_1$ to $C_4$)alkyl, and making it possible to obtain the compound having the following general formula:

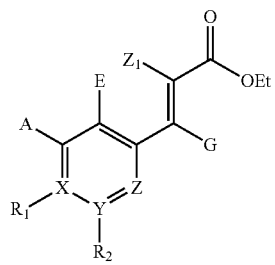

where $Z_1$, X, Y, Z, A, E, $R_1$, $R_2$ and G are as defined above;

b. Introduction of a group selected from a hydroxamic acid and an amide having the following general formula:

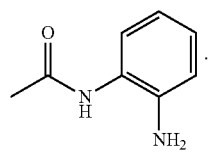

making it possible to obtain the compound having the following general formula:

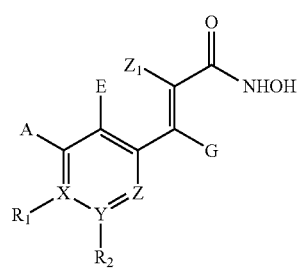

or

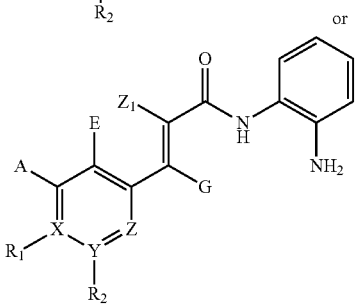

The compounds having formula (III-b2) are prepared preferentially by a process comprising the following successive steps:

1 Reaction of the compound having the following general formula:

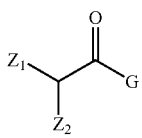

with tosylhydrazine to give the tosylhydrazone having the following general formula:

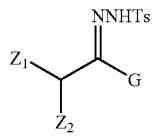

where $Z_1$, $Z_2$, and G are as defined above;

2 Metal-catalysed coupling of the tosylhydrazone obtained in the preceding step with a compound having the following general formula

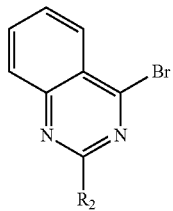

to obtain the compound having the following general formula:

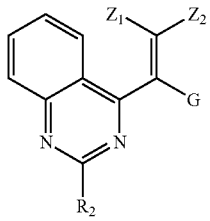

the metal-catalysed coupling being advantageously carried out with palladium, and where $R_2$ is as defined above;

3 Metal-catalysed coupling carried out on the compound obtained in the preceding step followed by a treatment allowing the introduction of group -(L)$_n$-B and obtaining the compound having the following general formula:

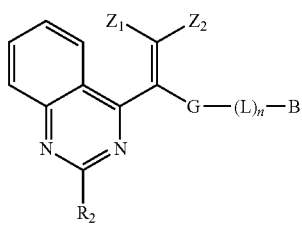

advantageously the metal-catalysed coupling is carried out with palladium or copper, and where L, n and B are as defined above.

Use of the Compounds of the Present Invention

In certain aspects, the invention relates to compounds of general formula (I) and to the pharmaceutically acceptable salts, stereoisomers and prodrugs thereof, for use as a drug. In particular, the compounds of the present invention can be used as drugs acting as inhibitors of both HDAC and tubulin polymerisation, advantageously as drugs for treating or preventing cancer.

The present invention preferentially relates to a pharmaceutical composition comprising at least one compound of formula (I), and to the pharmaceutically acceptable salts thereof, in combination with one or more pharmaceutically acceptable excipients.

In a preferred embodiment, the pharmaceutical composition comprises at least one other active principle, advantageously selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide, lanreotide, (Z)-3-[2,4-dimethyl-5-(2-oxo-1,2-dihydro-indol-3-ylidenemethyl)-1H-pyrrol-3-yl]propionic acid, 4-((9-chloro-7-(2,6-difluorophenyl)-5H-pyrimidol(5,4-d)(2)benzazepin-2-yl)amino) benzoic acid, 5,6-dimethylxanthenone-4-acetic acid and 3-(4-(1,2-diphenylbut-1-enyl)phenyl)acrylic acid. Advantageously, the compound having the general formula (I) or the pharmaceutical composition is used in the prevention or treatment of cancer, typically malignant lymphomas and human leukaemias.

The invention also relates to an "antibody-drug" conjugate, also called ADC, which is defined by the combination of:
- an antibody, an antibody fragment, or equivalent, preferably the antibody is a monoclonal antibody;
- a linker molecule, and;
- a compound of the present invention, covalently linked to each other.

The antibody is capable of recognising a tumour cell-specific antigen and of binding thereto. Once the "antigen-ADC" unit attaches to the wall of the cancer cell, it is internalised within the cell via an endosome. The ADC is then degraded under the conditions characteristic of the intracellular environment. The compound of the present invention is then released to act within the cancer cell. This mechanism of action makes it possible to target the delivery of the drug to the zones in need thereof and makes it possible to enhance the efficacy of the drug while decreasing its toxicity.

The invention also relates to a pharmaceutical composition comprising at least one conjugate as defined above. The composition may include one or more pharmaceutically acceptable excipients.

The compounds and compositions of the invention may be administered via the oral, sublingual, parenteral, subcutaneous, intramuscular, intravenous, transdermal, local or rectal route.

The compounds of the present invention may be used at doses between 0.01 mg and 1000 mg per day, given in a single dose once a day or preferably administered in several doses throughout the day, for example twice a day in equal doses. The dose administered per day is advantageously between 5 mg and 500 mg, more advantageously between 10 mg and 200 mg. It may be necessary to use doses outside these ranges, which persons skilled in the art can determine for themselves.

The compounds of the invention can be used both to decrease or inhibit tubulin polymerisation and to decrease or inhibit HDACs, notably in vitro and also in vivo.

The present invention also relates to a pharmaceutical composition comprising:
(i) at least one compound having the general formula (I), and;
(ii) at least one other active principle,
as a combination product for simultaneous, separate or sequential use, advantageously for the prevention or treatment of cancer, typically malignant lymphomas, human leukaemias, colorectal carcinoma, lung cancer, chronic myeloid leukaemias, imatinib-resistant chronic myeloid leukaemias, breast cancer, prostate cancer, glioblastomas, osteosarcomas, and pancreatic tumour cell lines.

Finally, the invention relates to a pharmaceutical composition comprising at least one compound of the present invention in combination with an antibody. The composition may comprise one or more pharmaceutically acceptable excipients. The antibody is used to target the tumour. In particular, the pharmaceutical composition may comprise at least one compound of the present invention in combination with a monoclonal antibody. The combination of the compound of the present invention with the antibody may be prepared in the form of "antibody-compound of the present invention" conjugates. The antibody and the compound of the present invention are typically covalently linked via a linker. In particular, this linker will be advantageously grafted onto group G of the compounds of the present invention. Persons skilled in the art will know how to determine the nature of the linker suited to the linking of the compound of the invention with an antibody. Therefore, in an embodiment, the invention relates to a conjugate comprising a compound of the present invention, covalently linked to an antibody.

The invention will now be illustrated, in a non-limiting manner, by the following examples.

EXAMPLES

Abbreviations

NMR: nuclear magnetic resonance
HRMS: high-resolution mass spectrometry
MS: mass spectrometry
ESI+: positive-mode electrospray ionisation
ES: electrospray
TLC: thin-layer chromatography
Rf: retention factor
mp: melting point
$CDCl_3$: deuterated chloroform
$CD_3COCD_3$: deuterated acetone
$CHCl_3$: chloroform
MeOH: methanol
$CH_2Cl_2$: dichloromethane
$Et_2O$: diethyl ether
EtOAc: ethyl acetate
DMF: dimethylformamide
THF: tetrahydrofuran
LTB: lithium tert-butoxide
$Pd_2dba_3$: tris(dibenzylideneacetone)dipalladium
X-Phos: 2-dicyclohexylphosphino-2',4',6'-triisopropylbiphenyl
$K_2CO_3$ potassium carbonate
$MgSO_4$: magnesium sulphate
$Na_2SO_4$: sodium sulphate
$Et_3N$: triethylamine
$PdCl_2(PPh_3)_2$: bis(triphenylphosphine)palladium dichloride
CuI: copper iodide
ACN: acetonitrile
General Procedure:
Solvent peaks are used as reference values in $^1H$ and $^{13}C$ NMR:
$CDCl_3$ at 7.26 ppm in $^1H$ NMR, and at 77.16 ppm in $^{13}C$ NMR;
$CD_3COCD_3$ at 2.05 ppm in $^1H$ NMR, and at 29.84 ppm in $^{13}C$ NMR.

The chemical shifts δ are given in ppm, and the following abbreviations are given: singulet (s), doublet (d), doublet of doublets (dd), triplet (t), multiplet (m) and broad singulet (bs).

The reaction monitoring and product mixtures are performed by TLC, and the products are revealed with phosphomolybdic acid, or with para-anisaldehyde, or with vanillin.

Purifications are carried out on silica gel 60 (40-63 mm, type 230-400) at medium pressure (200 mbar). Dioxane, dichloromethane, cyclohexane and tetrahydrofuran are dried according to the procedures described in "D. Perrin Purification of Laboratory Chemicals". Organic extracts are generally dried over $MgSO_4$ or $Na_2SO_4$. High-resolution mass spectra are recorded with MicrOTOF-Q II. All products presented below are consistent with the $^1H$ and $^{13}C$ NMR data.

Procedure for Synthesising isoCA-4.

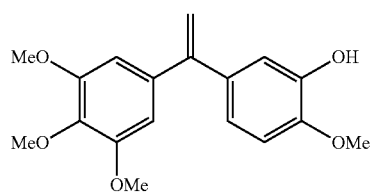

isoCA4

To a solution of N-tosylhydrazone (0.42 mmol), LTB (84 mg, 1.05 mmol), $Pd_2dba_3.CHCl_3$ (44 mg, 0.042 mmol) and X-Phos (40 mg, 0.084 mmol) in dioxane (6 mL) is added tert-butyl(5-iodo-2-methoxyphenoxy)dimethylsilane (0.42 mmol) in dioxane (1 mL). The mixture is stirred at 90° C. for 5 h. CH$_2$Cl$_2$ (10 mL) is added to the cooled mixture and then filtered through Celite. After concentration, the residue is dissolved in MeOH (3 mL), K$_2$CO$_3$ (116.0 mg, 0.84 mmol) is added, and stirring is continued for 2 h. Water (10 mL) is added and the aqueous phase is extracted with Et$_2$O (3×10 mL). The organic phase is washed with brine (15 mL), dried over MgSO$_4$, and concentrated under vacuum to give the crude product which is then purified on silica gel. isoCA-4 molar yield: 69% in the form of a white powder.

mp: 109-110° C. TLC: Rf 0.21 (Cyclohexane/EtOAc: 80/20). $^1$H NMR (300 MHz, CDCl$_3$): 6.97 (d, 1H, J=2.1 Hz), 6.82 (m, 2H), 6.55 (s, 2H), 5.61 (bs, 1H), 5.37 (d, 1H, J=1.5 Hz), 5.30 (d, 1H, J=1.5 Hz), 3.91 (s, 3H), 3.87 (s, 3H), 3.81 (s, 6H). $^{13}$C NMR (75 MHz, CDCl3): 152.8, 149.5, 148.4 (20), 145.2, 137.8, 137.4, 134.7, 120.2, 114.4, 112.8, 110.1, 105.8 (20), 60.9, 56.1 (20), 55.9. m/z MS (ESI+) 317.24 (M+H)+.

Ethyl 5-(2-methoxy-5-(1-(3,4,5-trimethoxyphenyl) vinyl)phenyl)pent-4-ynoate (45)

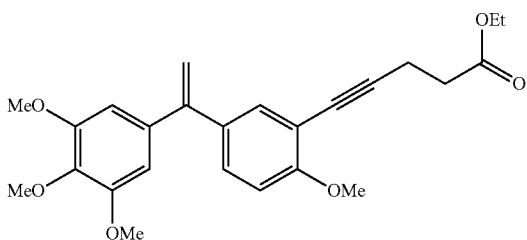 [SMILES: C=C(c1ccc(OC)c(C#CCCC(=O)OCC)c1)c1cc(OC)c(OC)c(OC)c1]

Et$_3$N (0.7 mL), PdCl$_2$(PPh$_3$)$_2$ (35 mg, 0.05 mmol), and CuI (15 mg, 0.08 mmol) are added to a solution of 5-(1-(3-iodo-4-methoxyphenyl)vinyl)-1,2,3-trimethoxybenzene (190 mg, 0.446 mmol) in THF (3.0 mL). Ethyl 4-pentynoate (122 mg, 0.98 mmol) in THF (3.0 mL) is then added to the mixture, then stirred at 60° C. for 16 h. After cooling, EtOAc (25 mL) is added to the crude mixture, which is washed with NH$_4$Cl solution. After extraction with EtOAc, the organic phase is dried over MgSO$_4$ and concentrated under vacuum. Purification on silica gel yields 180 mg of 45 (molar yield: 95%) in the form of a brown oil. TLC: Rf=0.4 (EtOAc/Cyclohexane 3/7, SiO$_2$). $^1$H NMR (300 MHz, CDCl$_3$) δ 7.32 (d, J=2.3 Hz, 1H), 7.15 (dd, J=8.6, 2.3 Hz, 1H), 6.74 (d, J=8.7 Hz, 1H), 6.45 (s, 2H), 5.28 (d, J=1.2 Hz, 1H), 5.26 (d, J=1.2 Hz, 1H), 4.09 (q, J=7.1 Hz, 2H), 3.82 (s, 3H), 3.81 (s, 3H), 3.74 (s, 6H), 2.76-2.68 (m, 2H), 2.62-2.52 (m, 2H), 1.19 (t, J=7.1 Hz, 3H). $^{13}$C NMR (75 MHz, CDCl$_3$) δ 153.1 (C), 149.1 (C), 137.3 (C), 133.8 (C), 133.7 (CH), 129.3 (CH), 113.1 (C), 110.4 (CH), 105.8 (2CH), 92.5 (C), 61.1 (CH$_3$), 60.8 (CH$_2$), 56.3 (CH$_3$), 56.1 (CH$_3$), 33.9 (CH$_2$), 15.9 (CH$_2$), 14.4 (CH$_3$). HRMS (ES) (M+H)$^+$: m/z calc. for C$_{25}$H$_{29}$O$_6$ 425.1964, found 425.1960.

Methyl (E)-3-(2-methoxy-5-(1-(3,4,5-trimethoxyphenyl)vinyl)phenyl)acrylate (46)

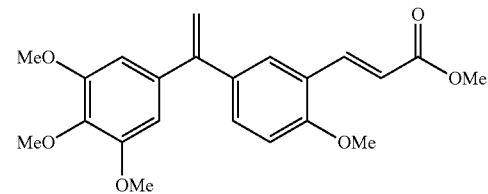 [SMILES: C=C(c1ccc(OC)c(/C=C/C(=O)OC)c1)c1cc(OC)c(OC)c(OC)c1]

A mixture of 250 mg (0.587 mmol) of 5-(1-(3-iodo-4-methoxyphenyl)vinyl)-1,2,3-trimethoxybenzene, 303 mg (3.52 mmol) of methyl acrylate, 7 mg (0.03 mmol) of palladium diacetate, 18 mg (0.06 mmol) of tri-o-tolylphosphine, and 3 mL of distilled triethylamine are heated to 110° C. for 24 h under argon in a sealed Pyrex tube. To the cooled mixture is added water then EtOAc. After extraction, the organic phases are combined then washed with water, dried over MgSO$_4$, and concentrated under vacuum. Purification on silica gel yields 185 mg of 46 (molar yield: 85%), in the form a colourless oil. TLC: Rf=0.3 (EtOAc/Cyclohexane 3/7, SiO$_2$). $^1$H NMR (300 MHz, CDCl$_3$) δ 7.99 (d, J=16.2 Hz, 1H), 7.53 (d, J=2.3 Hz, 1H), 7.36 (dd, J=8.6, 2.3 Hz, 1H), 6.91 (d, J=8.6 Hz, 1H), 6.56 (s, 2H), 6.54 (d, J=16.2 Hz, 1H), 5.40 (d, J=1.2 Hz, 1H), 5.39 (d, J=1.2 Hz, 1H), 3.94 (s, 3H), 3.91 (s, 3H), 3.84 (s, 6H), 3.82 (s, 3H). $^{13}$C NMR (75 MHz, CDCl$_3$) δ 140.3 (CH), 134.0 (C), 131.5 (CH), 129.0 (CH), 118.9 (CH), 113.3 (CH$_2$), 111.0 (CH), 105.8 (2CH), 61.1 (CH$_3$), 56.3 (2 CH$_3$), 55.8 (CH$_3$), 51.7 (CH$_3$). HRMS (ES) (M+H)$^+$: m/z calc. for C$_{22}$H$_{25}$O$_6$ 385.1651, found 385.1648.

Preparation of Fresh Hydroxylamine Solution.

A solution of potassium hydroxide (11.2 g, 199.6 mmol) in methanol (28 mL) is added to a solution of hydroxylamine hydrochloride (9.34 g, 134.4 mmol) in methanol (48 mL) with stirring at 0° C. The reaction mixture is stirred at 0° C. for 30 min. The precipitate formed is then filtered. The filtrate is collected to give the hydroxylamine solution which is stored in the refrigerator before use.

N-Hydroxy-5-(2-methoxy-5-(1-(3,4,5-trimethoxyphenyl)vinyl)phenyl)pent-4-ynamide (3)

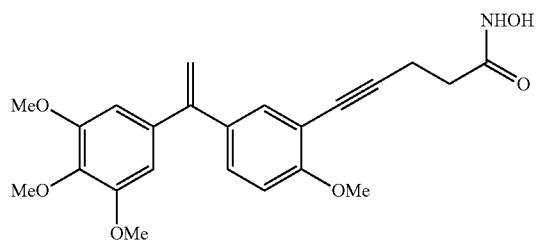

Ester 45 (170 mg, 0.425 mmol) is added to the freshly prepared hydroxylamine solution (3 mL) at 0° C. The reaction mixture is returned to room temperature and stirred at 25° C. for 5 h until this ester 45 is completely converted (the reaction is monitored by TLC). The solvent is evaporated under vacuum to give the crude reaction product. Purification on silica gel yields 150 mg of 3 (molar yield: 85%), in the form a white solid. mp=73-75° C. TLC:

Rf=0.15 (CH$_2$Cl$_2$/MeOH 95/5, SiO$_2$). $^1$H NMR (300 MHz, Acetone-d$_6$) δ 10.01 (s, 1H), 8.00 (s, 1H), 7.35-7.24 (m, 2H), 7.00 (d, J=8.5 Hz, 1H), 6.60 (s, 2H), 5.38 (d, J=0.6 Hz, 2H), 3.89 (s, 3H), 3.79 (s, 6H), 3.76 (s, 3H), 2.72 (t, J=7.2 Hz, 2H), 2.39 (t, J=7.3 Hz, 2H). $^{13}$C NMR (75 MHz, Acetone) δ 150.0 (C), 145.6 (C), 134.4 (C), 133.7 (C), 130.3 (CH), 129.9 (CH), 113.3 (CH$_2$), 111.5 (CH), 106.7 (2CH), 103.9 (C), 60.6 (CH$_3$), 56.5 (2CH$_3$), 56.1 (CH$_3$), 32.8 (CH$_2$), 16.4 (CH$_2$). HRMS (ES) (M+H)$^+$: m/z calc for C$_{23}$H$_{26}$NO$_6$ 412.1760, found 412.1758.

(E)-N-Hydroxy-3-(2-methoxy-5-(1-(3,4,5-trimethoxyphenyl)vinyl)phenyl)acrylamide (2)

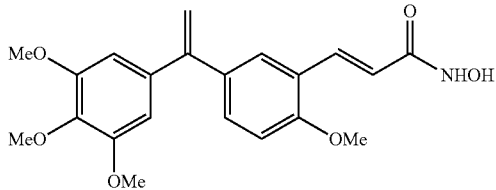

Ester 46 (348 mg, 0.906 mmol) is added to the freshly prepared hydroxylamine solution (3 mL) at 0° C. The reaction mixture is returned to room temperature and stirred at 25° C. for 5 h until this ester 46 is completely converted (the reaction is monitored by TLC). The solvent is evaporated under vacuum to give the crude reaction product. Purification on silica gel yields 210 mg of 2 (molar yield: 60%), in the form a white solid. mp=93-95° C. TLC: Rf=0.30 (CH$_2$Cl$_2$/MeOH 95/5, SiO$_2$). $^1$H NMR (300 MHz, Acetone-d6) δ 10.26 (s, 1H), 7.90 (d, J=15.4 Hz, 1H), 7.57 (s, 1H), 7.36 (dd, J=8.6, 1.9 Hz, 1H), 7.08 (d, J=8.6 Hz, 1H), 6.71-6.54 (m, 3H), 5.42 (s, 2H), 3.95 (s, 3H), 3.79 (s, 6H), 3.77 (s, 3H). $^{13}$C NMR (75 MHz, Acetone) δ 158.8 (C), 154.2 (2C), 150.2 (C), 139.3 (C), 137.8 (C), 134.7 (C), 131.6 (C), 128.6 (CH), 124.3 (CH), 119.3 (C), 113.4 (CH$_2$), 112.1 (CH), 106.7 (2CH), 60.6 (CH$_3$), 56.5 (2CH$_3$), 56.1 (CH$_3$). HRMS (ES) (M+H)$^+$: m/z calc. for C$_{21}$H$_{24}$NO$_6$ 386.1604, found 386.1599.

General Procedure for Coupling N-tosylhydrazones and Aryl Bromide (Method A)

SPhos (10 mol %), Pd(OAc)$_2$ (35 mg, 5 mol %) and LTB (2.4 equiv.) were added to a solution of halogenated aryl (951 mg, 1 equiv.) in 1,4-dioxane (12 mL), the mixture was stirred at 110° C. A solution of N-tosylhydrazone (1.5 equiv.) in 1,4-dioxane (12 mL) was added to the mixture dropwise over 1 hour at 110° C. The mixture was stirred at 110° C. for an additional 1 h. After cooling, EtOAc was added and the mixture was filtered through a layer of Celite. The solvent was evaporated under reduced pressure and the crude product was purified by chromatography on silica gel.

General Procedure for Sonogashira Coupling (Method B).

Et$_3$N (6 mL/mmol aryl bromide), PdCl$_2$(PPh$_3$)$_2$ (5 mole %) and CuI (10 mole %) are added to aryl bromide (1 equiv.). The alkyne (2 equivalents) was added to the mixture and stirred at 50° C. for 16 h. After cooling, cyclohexane was added to the crude mixture and filtered through Celite. The solvent was evaporated under reduced pressure and the crude product was purified by flash chromatography on silica gel.

General Procedure for Heck Coupling (Method C).

A mixture of aryl halide (1 equivalent), methyl acrylate (6 equivalents), Pd(OAc)$_2$ (3 mol %), P(o-Tol)$_3$ (6 mol %) and 5 mL of anhydrous triethylamine was heated to 110° C. for 24 hours in a capped, thick-walled Pyrex tube and swept with dry argon. After cooling, water and EtOAc are added. After extraction, the combined organic solutions were washed with water and dried over MgSO$_4$. The solvent was evaporated under reduced pressure and the crude product was purified by chromatography on silica gel.

General Procedure for the Formation of Hydroxamic Acid Derivatives by Coupling with EDCI (Method D).

Saponification. A sodium hydroxide solution (1N, 2 equivalents) is added to a solution of indole ester (1 equivalent) in ethanol, and the mixture was heated at reflux for 1 to 4 hours. At the end of the reaction (monitored by TLC), the ethanol is evaporated and the aqueous phase was acidified with 1N HCl, then extracted with ethyl acetate. The organic phase was dried over MgSO$_4$ and concentrated under reduced pressure.

Coupling. Indole carboxylic acid (1 mmol, 1 equiv.) is dissolved in 11 mL of DMF, then 1-hydroxybenzotriazole (HOBt) (1.5 mmol, 1.5 equiv.) is added all at once, followed by the addition of N-(3-dimethylaminopropyl)-N'-ethylcarbodiimide (EDC. HCl) (1.6 mmol, 1.6 equiv.) and the mixture was stirred at room temperature for 5 h. To this solution, hydroxylamine hydrochloride (5 mmol, 5 equiv.) and triethylamine (5 mmol, 5 equiv.) are added and stirring is continued for 15 h. The suspension was diluted with water (40 mL), extraction with ethyl acetate is performed and the organic layer is dried over MgSO$_4$ and concentrated under reduced pressure. The crude reaction product was purified by preparative HPLC.

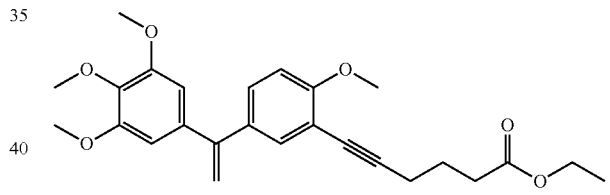

Ethyl 6-(2-methoxy-5-(1-(3,4,5-trimethoxyphenyl)vinyl)phenyl)hex-5-ynoate (47)

Compound 47 was prepared according to general procedure B from 5-(1-(3-iodo-4-methoxyphenyl)vinyl)-1,2,3-trimethoxybenzene (0.69 mmol) and ethyl hexyl-5-ynoate (1.04 mmol). Purification by column chromatography on silica gel gave 220 mg of 47 (yield 73%). Brown oil; Rf=0.3 (EtOAc/cyclohexane 25/75, SiO$_2$); $^1$H NMR (300 MHz, CDCl$_3$) δ 7.40 (d, J=2.2 Hz, 1H), 7.22 (d, J=8.6 Hz, 1H), 6.81 (d, J=8.7 Hz, 1H), 6.53 (s, 2H), 5.34 (d, J=7.4 Hz, 2H), 4.13 (q, J=7.1 Hz, 2H), 3.92-3.78 (m, 12H), 2.53 (dd, J=13.8, 7.0 Hz, 4H), 2.00-1.89 (m, 2H), 1.25 (t, J=7.1 Hz, 4H); $^{13}$C NMR (75 MHz, CDCl$_3$) δ 159.8 (C), 153.0 (2C), 149.1 (C), 137.4 (C), 133.8 (C), 133.5 (CH), 129.2 (2CH), 113.1 (CH$_2$), 112.8 (C), 110.3 (CH), 105.8 (2CH), 93.5 (20), 61.1 (CH$_3$), 60.5 (CH$_2$), 56.3 (2CH$_3$), 56.1 (CH$_3$), 33.3 (CH$_2$), 29.8 (C), 24.2 (CH$_2$), 19.4 (CH$_2$), 14.2 (CH$_3$); IR (film, cm$^{-1}$): 2938, 2837, 1731, 1651, 1581, 1502, 1465, 1414, 1375, 1333, 1271, 1237, 1180, 1127, 1026, 1004, 765; HRMS (ESI) (M+H)$^+$, calcd for C$_{26}$H$_{31}$O$_6$: 439.2121, found: 439.2112.

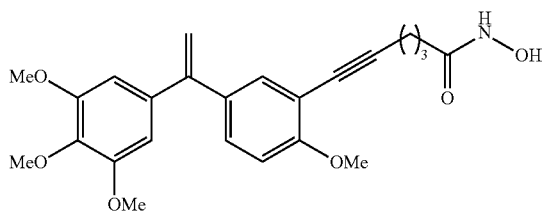

N-Hydroxy-6-(2-methoxy-5-(1-(3,4,5-trimethoxyphenyl)vinyl)phenyl)hex-5-ynamide (4)

Ester 47 (0.34 mmol) is added to the freshly prepared hydroxylamine solution (2 mL) at 0° C. The reaction mixture is returned to room temperature and stirred at 25° C. for 5 hours until this ester 47 is completely converted (the reaction is monitored by TLC). The solvent is evaporated under vacuum to give the crude reaction product. Purification on silica gel yields 118 mg of 4 (yield 82%). Brown oil; $R_f$=0.4 (DCM/MeOH 95/5, $SiO_2$); $^1$H NMR (300 MHz, $CDCl_3$) δ 7.38 (d, J=2.2 Hz, 1H), 7.28 (d, J=2.3 Hz, 1H), 6.87 (d, J=8.6 Hz, 1H), 6.52 (s, 2H), 5.36 (d, J=5.3 Hz, 2H), 4.01-3.81 (m, 12H), 2.51 (dd, J=12.1, 5.8 Hz, 4H), 2.17 (d, J=1.9 Hz, 1H), 1.95 (dd, J=13.4, 6.5 Hz, 2H); $^{13}$C NMR (75 MHz, $CDCl_3$) δ 170.5 (C), 159.8 (C), 153.1 (2C), 149.0 (C), 137.2 (C), 134.2 (C), 133.0 (CH), 129.4 (CH), 113.4 ($CH_2$), 112.4 (C), 110.4 (CH), 105.8 (2CH), 92.9 (2C), 61.1 ($CH_3$), 56.3 (20$H_3$), 56.1 ($CH_3$), 46.0 (C), 31.2 ($CH_2$), 23.4 ($CH_2$), 18.3 ($CH_2$); IR (film, $cm^{-1}$): 2925, 2360, 1666, 1580, 1501, 1464, 1412, 1343, 1294, 1272, 1254, 1236, 1180, 1126, 1082, 1026, 1004, 896, 846, 820, 780, 631; HRMS (ESI) $(M+H)^+$, calcd for $C_{24}H_{28}NO_6$: 426.1917, found: 426.1926.

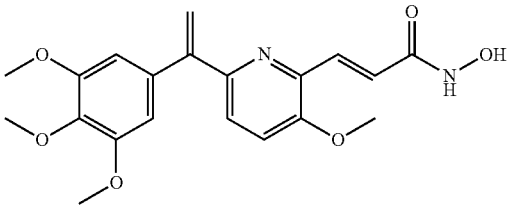 [SMILES: C=C(c1cc(OC)c(OC)c(OC)c1)c1ccc(OC)c(/C=C/C(=O)NO)n1]

(E)-N-Hydroxy-3-(3-methoxy-6-(1-(3,4,5-trimethoxyphenyl)vinyl)pyridin-2-yl)acrylamide (17)

Ester 48 (0.90 mmol) is added to the freshly prepared hydroxylamine solution (3 mL) at 0° C. The reaction mixture is returned to room temperature and stirred at 25° C. for 5 hours until this ester 48 is completely converted (the reaction is monitored by TLC). The solvent is evaporated under vacuum to give the crude reaction product. Purification on silica gel yields 201 mg of 17 (yield 58%). Yellow oil; TLC: $R_f$=0.17 (MeOH: dichloromethane, 5:95); $^1$H NMR (300 MHz, DMSO-$d_6$) (δ ppm): 10.91 (s, 1H), 9.06 (s, 1H), 7.81 (d, J=15.4 Hz, 1H), 7.49 (d, J=8.7 Hz, 1H), 7.27 (d, J=8.7 Hz, 1H), 6.97 (d, J=15.4 Hz, 1H), 6.64 (s, 2H), 5.90 (s, 1H), 5.56 (s, 1H), 3.91 (s, 3H), 3.74 (s, 5H), 3.70 (s, 2H). $^{13}$C NMR (75 MHz, DMSO) (δ ppm): 153.1 (C=O), 152.6 (2C), 148.8 (C), 147.5 (C), 137.2 (C), 135.4 (2C), 133.3 (CH), 124.3 (CH), 122.7 (CH), 119.6 (CH), 116.2 ($CH_2$), 105.5 (2 CH), 60.0 ($OCH_3$), 55.8 (3 $OCH_3$). HRMS (ESI) for $C_{20}H_{23}N_2O_6$ $[M+H]^+$: calcd 387.1529, found 387.1475.

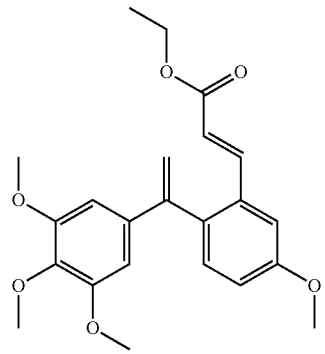 [SMILES: C=C(c1cc(OC)c(OC)c(OC)c1)c1ccc(OC)cc1/C=C/C(=O)OCC]

Methyl (E)-3-(3-methoxy-6-(1-(3,4,5-trimethoxyphenyl)vinyl)pyridin-2-yl)acrylate (48)

Compound 48 was prepared according to method C from 2-bromo-3-methoxy-6-(1-(3,4,5-trimethoxyphenyl)vinyl) pyridine (0.26 mmol) and methyl acrylate (1.56 mmol). Purification by flash chromatography on silica gel gave 78 mg of 48 (yield 77%). Yellow oil. TLC: $R_f$=0.23 (EtOAc: cyclohexane, 3:7); $^1$H NMR (300 MHz, $CDCl_3$) (δ ppm): 8.12 (d, J=15.7 Hz, 1H), 7.22 (d, J=8.6 Hz, 1H), 7.15 (d, J=8.6 Hz, 1H), 7.13 (d, J=15.7 Hz, 1H), 6.60 (s, 2H), 6.07 (d, J=1.5 Hz, 1H), 5.48 (d, J=1.5 Hz, 1H), 3.90 (s, 3H), 3.89 (s, 3H), 3.83 (s, 6H), 3.82 (s, 3H). $^{13}$C NMR (75 MHz, $CDCl_3$) (δ ppm): 153.0 (C=O), 152.8 (C), 148.3 (2C), 145.1 (CH), 138.1 (CH), 136.5 (2C), 137.8 (C), 132.4 (C), 131.5 (C), 131.0 (CH), 123.6 (CH), 117.8 (CH), 116.7 ($CH_2$), 105.9 (2 CH), 61.0 ($OCH_3$), 56.2 (2 $OCH_3$), 55.7 ($OCH_3$), 51.9 ($OCH_3$). HRMS (ESI) for $C_{21}H_{24}NO_6$ $[M+H]^+$: calcd 386.1604, found 386.1594.

(E)-Ethyl 3-(5-methoxy-2-(1-(3,4,5-trimethoxyphenyl)vinyl)phenyl)acrylate (49)

Compound 49 was prepared according to method C from 5-(1-(2-bromo-3-methoxyphenyl)vinyl)-1,2,3-trimethoxybenzene (0.92 mmol) and ethyl acrylate (5.5 mmol). Purification by column chromatography on silica gel gave 258 mg of 49 (yield 70%). Yellow oil; $R_f$=0.4 (EtOAc/Cyclohexane 20/80, $SiO_2$); $^1$H NMR (300 MHz, $CDCl_3$) δ 7.74 (d, J=15.9 Hz, 1H), 7.20-7.13 (m, J=9.2, 5.5 Hz, 2H), 6.93 (dd, J=8.5, 2.5 Hz, 1H), 6.46 (s, 2H), 6.31 (d, J=15.9 Hz, 1H), 5.77 (s, 1H), 5.11 (s, 1H), 4.17 (q, J=14.3, 7.1 Hz, 2H), 3.87-3.76 (m, 12H), 1.27 (t, J=6.9 Hz, 3H); $^{13}$C NMR (75 MHz, $CDCl_3$) δ 166.8 (C), 159.2 (C), 153.1 (2C), 153.0 (C), 147.1 (C), 143.5 (CH), 137.2 (C), 135.4 (C), 134.6 (C), 131.9 (CH), 119.2 (CH), 116.9 ($CH_2$), 116.0 (CH), 111.0 (CH), 104.7 (2CH), 61.0 ($CH_3$), 60.5 ($CH_2$), 56.2 (2$CH_3$), 55.5 (CH₃), 14.4 (CH₃); IR (film, cm⁻¹): 2938, 2838, 1711, 1634, 1601, 1581, 1504, 1466, 1413, 1368, 1332, 1233, 1179, 1127, 1032, 1006, 843, 765; HRMS (ESI) (M+H)⁺, calcd for C$_{23}$H$_{26}$O$_6$Na: 421.1627, found: 421.1638.

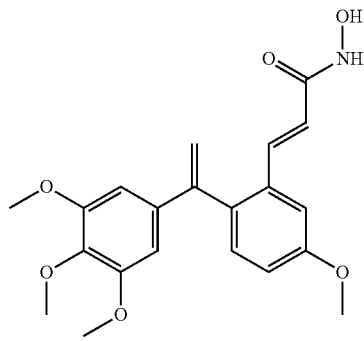 [SMILES: C=C(c1cc(OC)c(OC)c(OC)c1)c1ccc(OC)cc1/C=C/C(=O)NO]

(E)-N-Hydroxy-3-(5-methoxy-2-(1-(3,4,5-trimethoxyphenyl)vinyl)phenyl)acrylamide (8)

Ester 49 (0.42 mmol) is added to the freshly prepared hydroxylamine solution (2.2 mL) at 0° C. The reaction mixture is returned to room temperature and stirred at 25° C. for 5 hours until this ester 49 is completely converted (the reaction is monitored by TLC). The solvent is evaporated under vacuum to give the crude reaction product. Purification on silica gel yields 111 mg of 8 (yield 69%). Brown oil; R$_f$=0.3 (DCM/MeOH 95/5, SiO$_2$); ¹H NMR (300 MHz, CDCl$_3$) δ 7.54 (d, J=15.4 Hz, 1H), 7.24-7.17 (m, 2H), 6.92 (d, J=8.4 Hz, 1H), 6.41 (s, 2H), 6.23 (d, J=16.7 Hz, 1H), 5.67 (s, 1H), 5.17 (s, 1H), 3.89-3.65 (m, 12H); ¹³C NMR (75 MHz, CDCl$_3$) δ 159.4 (C), 153.2 (2C), 148.3 (C), 148.1 (C), 140.4 (CH), 138.5 (C), 137.3 (C), 135.4 (C), 134.6 (C), 131.8 (CH), 116.7 (CH$_2$), 116.6 (CH), 115.8 (CH), 111.0 (CH), 104.9 (2CH), 61.1 (CH$_3$), 56.2 (2CH$_3$), 55.5 (CH$_3$); IR (film, cm⁻¹): 2998, 2938, 2835, 2364, 1623, 1603, 1581, 1505, 1465, 1412, 1343, 1291, 1237, 1168, 1127, 1058, 1033, 1005, 902, 845; HRMS (ESI) [M+H]⁺, calcd for C$_{21}$H$_{24}$NO$_6$: 386.1604, found: 386.1608.

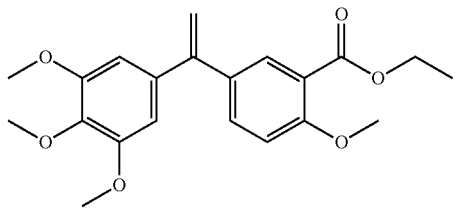 [SMILES: C=C(c1cc(OC)c(OC)c(OC)c1)c1ccc(OC)c(C(=O)OCC)c1]

Ethyl 2-methoxy-5-(1-(3,4,5-trimethoxyphenyl)vinyl)benzoate (50)

t-BuLi (2.33 mL, 1.7 M in pentane) is added to a solution of 637 mg (1.68 mmol) of 5-(1-(3-bromo-4-methoxyphenyl)vinyl)-1,2,3-trimethoxybenzene in THF (10 mL), the mixture is cooled to −78° C. for 30 minutes. Ethyl chloroformiate (392 mg, 3.62 mmol) was added and the mixture is stirred at room temperature for 1 h. EtOAc (25 mL) was added to the crude mixture, which was washed with a saturated NH$_4$Cl solution. After extraction with EtOAc, the combined extracts were dried over MgSO$_4$ and concentrated. Purification by column chromatography on silica gel gave 228 mg of 50 (yield 36%). Brown oil; R$_f$=0.25 (EtOAc/Cyclohexane 25/75, SiO$_2$); ¹H NMR (300 MHz, CDCl$_3$) δ 7.79 (d, J=2.3 Hz, 1H), 7.40 (dd, J=8.7, 2.3 Hz, 1H), 6.93 (d, J=8.7 Hz, 1H), 6.53 (s, 2H), 5.38 (d, J=4.3 Hz, 2H), 4.35 (q, J=7.1 Hz, 2H), 3.92-3.80 (m, 12H), 1.36 (t, J=7.1 Hz, 3H); ¹³C NMR (75 MHz, CDCl$_3$) δ 166.4 (C), 158.8 (C), 153.1 (2C), 148.8 (C), 137.0 (C), 133.5 (C), 133.2 (CH), 131.2 (CH), 120.6 (C), 113.5 (CH$_2$), 113.0 (C), 111.9 (CH), 105.7 (2CH), 61.1 (CH$_2$), 61.0 (CH$_3$), 56.3 (3CH$_3$), 14.4 (CH$_3$); IR (film, cm⁻¹): 2838, 1728, 1606, 1579, 1502, 1464, 1451, 1411, 1348, 1305, 1270, 1233, 1180, 1124, 1076, 1024, 1003, 950, 895, 845, 823, 788, 763, 734, 660; HRMS (ESI) (M+H)⁺, calcd for C$_{21}$H$_{25}$O$_6$: 373.1651, found: 373.1645.

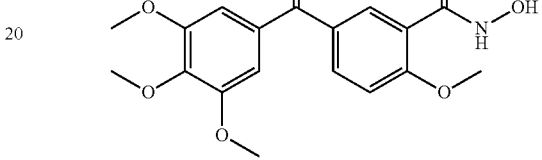

N-Hydroxy-2-methoxy-5-(1-(3,4,5-trimethoxyphenyl)vinyl)benzamide (1)

Ester 50 (0.42 mmol) is added to the freshly prepared hydroxylamine solution (1.5 mL) at 0° C. The reaction mixture is returned to room temperature and stirred at 25° C. for 5 hours until this ester 50 is completely converted (the reaction is monitored by TLC). The solvent is evaporated under vacuum to give the crude reaction product. Purification on silica gel yields 75 mg of 1 (yield 77%). Brown oil; Rf=0.45 (DCM/MeOH 95/5, SiO$_2$); ¹H NMR (300 MHz, CDCl$_3$) δ 10.35 (s, 1H), 8.26 (d, J=1.9 Hz, 1H), 7.42 (dd, J=8.6, 1.7 Hz, 1H), 6.96 (d, J=8.6 Hz, 1H), 6.50 (s, 2H), 5.42 (d, J=9.7 Hz, 2H), 4.07-3.78 (m, 12H); ¹³C NMR (75 MHz, CDCl$_3$) δ 163.2 (C), 156.9 (C), 153.1 (2C), 148.7 (C), 137.0 (C), 135.1 (C), 133.3 (CH), 131.5 (CH), 117.9 (C), 114.2 (CH$_2$), 111.2 (CH), 105.8 (2CH), 61.1 (CH$_3$), 56.4 (CH$_3$), 56.3 (2CH$_3$), 29.8 (C); IR (film, cm⁻¹): 2924, 1648, 1580, 1504, 1464, 1412, 1345, 1238, 1183, 1127, 1062, 1007, 895, 846, 824; HRMS (ESI) (M+H)⁺, calcd for C$_{19}$H$_{22}$NO$_6$: 360.1447. found: 360.1446.

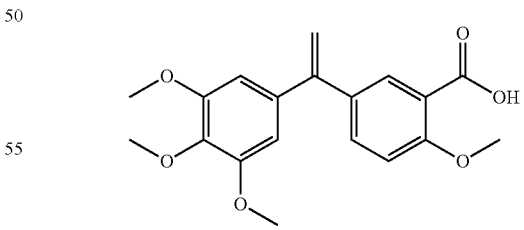

2-Methoxy-5-(1-(3,4,5-trimethoxyphenyl)vinyl)benzoic acid (51)

KOH (153 mg, 2.72 mmol) is added to a solution of ester 50 (125 mg, 0.34 mmol) in THF (3 mL), the mixture was stirred at 40° C. for 4 h. After cooling, water (3 mL) was added and the mixture is washed with diethyl ether (3 mL).

The aqueous solution was acidified to pH 1 and then an extraction with EtOAc was performed, the organic phase was dried over MgSO$_4$, the solvent was eliminated to give 73 mg of acid 51 (yield 62%). Brown oil; R$_f$=0.1 (EtOAc/Cyclohexane 3/7, SiO$_2$); $^1$H NMR (300 MHz, CDCl$_3$) δ 8.25 (d, J=2.4 Hz, 1H), 7.53 (dd, J=8.6, 2.4 Hz, 1H), 7.02 (s, 1H), 6.49 (s, 2H), 5.44 (d, J=4.3 Hz, 2H), 3.98-3.76 (m, 12H); $^{13}$C NMR (75 MHz, CDCl$_3$) δ 165.5 (C), 134.6 (CH), 114.5 (CH$_2$), 111.6 (CH), 107.7 (CH), 105.8 (2CH), 57.0 (CH$_3$), 56.5 (CH$_3$), 56.3 (20H$_3$); IR (film, cm$^{-1}$): 2941, 2838, 1731, 1650, 1603, 1581, 1503, 1466, 1413, 1333, 1267, 1234, 1182, 1126, 1004, 827, 765; HRMS (ESI) [M+H]$^+$, calcd for C$_{19}$H$_{20}$O$_6$: 367.1158, found: 367.1155.

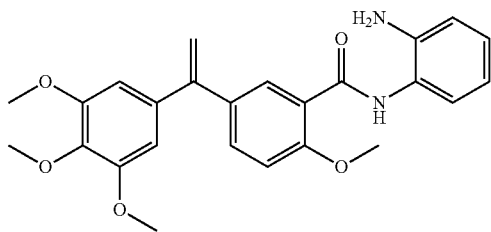 [SMILES: C=C(c1cc(OC)c(OC)c(OC)c1)c1ccc(OC)c(C(=O)Nc2ccccc2N)c1]

N-(2-Aminophenyl)-2-methoxy-5-(1-(3,4,5-trimethoxyphenyl)vinyl)benzamide (32)

EDCI.HCl (46 mg, 0.24 mmol), DIEA (65 mg, 0.50 mmol), o-phenylenediamine (22 mg, 0.20 mmol), HOBt (37 mg, 0.24 mmol) are added to a solution of 2-methoxy-5-(1-(3,4,5-trimethoxyphenyl)vinyl)benzoic acid (51) (70 mg, 0.20 mmol) in DMF (4 mL), the mixture is stirred at room temperature for 40 h. The solvent was removed and purified by chromatography on silica gel to give 52 mg of 32 (yield 60%). Yellow oil; R$_f$=0.55 (EtOAc 100%, SiO$_2$); $^1$H NMR (300 MHz, CDCl$_3$) δ 9.58 (s, 1H), 8.37 (d, J=2.4 Hz, 1H), 7.43 (t, J=8.3 Hz, 2H), 7.07 (d, J=8.1 Hz, 1H), 7.01 (d, J=8.6 Hz, 1H), 6.90-6.80 (m, 2H), 6.54 (s, 1H), 5.44 (d, J=17.8 Hz, 2H), 3.98-3.74 (m, 12H); $^{13}$C NMR (75 MHz, CDCl$_3$) δ 163.5 (O), 157.2 (O), 153.1 (20), 148.8 (O), 140.8 (O), 137.1 (C), 135.0 (O), 133.2 (CH), 132.4 (CH), 127.0 (CH), 125.4 (CH), 125.0 (C), 121.3 (O), 119.6 (CH), 118.0, (CH) 114.1 (CH$_2$), 111.4 (CH), 105.8 (2CH), 61.1 (CH$_3$), 56.5 (CH$_3$), 56.3 (20H$_3$), 29.8 (O); IR (film, cm$^{-1}$): 2837, 1661, 1600, 1580, 1534, 1503, 1461, 1449, 1412, 1346, 1238, 1180, 1127, 1005, 823, 752; HRMS (ESI) [M+H]$^+$, calcd for C$_{25}$H$_{27}$N$_2$O$_5$: 435.1920, found: 435.1909.

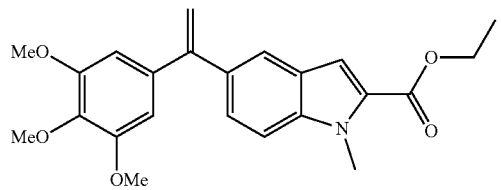 [SMILES: C=C(c1cc(OC)c(OC)c(OC)c1)c1ccc2c(c1)cc(C(=O)OCC)n2C]

Ethyl 1-methyl-5-(1-(3,4,5-trimethoxyphenyl)vinyl)-1H-indole-2-carboxylate (52)

Compound 52 was prepared according to method A from (Z)-4-methyl-N'-(1-(3,4,5-trimethoxyphenyl)ethylidene) benzenesulfonohydrazide (1 mmol) and ethyl 5-bromo-1-methyl-1H-indole-2-carboxylate (1.5 mmol). Purification by chromatography on silica gel gave 260 mg of 52 (yield 66%). Colourless oil; R$_f$=0.56 (EtOAc: cyclohexane, 2:8); $^1$H NMR (300 MHz, CDCl$_3$) (δ ppm): 7.66 (d, J=1.5 Hz, 1H), 7.38 (dd, J=8.8, 1.5 Hz, OH), 7.33 (d, J=8.8 Hz, 1H), 7.28 (s, 1H), 6.60 (s, 2H), 5.43 (d, J=1.3 Hz, 2H), 4.38 (q, J=7.1 Hz, 2H), 4.09 (s, 3H), 3.89 (s, 3H), 3.80 (s, 6H), 1.41 (t, J=7.1 Hz, 3H). $^{13}$C NMR (75 MHz, CDCl$_3$) (δ ppm): 162.1 (C=O), 152.9 (2C), 150.5 (C), 139.5 (C), 137.9 (2C), 134.0 (C), 128.6 (C), 125.8 (CH), 125.8 (C), 122.3 (CH), 113.0 (CH$_2$), 110.4 (CH), 109.9 (CH), 105.8 (2 CH), 60.9 (OCH$_3$), 60.6 (OCH$_2$), 56.2 (2 OCH$_3$), 31.8 (CH$_3$), 14.4 (CH$_3$). HRMS (ESI) for C$_{23}$H$_{26}$NO$_5$ [M+H]$^+$: calcd 396.1783, found 396.1802.

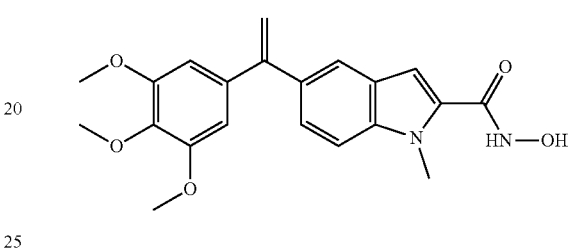

N-Hydroxy-1-methyl-5-(1-(3,4,5-trimethoxyphenyl)vinyl)-1H-indole-2-carboxamide (43)

This compound was prepared according to method D from ethyl 1-methyl-5-(1-(3,4,5-trimetoxyphenyl)vinyl)-1H-indole-2-carboxylate (52). Purification by HPLC gave 168 mg of 43 (yield 44%). White solid; mp: 179-181° C.; TLC: R$_f$=0.23 (MeOH: dichloromethane, 5:95); $^1$H NMR (300 MHz, DMSO-d$_6$) (δ ppm): 7.55 (s, 1H), 7.51 (d, J=8.8 Hz, 1H), 7.23 (d, J=8.8 Hz, 1H), 6.90 (s, 1H), 6.57 (s, 2H), 5.43 (d, J=3.6 Hz, 2H), 3.96 (s, 3H), 3.71 (s, 6H), 3.69 (s, 3H). $^{13}$C NMR (75 MHz, DMSO) (δ ppm): 169.7 (C), 152.6 (2C), 149.8 (C), 137.9 (C), 137.1 (C), 132.9 (C), 125.6 (C), 123.7 (CH), 122.8 (CH), 122.1 (C), 120.8 (CH), 113.1 (CH$_2$), 110.1 (CH), 106.4 (C), 105.5 (2 CH), 60.0 (OCH$_3$), 55.8 (2 OCH$_3$), 31.2 (CH$_3$). HRMS (ESI) for C$_{21}$H$_{23}$N$_2$O$_5$ [M+H]$^+$: calcd 383.1585, found 383.1590.

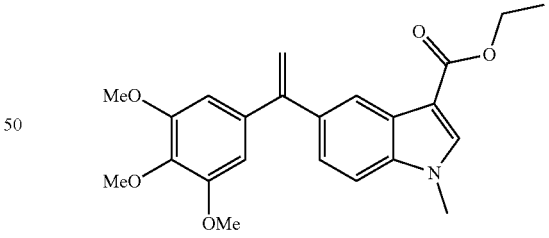

Ethyl 1-methyl-5-(1-(3,4,5-trimethoxyphenyl)vinyl)-1H-indole-3-carboxylate (53)

Compound 53 was prepared according to method A from (Z)-4-methyl-N'-(1-(3,4,5-trimethoxyphenyl)ethylidene) benzenesulfonohydrazide (1 mmol) and ethyl 5-bromo-1-methyl-1H-indole-3-haloindole carboxylate (1.5 mmol). Purification by column chromatography on silica gel gave 352 mg of 53 (yield 89%). Yellow oil; R$_f$=0.15 (EtOAc: cyclohexane, 2:8); $^1$H NMR (300 MHz, CDCl$_3$) (δ ppm): 8.24 (s, 1H), 7.80 (s, 1H), 7.29 (d, J=8.7 Hz, 1H), 7.27-7.22

(m, overlapped with CDCl$_3$, 1H), 6.59 (s, 2H), 5.49 (d, J=1.4 Hz, 1H), 5.43 (d, J=1.4 Hz, 1H), 4.35 (q, J=7.1 Hz, 2H), 3.88 (s, 3H), 3.85 (s, 3H), 3.80 (s, 6H), 1.36 (t, J=7.1 Hz, 3H). $^{13}$C NMR (75 MHz, CDCl$_3$) (δ ppm): 165.1 (C=O), 152.9 (2C), 150.8 (C), 138.1 (C), 137.8 (C), 137.0 (C), 135.6 (CH), 135.5 (C), 126.7 (C), 123.7 (CH), 121.6 (CH), 113.5 (CH$_2$), 109.4 (CH), 107.6 (C), 105.8 (2 CH), 61.0 (OCH$_3$), 59.8 (OCH$_2$), 56.2 (2 OCH$_3$), 33.6 (CH$_3$), 14.6 (CH$_3$). HRMS (ESI) for C$_{23}$H$_{26}$NO$_5$ [M+H]$^+$: calcd 396.1783, found 396.1811.

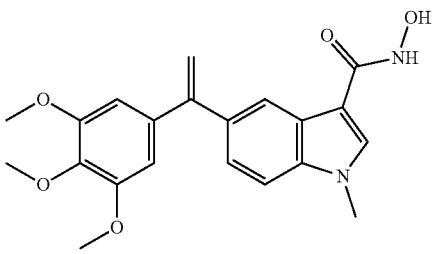 [SMILES: C=C(c1cc(OC)c(OC)c(OC)c1)c1ccc2c(c1)c(C(=O)NO)cn2C]

N-Hydroxy-1-methyl-5-(1-(3,4,5-trimethoxyphenyl)vinyl)-1H-indole-3-carboxamide (25)

This compound was prepared according to method D from ethyl 1-methyl-5-(1-(3,4,5-trimetoxyphenyl)vinyl)-1H-indole-3-carboxylate (53). Purification by HPLC gave 206 mg of 25 (yield 54%). Pink oil; TLC: R$_f$=0.22 (MeOH:dichloromethane, 5:95); $^1$H NMR (300 MHz, DMSO-d$_6$) (δ ppm): 11.97 (s, 1H), 8.09-7.98 (m, 2H), 7.51 (d, J=8.5 Hz, 1H), 7.21 (dd, J=8.5, 1.8 Hz, 1H), 6.59 (s, 2H), 5.48 (s, 1H), 5.41 (s, 1H), 3.86 (s, 3H), 3.71 (s, 6H), 3.70 (s, 3H). $^{13}$C NMR (75 MHz, DMSO) (δ ppm): 165.5 (C=O), 152.5 (2C), 150.1 (C), 137.3 (C), 137.2 (C), 136.8 (C), 136.7 (CH), 134.1 (C), 126.3 (C), 122.7 (CH), 120.3 (CH), 113.5 (CH$_2$), 110.4 (CH), 106.4 (C), 105.5 (2 CH), 60.0 (OCH$_3$), 55.8 (2 OCH$_3$), 33.1 (CH$_3$). HRMS (ESI) for C$_{21}$H$_{22}$N$_2$O$_5$ [M+Na]: calcd 405.1426, found 405.1415.

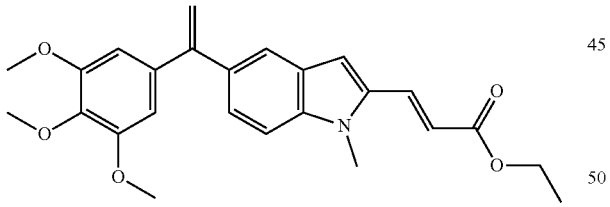

Ethyl (E)-3-(1-methyl-5-(1-(3,4,5-trimethoxyphenyl)vinyl)-1H-indol-2-yl)acrylate (54)

Compound 54 was prepared according to method A from (Z)-4-methyl-N'-(1-(3,4,5-trimethoxyphenyl)ethylidene)benzenesulfonohydrazide (1 mmol) and ethyl (E)-3-(5-bromo-1-methyl-1H-indol-2-yl)acrylate (1.5 mmol). Purification by column chromatography on silica gel gave 232 mg of 54 (yield 55%). Yellow oil; TLC: R$_f$=0.26 (EtOAc:cyclohexane, 2:8); $^1$H NMR (300 MHz, CDCl$_3$) (δ ppm): 7.79 (d, J=15.8 Hz, 1H), 7.32-7.24 (m, overlapped with CDCl$_3$, 1H), 6.94 (s, 1H), 6.63-6.54 (m, 3H), 6.51 (d, J=15.8 Hz, 1H), 5.44 (d, J=1.4 Hz, 1H), 5.39 (d, J=1.4 Hz, 1H), 4.29 (q, J=7.1 Hz, 3H), 3.89 (s, 3H), 3.85 (s, 3H), 3.80 (s, 6H), 1.35 (t, J=7.1 Hz, 3H). $^{13}$C NMR (75 MHz, CDCl$_3$) (δ ppm): 167.8 (C=O), 153.1 (2C), 150.7 (C), 137.9 (C), 137.9 (2C), 137.7 (CH), 135.1 (C), 133.3 (CH), 126.2 (C), 124.1 (CH), 120.3 (CH), 113.6 (CH$_2$), 112.8 (CH), 112.5 (C), 109.5 (CH), 105.8 (CH), 61.0 (CH$_3$), 60.2 (CH$_2$), 56.2 (CH$_3$), 33.3 (CH$_3$), 14.5 (CH$_3$). HRMS (ESI) for C$_{25}$H$_{28}$NO$_5$[M+H]$^+$: calcd 422.1967, found 422.1961.

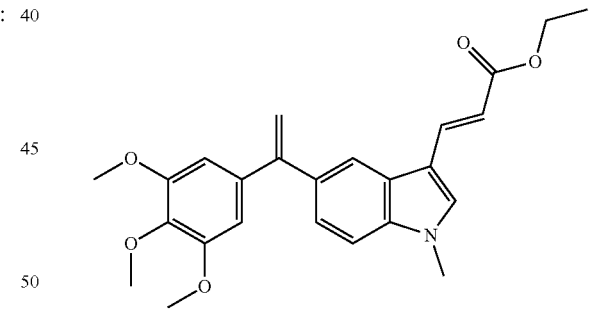

(E)-N-Hydroxy-3-(1-methyl-5-(1-(3,4,5-trimethoxyphenyl)vinyl)-1H-indol-2-yl)acrylamide (12)

This compound was prepared according to method D from ethyl (E)-3-(1-methyl-5-(1-(3,4,5-trimethoxyphenyl)vinyl)-1H-indol-2-yl)acrylate (54). Purification by HPLC gave 216 mg of 12 (yield 53%). Yellow oil; TLC: R$_f$=0.17 (MeOH: dichloromethane, 5:95); $^1$H NMR (300 MHz, Acetone-d$_6$) (δ ppm): 7.74 (d, J=16.4 Hz, 1H), 7.52 (d, J=1.7 Hz, 1H), 7.43 (d, J=8.7 Hz, 1H), 7.23 (dd, J=8.7, 1.7 Hz, 1H), 6.93 (s, 1H), 6.74-6.55 (m, 3H), 5.40 (d, J=1.6 Hz, 1H), 5.39 (d, J=1.8 Hz, 1H), 3.90 (s, 3H), 3.75 (s, 9H). $^{13}$C NMR (75 MHz, Acetone-d$_6$) (δ ppm): 153.9 (C=O), 151.8 (2C), 139.4 (C), 138.9 (C), 138.7 (C), 137.2 (C), 134.3 (2C), 128.7 (CH), 128.3 (C), 124.4 (CH), 121.3 (CH), 119.3 (CH), 112.8 (CH$_2$), 110.3 (CH), 106.6 (2 CH), 103.0 (CH), 60.5 (OCH$_3$), 56.3 (2 OCH$_3$), 33.3 (CH$_3$). HRMS (ESI) for C$_{23}$H$_{25}$N$_2$O$_5$ [M+H]$^+$: calcd 409.1771, found 409.1763.

Ethyl (E)-3-(1-methyl-5-(1-(3,4,5-trimethoxyphenyl)vinyl)-1H-indol-3-yl)acrylate (55)

Compound 55 was prepared according to method A from (Z)-4-methyl-N'-(1-(3,4,5-trimethoxyphenyl)ethylidene)benzenesulfonohydrazide (1 mmol) and ethyl (E)-3-(5-bromo-1-methyl-1H-indol-3-yl)acrylate (1.5 mmol). Purification by column chromatography on silica gel gave 380 mg of 55 (yield 90%). Yellow oil; TLC: R$_f$=0.25 (EtOAc:cyclohexane, 2:8); $^1$H NMR (300 MHz, CDCl$_3$) (δ ppm): 7.97 (s, 1H), 7.91 (d, J=15.9 Hz, 1H), 7.39 (s, 1H), 7.31 (d, J=8.6 Hz, 1H), 7.27 (d, J=8.6 Hz, 1H), 6.63 (s, 2H), 6.40 (d, J=15.9 Hz, 1H), 5.49 (s, 2H), 4.29 (q, J=7.1 Hz, 2H), 3.92 (s, 3H), 3.85 (s, 3H), 3.83 (s, 6H), 1.37 (t, J=7.1 Hz, 3H). $^{13}$C NMR (75 MHz, CDCl$_3$) (δ ppm): 168.3 (C=O), 153.0 (2C), 150.8 (C), 138.0 (C), 137.9 (2C), 137.7 (CH), 135.0 (C), 133.3 (CH), 126.1 (C), 124.1 (CH), 120.3 (CH), 113.6 (CH$_2$), 112.9 (CH), 112.5 (C), 109.5 (CH), 105.8 (CH), 61.0 (CH$_3$), 60.2 (CH$_2$), 56.2 (CH$_3$), 33.4 (CH$_3$), 14.5 (CH$_3$). HRMS (ESI) for C$_{25}$H$_{28}$NO$_5$ [M+H]$^+$: calcd 422.1967, found 422.1953.

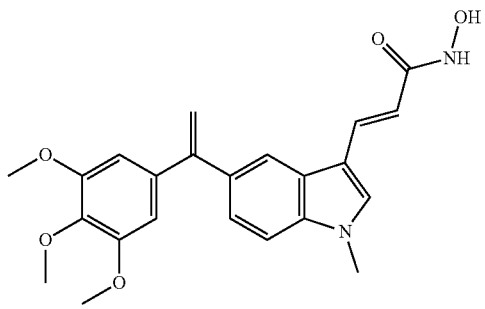 [SMILES: C=C(c1cc(OC)c(OC)c(OC)c1)c1ccc2c(c1)c(/C=C/C(=O)NO)cn2C]

(E)-N-Hydroxy-3-(1-methyl-5-(1-(3,4,5-trimethoxyphenyl)vinyl)-1H-indol-3-yl)acrylamide (11)

This compound was prepared according to method D from ethyl (E)-3-(1-methyl-5-(1-(3,4,5-trimethoxyphenyl)vinyl)-1H-indol-3-yl)acrylate (55). Purification by HPLC gave 220 mg of 11 (yield 54%). Yellow oil; TLC: R$_f$=0.18 (MeOH: dichloromethane, 5:95); $^1$H NMR (300 MHz, Acetone-d$_6$) (δ ppm): 10.14 (s, 1H), 8.45 (s, 1H), 7.96 (s, 1H), 7.80 (d, J=15.5 Hz, 1H), 7.68 (s, 1H), 7.43 (d, J=8.4, 1H), 7.16 (d, J=8.4 Hz, 1H), 6.73-6.45 (m, 1H), 5.49 (s, 1H), 5.43 (s, 1H), 3.89 (s, 3H), 3.76 (s, 3H). $^{13}$C NMR (75 MHz, Acetone-d$_6$) (δ ppm): 154.0 (C=O), 152.0 (2C), 151.9 (C), 138.8 (C), 138.4 (C), 135.3 (2C), 134.7 (CH), 126.8 (C), 124.3 (CH), 123.5 (CH), 120.5 (CH), 118.4 (CH), 113.5 (CH$_2$), 110.6 (CH), 106.7 (2 CH), 60.5 (OCH$_3$), 56.4 (2 OCH$_3$), 33.3 (CH$_3$). HRMS (ESI) for C$_{23}$H$_{25}$N$_2$O$_5$ [M+H]$^+$: calcd 409.1771, found 409.1782.

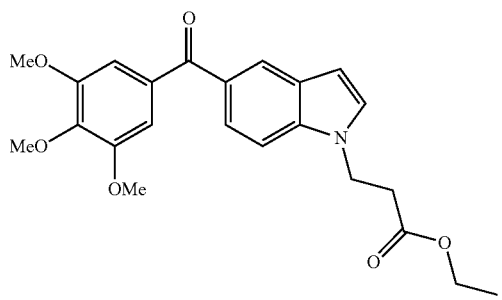 [SMILES: CCOC(=O)CCn1ccc2cc(C(=O)c3cc(OC)c(OC)c(OC)c3)ccc21]

Ethyl 3-(5-(1-(3,4,5-trimethoxyphenyl)vinyl-1H-indol-1-yl)propanoate (56)

Compound 56 was prepared according to method A from (Z)-4-methyl-N'-(1-(3,4,5-trimethoxyphenyl)ethylidene)benzenesulfonohydrazide (1 mmol) and ethyl 3-(5-bromo-1H-indol-1-yl)propanoate (1.5 mmol). Purification by column chromatography on silica gel gave 143 mg of 56 (yield 35%). Yellow oil; TLC: R$_f$=0.22 (EtOAc: cyclohexane, 2:8); $^1$H NMR (300 MHz, CDCl$_3$) (δ ppm): 7.62 (d, J=1.6 Hz, 1H), 7.30 (d, J=8.5 Hz, 1H), 7.23 (dd, J=8.5, 1.6 Hz, 1H), 7.15 (d, J=3.2 Hz, 1H), 6.61 (s, 2H), 6.47 (d, J=3.2 Hz, 1H), 5.43 (d, J=1.5 Hz, 1H), 5.36 (d, J=1.5 Hz, 1H), 4.46 (t, J=6.8 Hz, 2H), 4.13 (q, J=7.1 Hz, 2H), 3.89 (s, 3H), 3.80 (s, 6H), 2.83 (t, J=6.8 Hz, 2H), 1.22 (t, J=7.1 Hz, 3H). $^{13}$C NMR (75 MHz, CDCl$_3$) (δ ppm): 164.7 (C=O), 152.9 (2C), 150.3 (C), 133.0 (2C), 129.2 (C), 128.6 (CH), 122.6 (CH), 121.1 (CH), 120.9 (C), 112.7 (CH$_2$), 109.7 (C), 108.8 (CH), 105.9 (2 CH), 102.1 (CH), 56.2 (3 OCH$_3$), 42.0 (OCH$_2$), 35.1 (CH$_2$), 29.8 (CH$_2$), 14.2 (CH$_3$). HRMS (ESI) for C$_{24}$H$_{28}$NO$_5$ ([M+H]$^+$): calcd 410.1967, found 410.1967

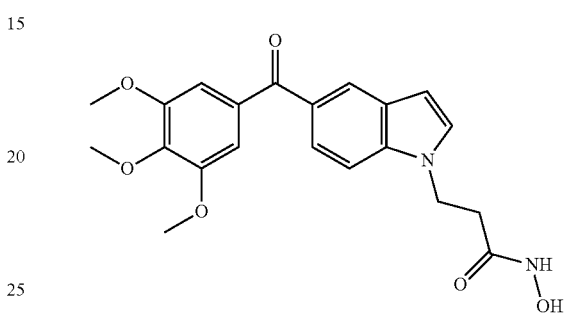

N-Hydroxy-3-(5-(1-(3,4,5-trimethoxyphenyl)vinyl)-1H-indol-1-yl)propanamide (44)

This compound was prepared according to method D from ethyl 3-(5-(1-(3,4,5-trimethoxyphenyl)vinyl-1H-indol-1-yl)propanoate (56). Purification by HPLC gave 140 mg of 44 (yield 35%). Brown oil; TLC: R$_f$=0.18 (MeOH: dichloromethane, 5:95); $^1$H NMR (300 MHz, CDCl$_3$) (δ ppm): 8.12 (s, 1H), 7.78 (d, J=8.3 Hz, 1H), 7.42 (d, J=8.3 Hz, 1H), 7.24 (d, J=3.4 Hz, 2H), 7.07 (s, 2H), 6.59 (d, J=3.4 Hz, 1H), 5.41 (s, 1H), 5.36 (s, 1H), 4.51 (t, J=6.7 Hz, 2H), 3.94 (s, 3H), 3.86 (s, 6H), 2.93 (t, J=6.7 Hz, 2H). $^{13}$C NMR (75 MHz, CDCl$_3$) (δ ppm): 164.1 (C=O), 152.8 (2C), 141.6 (C), 141.5 (C), 138.1 (2C), 134.1 (C), 129.6 (CH), 128.0 (C), 125.4 (CH), 124.1 (CH), 112.5 (CH$_2$), 109.1 (CH), 107.8 (2 CH), 103.7 (CH), 61.1 (OCH$_3$), 56.4 (2 OCH$_3$), 41.9 (CH$_2$), 34.6 (CH$_2$). HRMS (ESI) for C$_{22}$H$_{25}$N$_2$O$_5$ [M+H]$^+$: calcd 397.1763, found 397.1763.

In Vitro Biological Study of the Compounds of the Invention

Representative molecules were prepared and their effect on the proliferation of human cancer cell lines and their ability to inhibit tubulin polymerisation were studied.

1—Cytotoxic Activity.

The cytotoxic activity of the prepared compounds was evaluated on various human cancer cell lines. The selected line was incubated at 37° C. in the presence of one of the novel compounds, added to the culture medium at various concentrations. The inhibitory concentration inducing 50% cell death (IC$_{50}$) was determined after 72 hours of incubation for each compound (Tables 1 and 2).

TABLE 1

Cytotoxic activity of the compounds of the invention compared with the reference, isoCA-4.

| Number | Structure | HCT116[a] IC$_{50}$ (nM) | K562R IC$_{50}$ (nM) | ITP[b] IC$_{50}$ (μM) |
|---|---|---|---|---|
| 1 | 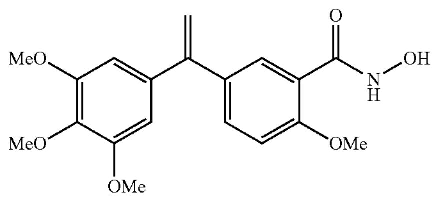 [SMILES: C=C(c1cc(OC)c(OC)c(OC)c1)c1ccc(OC)c(C(=O)NO)c1] | 233 ± 22 | nd | 20 ± 1.2 |
| 2 | 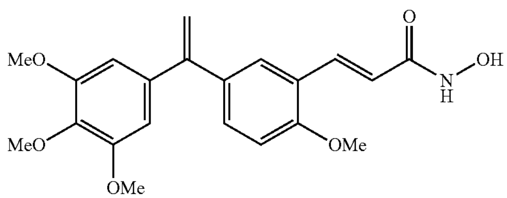 [SMILES: C=C(c1ccc(OC)c(/C=C/C(=O)NO)c1)c1cc(OC)c(OC)c(OC)c1] | 2.5 | 1.6 | 1.6 ± 0.4 |
| 3 | 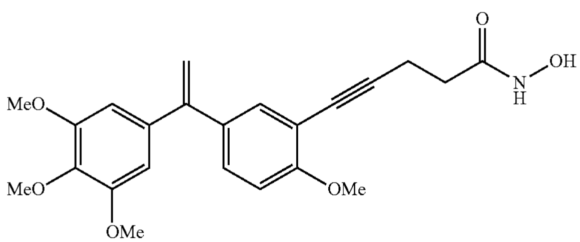 [SMILES: C=C(c1ccc(OC)c(C#CCCC(=O)NO)c1)c1cc(OC)c(OC)c(OC)c1] | 35 | 33 | 1.7 ± 0.3 |
| 4 | 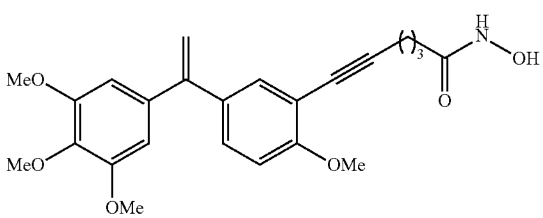 | 372 ± 5 | nd | 18 ± 1.2 |
| 8 | 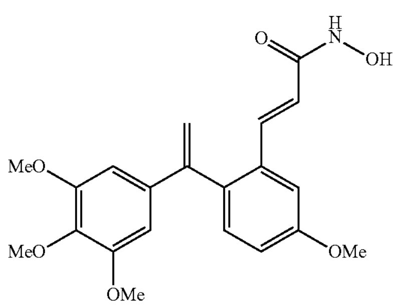 [SMILES: C=C(c1cc(OC)c(OC)c(OC)c1)c1ccc(OC)cc1/C=C/C(=O)NO] | 2 ± 0.1 | nd | 2.1 ± 0.4 |
| 11 | 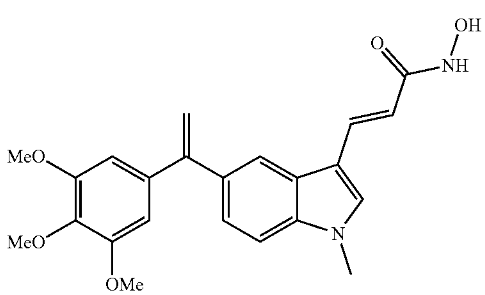 [SMILES: C=C(c1cc(OC)c(OC)c(OC)c1)c1ccc2c(c1)c(/C=C/C(=O)NO)cn2C] | 2.2 ± 0.26 | nd | 3.7 ± 0.5 |

TABLE 1-continued

Cytotoxic activity of the compounds of the invention compared with the reference, isoCA-4.

| Number | Structure | HCT116[a] IC$_{50}$ (nM) | K562R IC$_{50}$ (nM) | ITP[b] IC$_{50}$ (μM) |
|---|---|---|---|---|
| 12 | 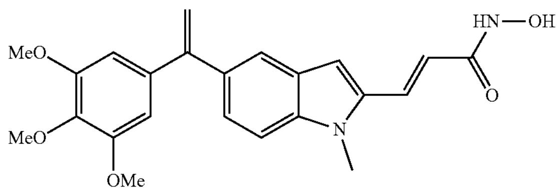 [SMILES: C=C(c1cc(OC)c(OC)c(OC)c1)c1ccc2c(c1)cc(/C=C/C(=O)NO)n2C] | 12 ± 2.5 | nd | 5.4 ± 1.2 |
| 17 | 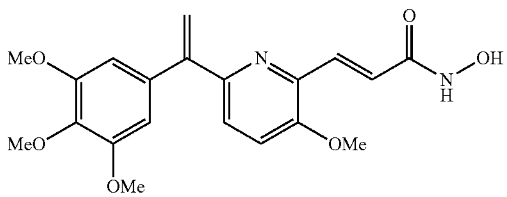 [SMILES: C=C(c1cc(OC)c(OC)c(OC)c1)c1ccc(OC)c(/C=C/C(=O)NO)n1] | 37.2 ± 0.60 | nd | 7.5 ± 1.5 |
| 25 | 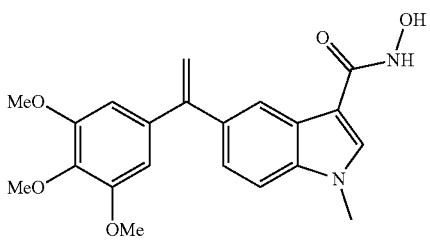 [SMILES: C=C(c1cc(OC)c(OC)c(OC)c1)c1ccc2c(c1)c(C(=O)NO)cn2C] | 30 ± 1.5 | nd | 7.3 ± 3.3 |
| 43 | 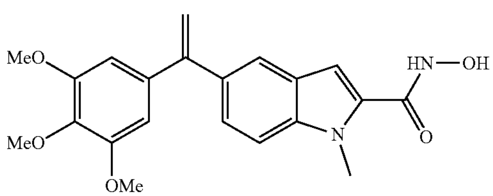 | 36 ± 4 | nd | 81 ± 15 |
| 44 | 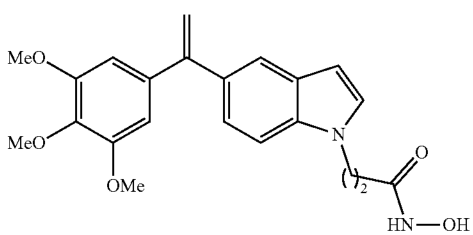 | 393 ± 4.1 | nd | 22 ± 2 |
| isoCA-4 | 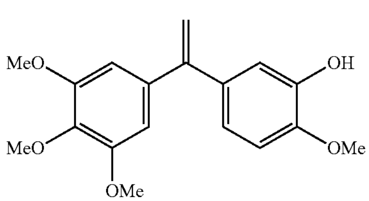 [SMILES: C=C(c1ccc(OC)c(O)c1)c1cc(OC)c(OC)c(OC)c1] | 2 | nd | 1.8 ± 0.4 |

Compound 2 showed excellent antiproliferative activity with an IC$_{50}$ of 2.5 nM on cell line HCT116 (colorectal carcinoma), similar to that of the reference molecule, isoCA-4. In addition, 2 is also cytotoxic at nanomolar concentrations (IC$_{50}$=1.6 nM) to cell line K 562R (human leukaemia derived from imatinib-resistant tumours). Compound 3, which has an acetylenic function, also proved to be cytotoxic at nanomolar concentrations. Compounds 11, 12, 25 and 43, which have an indole nucleus, also exhibit excellent antiproliferative activity, as does compound 17, which has a pyridine nucleus.

TABLE 2

Cytotoxic activity of compound 2 on various human tumour lines.
Cytotoxicity of 2 IC$_{50}$ (nM)

| A549 | K562 | MCF7 | PC3 | U87 | U2OS | SOJ6 | BxPC3 | MiaPaCa 2 |
|------|------|------|-----|-----|------|------|-------|-----------|
| 1.7  | 1.6  | 2.0  | 2.4 | 1.6 | 1.9  | 6.8  | 2.9   | 5.1       |

Compound 2 also showed cytotoxicity to other human tumour lines, such as lung cancer (A549), chronic myeloid leukaemia (K562), breast cancer (MCF7), prostate cancer (PC3), glioblastoma (U87), osteosarcoma (U2OS), and to pancreatic tumour cell lines (SOJ6, BxPC-3 and MiaPaCa-2) with IC$_{50}$ values between 1.6 nM and 6.8 nM.

2—Inhibition of Tubulin Polymerisation (ITP).

To verify whether the antiproliferative activities of novel molecules 2 and 3 correlate with their anti-tubulin effects, their ability to inhibit tubulin polymerisation into microtubules was measured in vitro. Tubulin was purified from sheep brains according to the Shelanski method by two assembly-disassembly cycles. The stock solution (15-20 mg/mL), stored at −196° C., is thawed and diluted in the assembly buffer (0.1 M MES, 0.5 mM MgCl$_2$, 1 mM EGTA, and 1 mM GTP, pH 6.6) to a final concentration of 10 µM. Tubulin assembly was monitored by fluorescence on 96-well plates according to the method of Barron et al. The tubulin solution (10 µM, 100 µL per well) was supplemented with inhibitor (DMSO, 1 µL) and incubated for 45 min at room temperature. GTP (1 mM final) was then added, the solution was rapidly mixed and the fluorescence (λex=350 nm, λem=440 nm) was measured on a Wallac Victor fluorimeter (Perkin Elmer). Fifty-percent inhibition of the maximum assembly rate (IC$_{50}$) was determined in duplicate or triplicate on 10 concentrations flanking the IC$_{50}$. For comparison, deoxypodophyllotoxin and isoCA-4 were used as positive controls.

Compounds 2 and 3 have a strong ability to inhibit tubulin assembly with IC$_{50}$ values of 1.6 and 1.7 µM, respectively, very close to those of the control molecule, isoCA-4. A strong correlation between inhibition of tubulin polymerisation and cytotoxic activity is thus established within these two compounds.

3—Inhibition of HDAC Activity.

Figure 2:
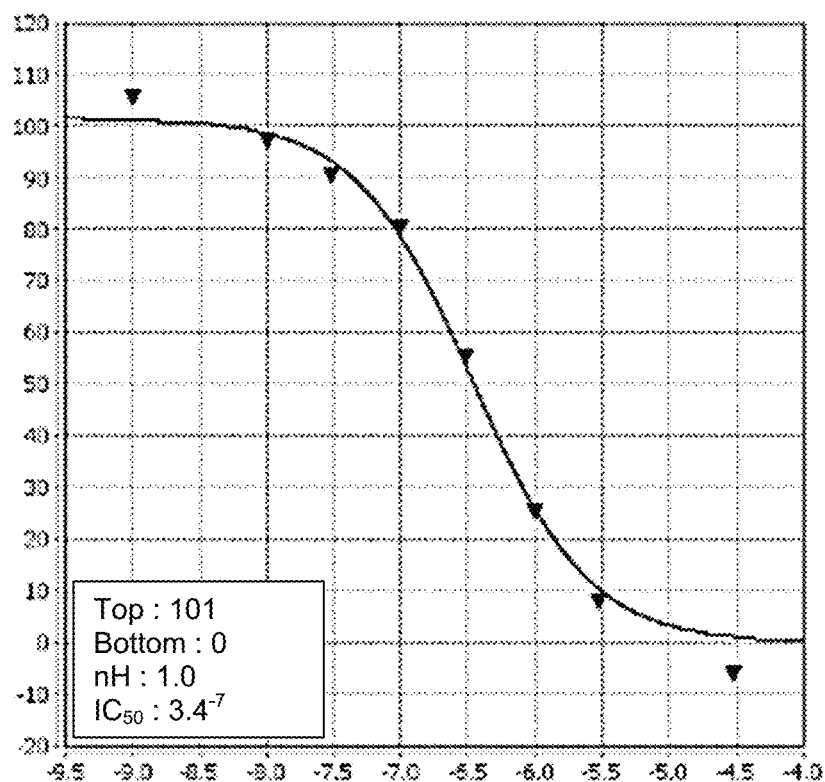
FIG. 2 is an illustration allowing the determination of the $IC_{50}$ of compound 2 with respect to HDAC8. More particularly.
Figure 3:
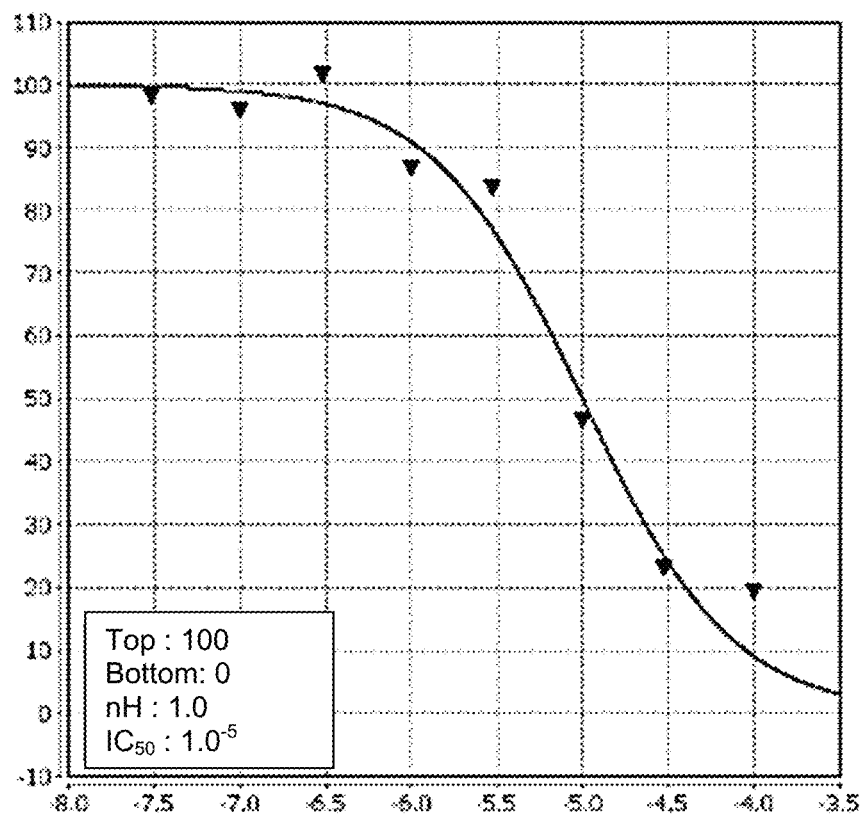
FIG. 3 is an illustration allowing the determination of the $IC_{50}$ of compound 2 with respect to HDAC11. More particularly.

The activity of compounds 2 and 3 on inhibition of HDACs 1 to 11 was also tested. Compound 2 showed selective inhibitory activity against HDAC8 (FIG. 1) with an IC$_{50}$ (0.34 µM, FIG. 2) similar to that of the reference molecule, trichostatin A (IC$_{50}$=0.32 µM).

Figure 4:
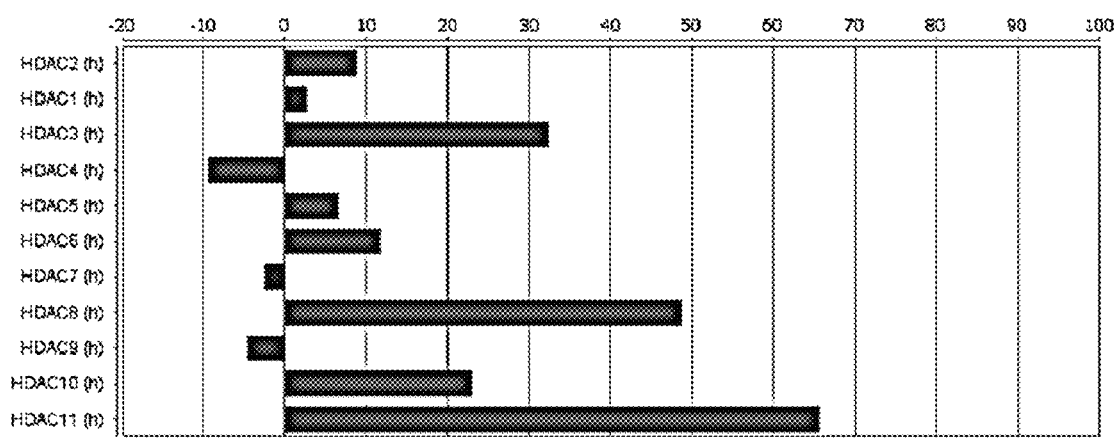
FIG. 4 describes the inhibitory potential of molecule 3 with respect to HDACs 1 to 11, with more particularly selective activity for HDAC8 and HDAC11. More particularly.
Figure 5:
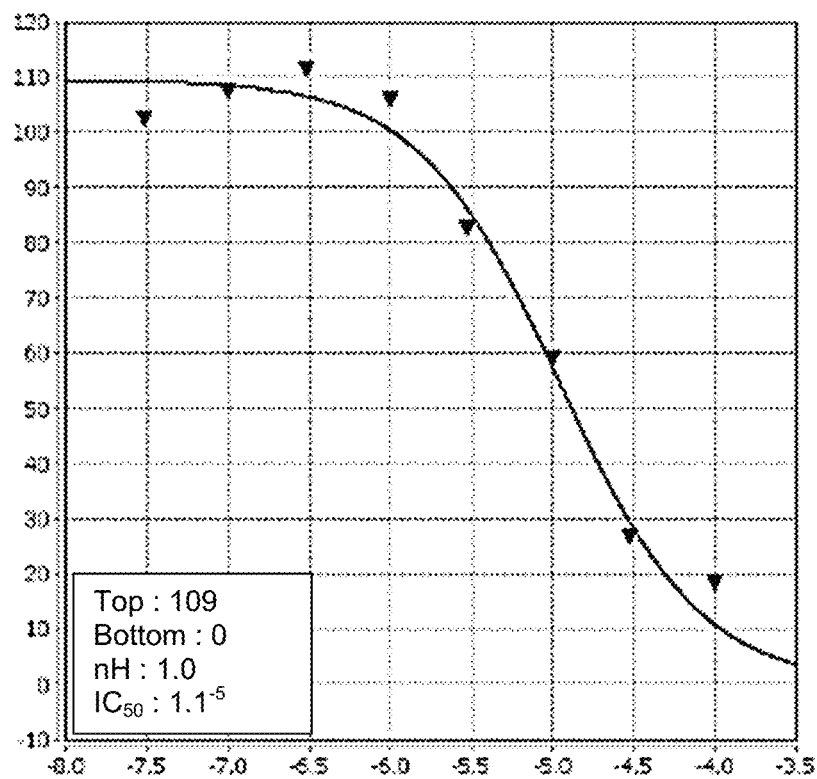
FIG. 5 is an illustration allowing the determination of the $IC_{50}$ of compound 3 with respect to HDAC11. More particularly.

Advantageously, HDAC8 showed therapeutic activity in malignant lymphomas. Compound 3 showed selective inhibitory activity against HDAC8 and HDAC11 (FIG. 4) with an IC$_{50}$ of 11 µM (FIG. 5).

Figure 6:
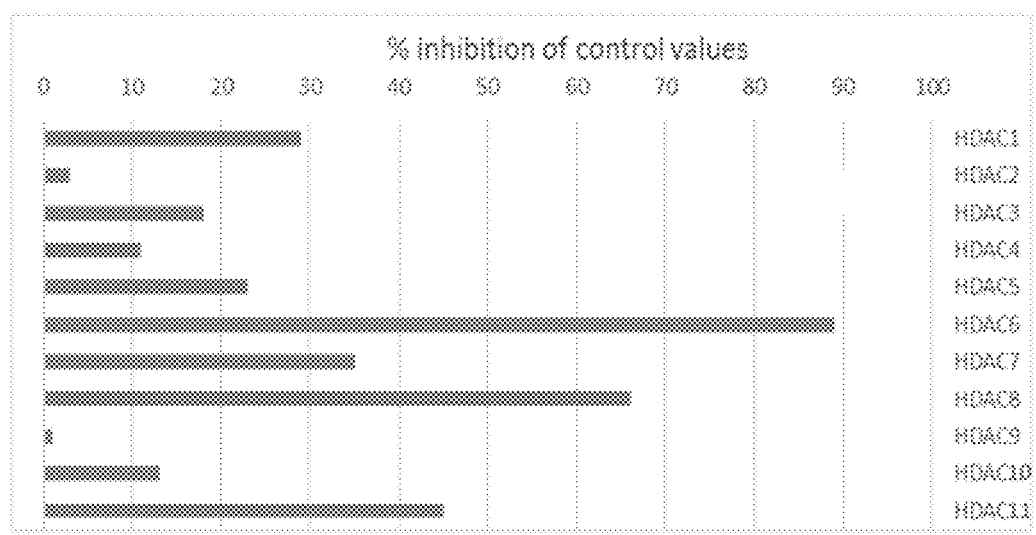
FIG. 6 describes the inhibitory potential of molecule 11 with respect to HDACs 1 to 11, with more specifically selective activity for HDAC6 and HDAC8. More particularly.

Compound 11 showed selective inhibitory activity against HDAC6 and HDAC8 (FIG. 6).

Figure 7:
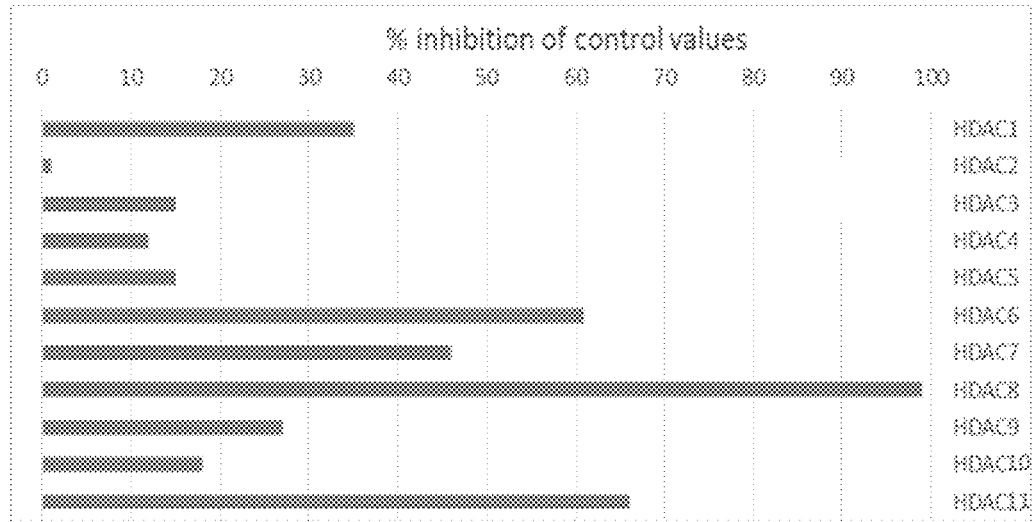
FIG. 7 describes the inhibitory potential of molecule 8 with respect to HDACs 1 to 11, with more particularly selective activity for HDAC6, HDAC8 and HDAC11. More particularly.
Figure 8:
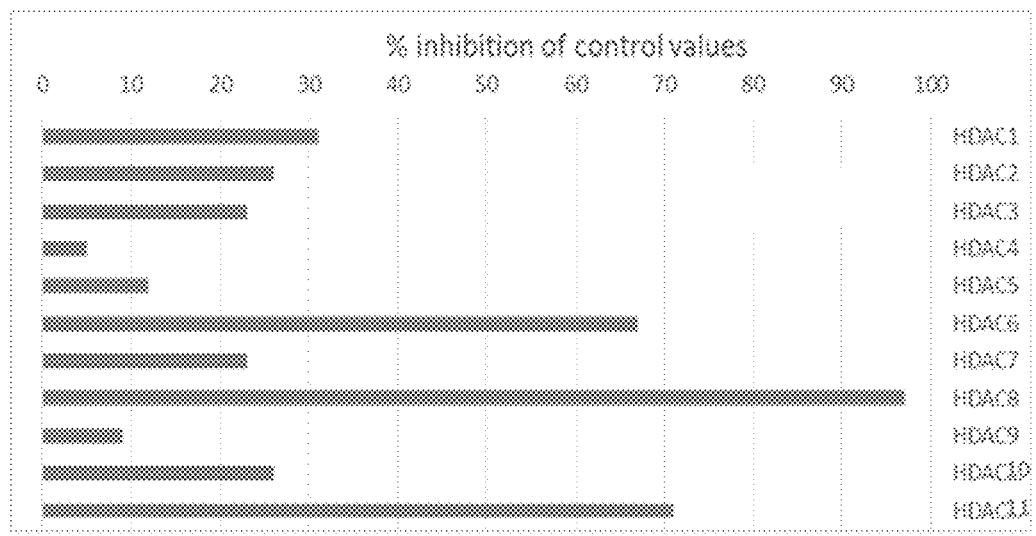
FIG. 8 describes the inhibitory potential of molecule 12 with respect to HDACs 1 to 11, with more specifically selective activity for HDAC6, HDAC8 and HDAC11. More particularly.

Compound 8 showed selective inhibitory activity against HDAC6, HDAC8 and HDAC11 (FIG. 7), as did compound 12 (FIG. 8).

The invention claimed is:
1. A compound having the following Formula (II):

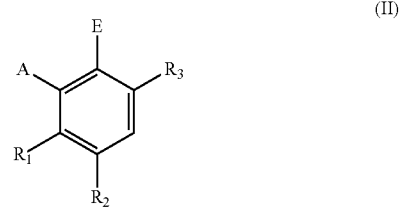

(II)

wherein:
R$_3$ represents a group A$_1$ having the following general formula:

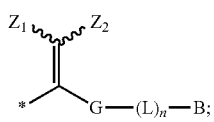

and
B is selected from:

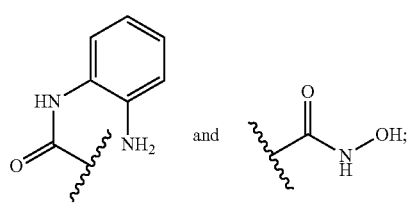 [SMILES: *C(=O)Nc1ccccc1N ; "and" ; *C(=O)NO]

n represents an integer selected from 0 or 1;
L represents:
—(CH$_2$)$_r$—;
—CH=CH—(CH$_2$)$_r$—;
—CH=CH—CH=CH—(CH$_2$)$_r$—;
—C=C—CH=CH—(CH$_2$)$_r$—;
—C≡C—(CH$_2$)$_r$—; or —C≡C—CH=CH—(CH$_2$)$_r$—;

where r is an integer from 0 to 6;

Z$_1$ represents a hydrogen atom, or a halogen atom;

Z$_2$ represents an atom selected from a hydrogen and a halogen, or a group selected from a nitrile, and a group B, provided that if Z$_2$=B then the group -(L)$_n$-B is absent from G;

the bonds ⁓ mean that the double bond bearing Z$_1$, respectively, Z$_2$ is of E or Z stereochemistry;

* is the carbon atom bearing R$_2$ or R$_3$;

G represents a phenyl or a heteroaryl:
  When G is a phenyl, it is substituted by a group R$_{20}$ selected from OMe and SMe in the para position, relative to the position of the double bond bearing Z$_1$ and Z$_2$;
  When G is a heteroaryl, it is selected from pyridines, indoles, 1-methylindoles, indolines, carbazoles, benzothiophenes and benzofurans;

R$_2$ represents an —OMe group;

E represents a hydrogen atom;

A represents an —OMe group;

R$_1$ represents an —OMe group;

2. The compound according to claim 1, wherein the group A$_1$ is selected from the groups having the following general formulas:

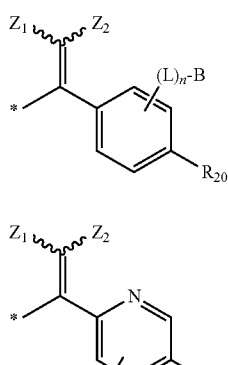
A$_1$-1

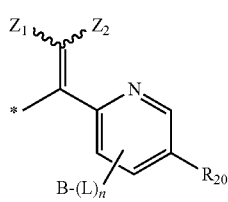
A$_1$-2

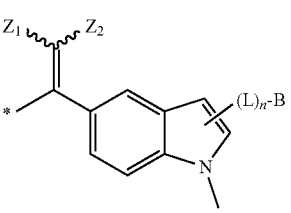
A$_1$-3

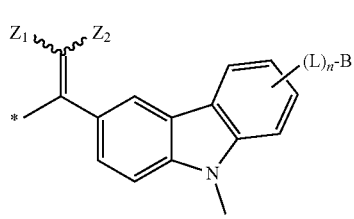
A$_1$-4

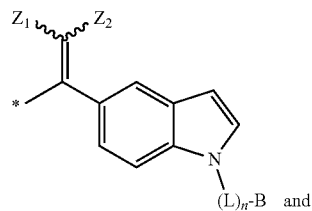
A$_1$-5

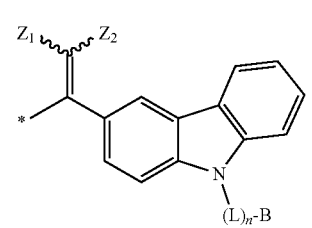
A$_1$-6 where:
  Z$_1$ and Z$_2$ each independently represent a hydrogen atom, a halogen atom selected from fluorine, chlorine and bromine, or a nitrile group;
  R$_{20}$, B, L and n are as defined in claim 1, and;
  the bonds ⁓ mean that the double bond bearing Z$_1$, respectively, Z$_2$ is of E or Z stereochemistry;
  * is the carbon atom bearing R$_3$.

3. The compound according to claim 1, wherein the group A1 is selected from the groups having the following general formulas:

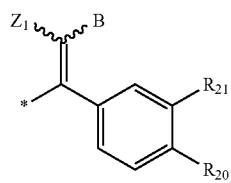
A$_1$-7

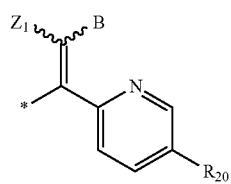
A$_1$-8

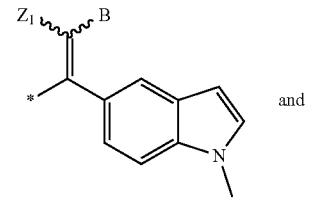
A$_1$-9 and

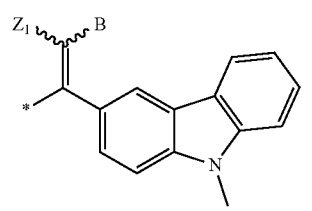
A$_1$-10 where:

Z₁ represents a hydrogen atom, a halogen atom selected from fluorine, chlorine and bromine, or a nitrile group;

R$_{20}$, B, are as defined in claim 1;

R$_{21}$ represents a hydrogen atom, or a group selected from —OH, —NH$_2$, F, N$_3$, —C≡CH, —C≡C(CH$_2$)$_m$OH where m is an integer between 0 and 5, (E)-CH=CHCH$_2$OH, and (E)-CH=CHCOOR where R is a hydrogen atom or a (C$_1$ to C4)alkyl group, and;

the bonds ⌇ mean that the double bond bearing Z₁, respectively, Z$_2$ is of E or Z stereochemistry;

\* is the carbon atom bearing R$_3$.

4. The compound according to claim 1, wherein it has the following formula:

1
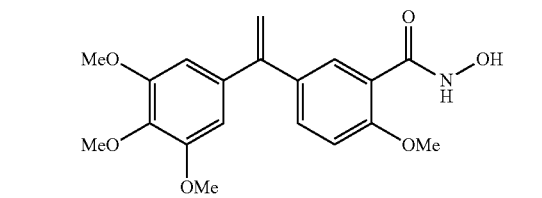

2
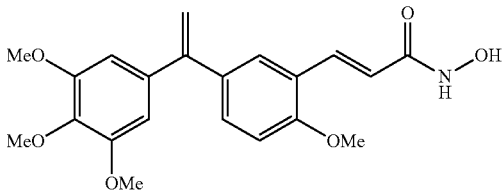

3
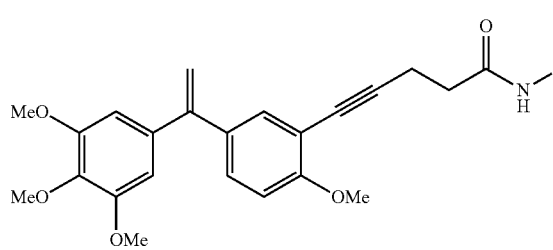

4
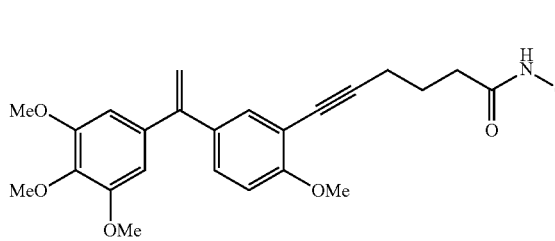

5
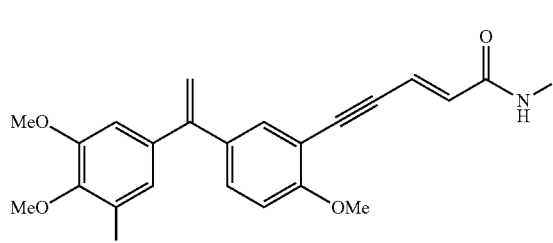

-continued

6
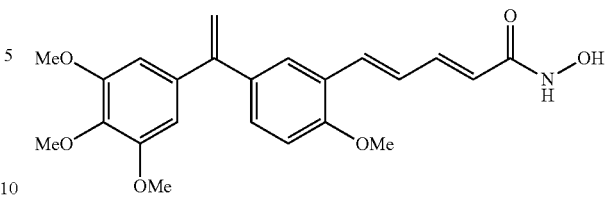

8
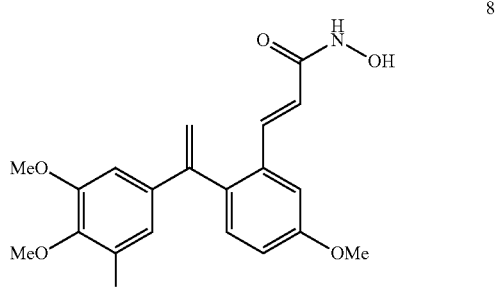

11
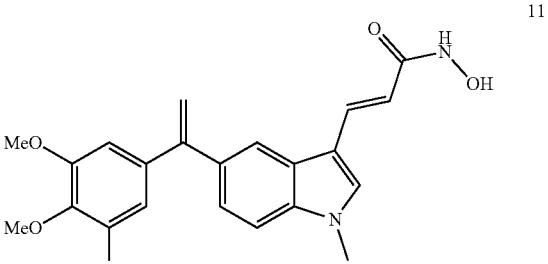

12
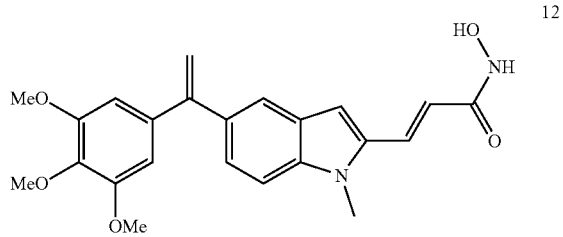

13
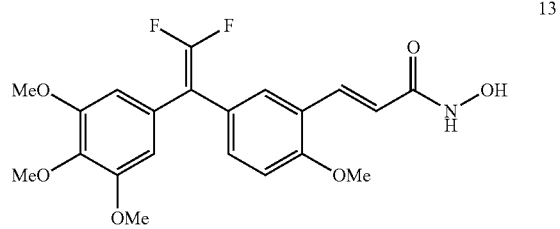

14
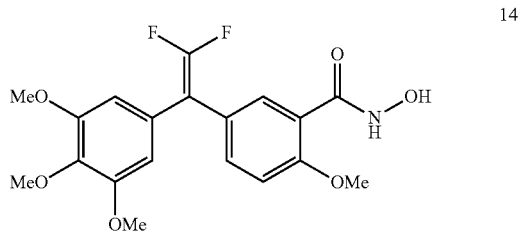

15
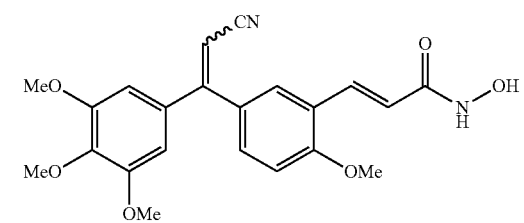
16
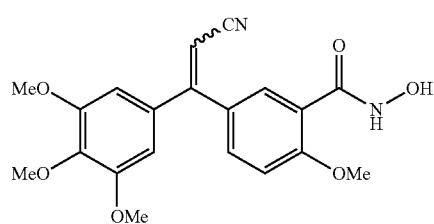
17
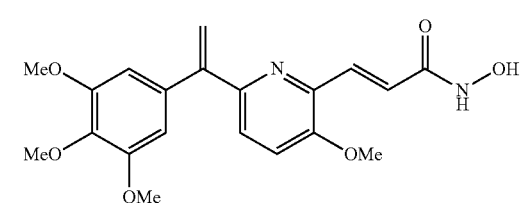
18
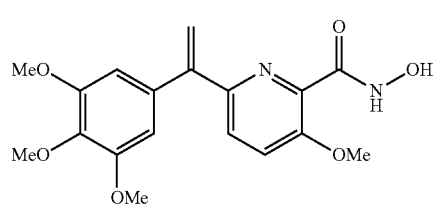
19
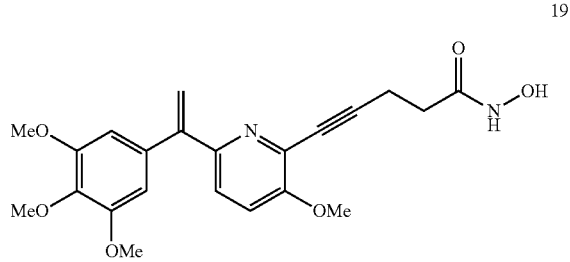
20
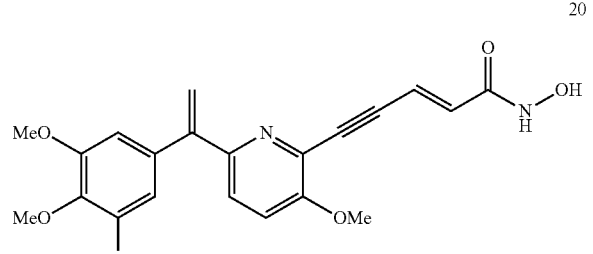
21
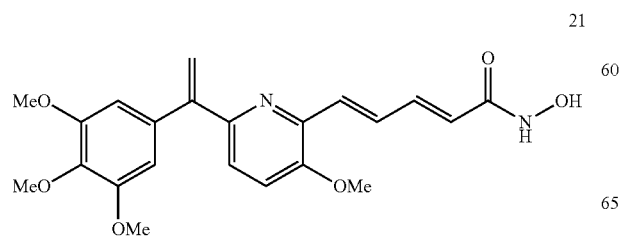
25
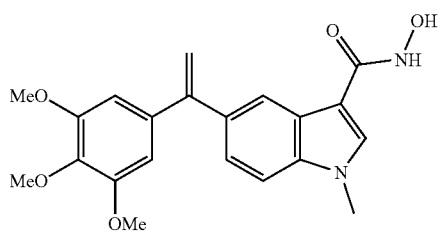
27
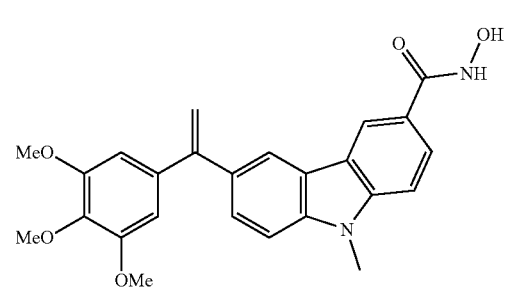
26
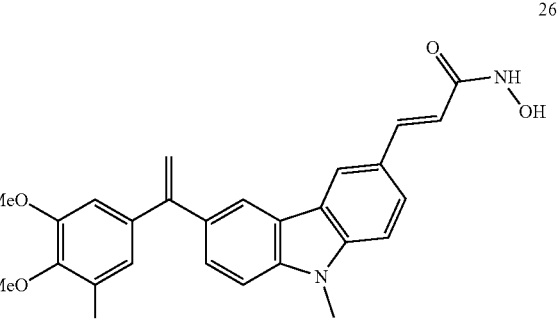
32
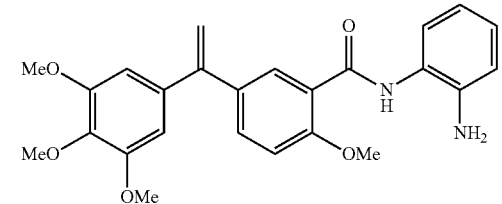
33
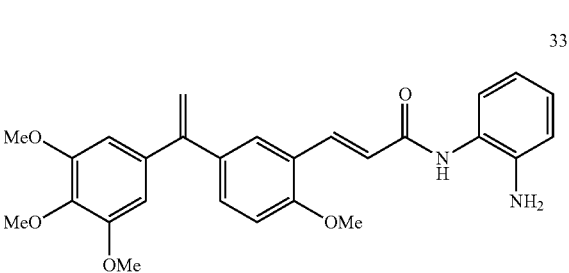
34
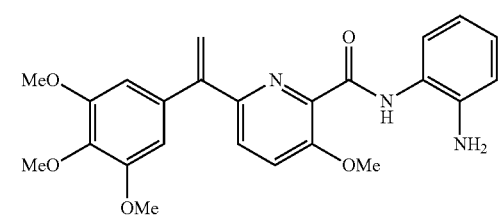

-continued
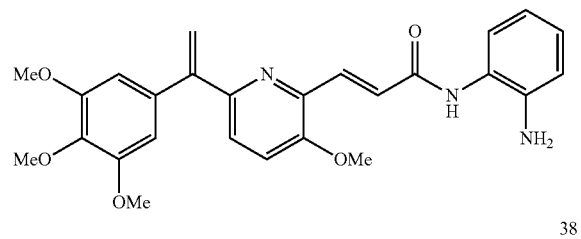
35
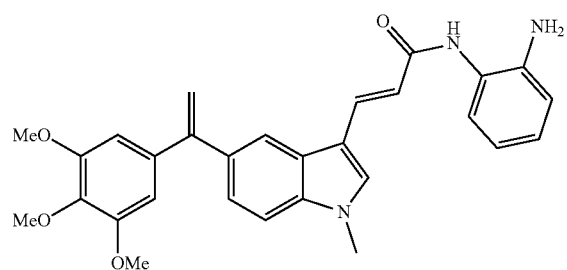
38
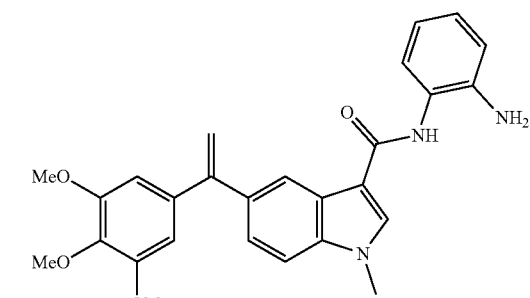
39
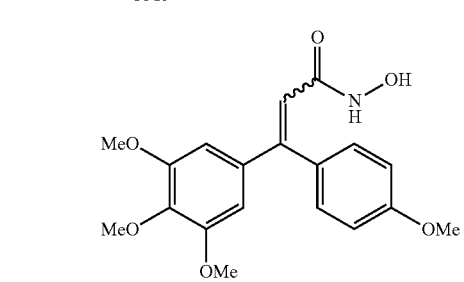
42
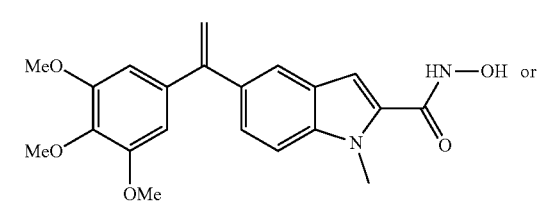
43
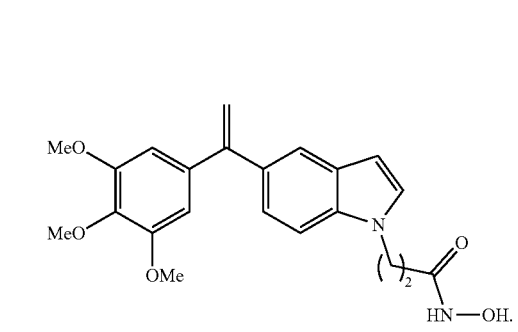
44
5. The compound according to claim 1, wherein it has the following formula:
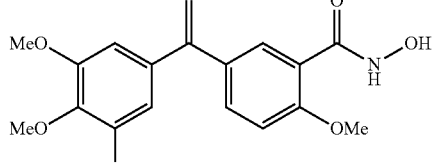
1
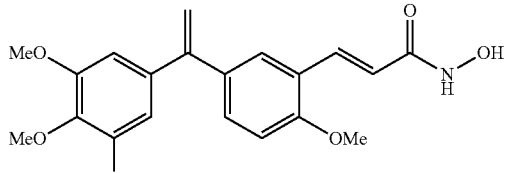
2
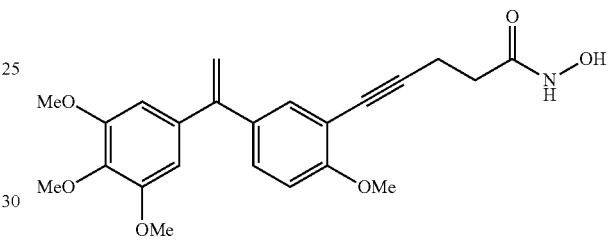
3
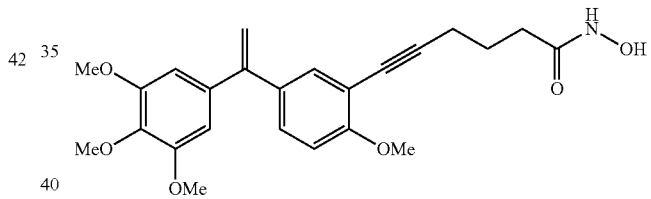
4
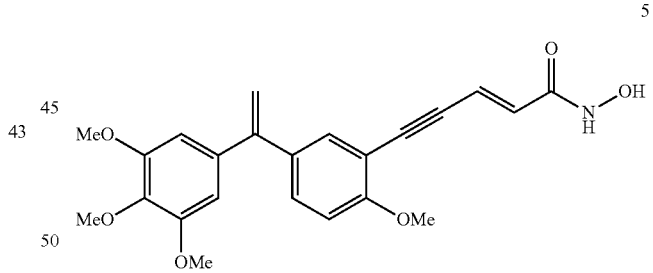
5
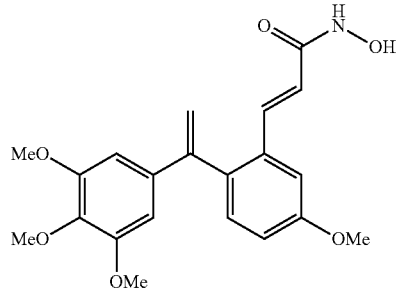
8

-continued

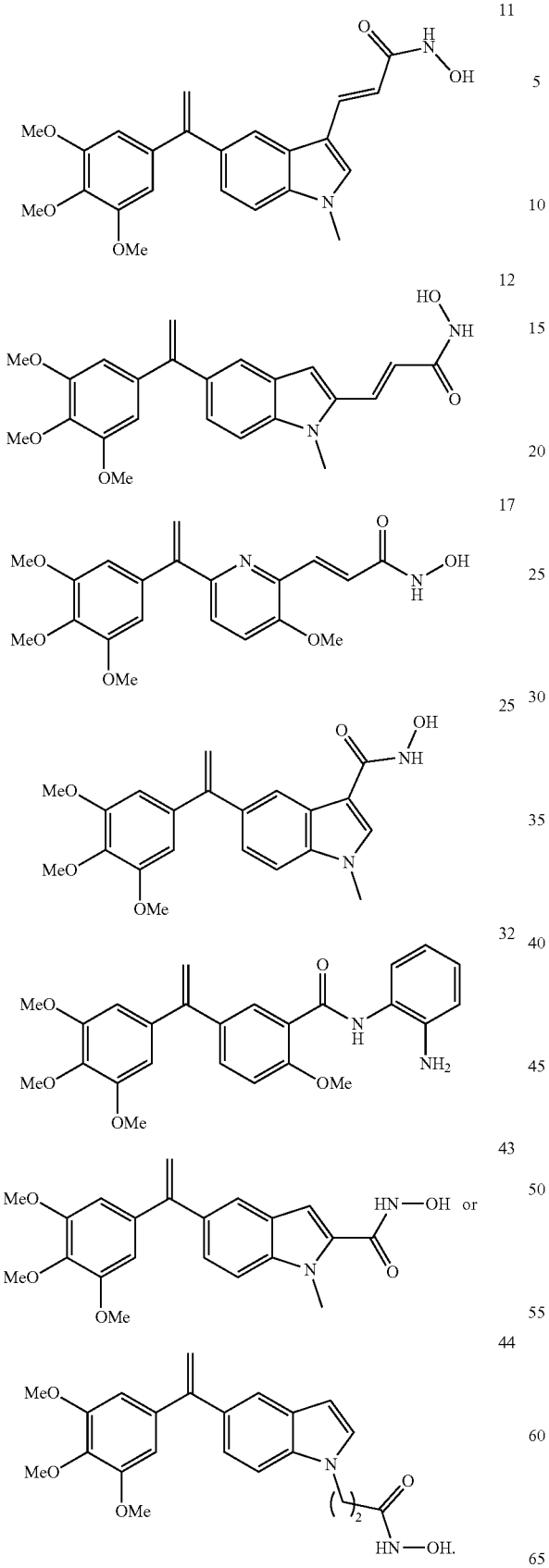

6. A process for preparing a compound of claim 1 having the formula (II):

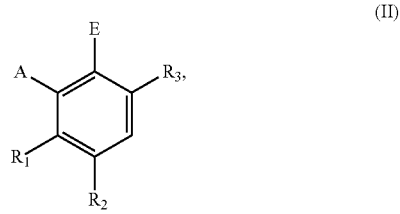

Wherein
R$_3$ represents a group A$_1$ having the following general formula:

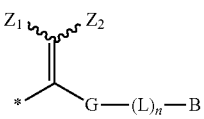

wherein:
B is selected from

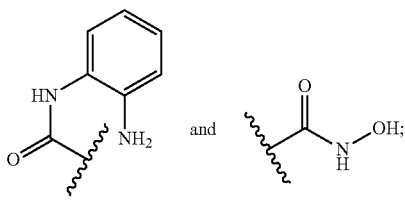 [SMILES: *C(=O)Nc1ccccc1N ; "and" ; *C(=O)NO]

n represents an integer selected from 0 or 1;
L represents:
- —(CH$_2$)$_r$—;
- —CH═CH—(CH$_2$)$_r$—;
- —CH═CH—CH═CH—(CH$_2$)$_r$—;
- —C═C—CH═CH—(CH$_2$)$_r$—;
- —C≡C—(CH$_2$)$_r$—; or
- —C≡C—CH═CH—(CH$_2$)$_r$—;

where r is an integer from 0 to 6;
Z$_1$ represents a hydrogen atom, or a halogen atom;
Z$_2$ represents an atom selected from a hydrogen and a halogen, or a group selected from a nitrile, and a group B, provided that if Z$_2$═B then the group -(L)$_n$-B is absent from G;
the bonds ⁓ mean that the double bond bearing Z$_1$, respectively, Z$_2$ is of E or Z stereochemistry;
* is the carbon atom bearing R$_2$ or R$_3$;
G represents a phenyl or a heteroaryl:
When G is a phenyl, it is substituted by a group R$_{20}$ selected from OMe and SMe in the para position, relative to the position of the double bond bearing Z$_1$ and Z$_2$;
When G is a heteroaryl, it is selected from pyridines, indoles, 1-methylindoles, indolines, carbazoles, benzothiophenes and benzofurans;
R$_2$ represents an —OMe group;
E represents a hydrogen atom;
A represents an —OMe group;
R$_1$ represents an —OMe group;

the process comprising the following successive steps:
1. reacting a compound having the following general formula:

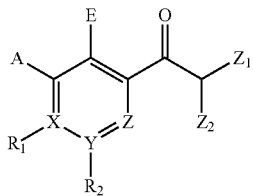

with tosylhydrazine to give the tosylhydrazone having the following general formula:

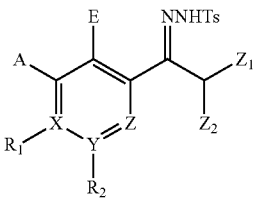

where X, Y, Z independently represent a carbon atom, and $Z_1$, $Z_2$, A, E, $R_1$, $R_2$, are as defined above;
2. metal-catalysed coupling the tosylhydrazone obtained in the preceding step with a compound having the general formula I-G-Hal to obtain the compound having the following general formula:

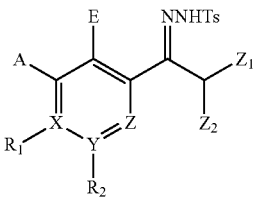

and Hal represents a halogen selected from a bromine atom and a chlorine atom, where G is as defined above;
3. metal-catalysed coupling carried out on the compound obtained in the preceding step followed by a treatment allowing the introduction of group -(L)$_n$-B and obtaining the compound having the following general formula:

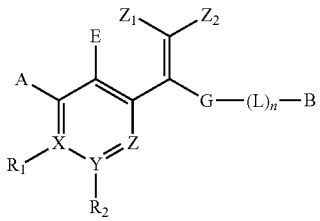

and where L, n and B are as defined above.

7. A pharmaceutical composition comprising at least one compound of formula (II) as defined in claim 1, or a pharmaceutically acceptable salt thereof, in combination with one or more pharmaceutically acceptable excipients.

8. The pharmaceutical composition according to claim 7, further comprising at least one other active principle, selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocine, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrozole, letrozole, tamoxifen, octreotide, lanreotide, (Z)-3-[2,4-dimethyl-5-(2-oxo-1,2-dihydro-indol-3-ylidenemethyl)-1H-pyrrol-3-yl]propionic acid, 4-((9-chloro-7-(2,6-difluorophenyl)-5H-pyrimidol(5,4-d)(2)benzazepin-2-yl)amino)benzoic acid, 5,6-dimethyl-xanthenone-4-acetic acid and 3-(4-(1,2-diphenylbut-1-enyl)phenyl)acrylic acid.

9. A conjugate comprising the combination of:
   an antibody, an antibody fragment or equivalent;
   a linker molecule, and;
   a compound according to claim 1;
   covalently linked to each other.

10. The compound according to claim 1, wherein B is

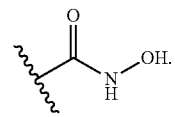 [SMILES: *C(=O)NO]

11. A method for treating cancer comprising administering to a person in need thereof an effective amount of a pharmaceutical composition comprising:
   (i) at least one compound of formula (II) as defined in claim 1, and
   (ii) at least one other active principle
   wherein the administration of said combination of products is simultaneous, separate or sequential.

12. A method for decreasing or inhibiting tubulin polymerisation and for decreasing or inhibiting HDACs comprising administering to a person in need thereof an effective amount of a compound according to claim 1.

13. A method for treating cancer comprising administering to a person in need thereof an effective amount of a compound according to claim 1.

* * * * *